(12) United States Patent
Weir et al.

(10) Patent No.: US 10,987,123 B2
(45) Date of Patent: Apr. 27, 2021

(54) SURGICAL INSTRUMENTS WITH ARTICULATING SHAFTS

(71) Applicant: Ethicon Endo-Surgery, LLC, Guaynabo, PR (US)

(72) Inventors: Michael P. Weir, Blanchester, OH (US); Joseph B. Kraimer, Mason, OH (US); Frederick E. Shelton, IV, Hillsboro, OH (US); Stephen J. Balek, Springboro, OH (US); Zhifan F. Huang, Mason, OH (US); Sora Rhee, Pennsylvania Furnace, PA (US); Carl J. Draginoff, Jr., Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 646 days.

(21) Appl. No.: 15/393,990

(22) Filed: Dec. 29, 2016

(65) Prior Publication Data

US 2017/0105757 A1   Apr. 20, 2017

Related U.S. Application Data

(63) Continuation of application No. 13/538,720, filed on Jun. 29, 2012, now abandoned.

(51) Int. Cl.
*A61B 17/32* (2006.01)
*A61B 18/14* (2006.01)
(Continued)

(52) U.S. Cl.
CPC ......... *A61B 17/320092* (2013.01); *A61B 17/00234* (2013.01); *A61B 18/08* (2013.01);
(Continued)

(58) Field of Classification Search
CPC ........... A61B 17/29; A61B 17/320016; A61B 17/320068; A61B 2017/003;
(Continued)

(56) References Cited

U.S. PATENT DOCUMENTS

| 969,528 A | 9/1910 | Disbrow |
|---|---|---|
| 1,570,025 A | 1/1926 | Young |

(Continued)

FOREIGN PATENT DOCUMENTS

| CA | 2535467 A1 | 4/1993 |
|---|---|---|
| CN | 2460047 Y | 11/2001 |

(Continued)

OTHER PUBLICATIONS

AST Products, Inc., "Principles of Video Contact Angle Analysis," 20 pages, (2006).

(Continued)

*Primary Examiner* — Tan-Uyen T Ho
*Assistant Examiner* — Chima U Igboko

(57) ABSTRACT

Various example embodiments described herein are directed to articulating surgical instruments for treating tissue comprising an end effector and a shaft extending proximally from the end effector along a longitudinal axis. In certain embodiments, the shaft comprises a plurality of transverse spacer members as well as first and second rotatable members extending through at least a portion of the plurality of transverse spacer members. The first and second rotatable members may both be biased away from the longitudinal axis such that their respective directions of bias vary with rotation of the first rotatable member. When the respective directions of bias of the first and second rotatable members oppose one another, the shaft may be substantially straight.

(Continued)

When the respective directions of bias of the first and second rotatable members are aligned with one another, the shaft may articulate away from the longitudinal axis in the direction of the alignment.

19 Claims, 65 Drawing Sheets

(51) Int. Cl.
    *A61B 34/37*     (2016.01)
    *A61B 17/00*     (2006.01)
    *A61B 18/08*     (2006.01)
    *A61B 34/30*     (2016.01)
    *A61B 17/29*     (2006.01)
    *A61B 17/22*     (2006.01)

(52) U.S. Cl.
    CPC ........ *A61B 18/082* (2013.01); *A61B 18/1445* (2013.01); *A61B 34/30* (2016.02); *A61B 34/37* (2016.02); *A61B 2017/00314* (2013.01); *A61B 2017/00318* (2013.01); *A61B 2017/00323* (2013.01); *A61B 2017/00327* (2013.01); *A61B 2017/00331* (2013.01); *A61B 2017/00477* (2013.01); *A61B 2017/22018* (2013.01); *A61B 2017/2923* (2013.01); *A61B 2017/2927* (2013.01); *A61B 2017/320088* (2013.01); *A61B 2017/320094* (2017.08); *A61B 2017/320095* (2017.08)

(58) Field of Classification Search
    CPC ........... A61B 2017/22015; A61B 2017/55018; A61B 2017/2927; A61B 2017/2932; A61B 2017/320072; A61B 2017/294; A61B 34/30; A61B 34/76–77; A61B 2034/301–306
    USPC ..................................................... 606/169, 1
    See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |

(56) References Cited

U.S. PATENT DOCUMENTS

| | | |
|---|---|---|
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |

(56) References Cited

U.S. PATENT DOCUMENTS

| | | |
|---|---|---|
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |

(56) References Cited

U.S. PATENT DOCUMENTS

| | | |
|---|---|---|
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |

(56) References Cited

U.S. PATENT DOCUMENTS

| | | |
|---|---|---|
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |

(56) References Cited

U.S. PATENT DOCUMENTS

| | | |
|---|---|---|
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |

(56) References Cited

U.S. PATENT DOCUMENTS

| | | |
|---|---|---|
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |

(56) References Cited

U.S. PATENT DOCUMENTS

| | | |
|---|---|---|
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |

(56) References Cited

U.S. PATENT DOCUMENTS

| | | |
|---|---|---|
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |

(56) References Cited

U.S. PATENT DOCUMENTS

| | | |
|---|---|---|
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,149 B2 | 1/2013 | Govari et al. |
| 8,357,158 B2 | 1/2013 | McKenna et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |

(56) References Cited

U.S. PATENT DOCUMENTS

| | | |
|---|---|---|
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |

(56) References Cited

U.S. PATENT DOCUMENTS

| | | |
|---|---|---|
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,695 B2 | 5/2015 | Giordano et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |

(56) References Cited

U.S. PATENT DOCUMENTS

| | | |
|---|---|---|
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,690,362 B2 | 6/2017 | Leimbach et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |

(56) References Cited

U.S. PATENT DOCUMENTS

| | | |
|---|---|---|
| 9,717,552 B2 | 8/2017 | Cosman et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,802,033 B2 | 10/2017 | Hibner et al. |
| 9,808,246 B2 | 11/2017 | Shelton, IV et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,901,383 B2 | 2/2018 | Hassler, Jr. |
| 9,907,563 B2 | 3/2018 | Germain et al. |
| 9,913,656 B2 | 3/2018 | Stulen |
| 9,913,680 B2 | 3/2018 | Voegele et al. |
| 9,918,730 B2 | 3/2018 | Trees et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,974,539 B2 | 5/2018 | Yates et al. |
| 9,987,033 B2 | 6/2018 | Neurohr et al. |
| 10,004,526 B2 | 6/2018 | Dycus et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,070,916 B2 | 9/2018 | Artale |
| 10,080,609 B2 | 9/2018 | Hancock et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,111,703 B2 | 10/2018 | Cosman, Jr. et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,410 B2 | 11/2018 | Strobl et al. |
| 10,130,412 B2 | 11/2018 | Wham |
| 10,154,848 B2 | 12/2018 | Chernov et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,179,022 B2 | 1/2019 | Yates et al. |
| 10,188,455 B2 | 1/2019 | Hancock et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,238,391 B2 | 3/2019 | Leimbach et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,263,171 B2 | 4/2019 | Wiener et al. |
| 10,265,117 B2 | 4/2019 | Wiener et al. |
| 10,265,118 B2 | 4/2019 | Gerhardt |
| 10,271,840 B2 | 4/2019 | Sapre |
| 10,278,721 B2 | 5/2019 | Dietz et al. |
| 10,285,724 B2 | 5/2019 | Faller et al. |
| 10,285,750 B2 | 5/2019 | Coulson et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,602 B2 | 7/2019 | Strobl et al. |
| 10,342,606 B2 | 7/2019 | Cosman et al. |
| 10,349,999 B2 | 7/2019 | Yates et al. |
| 10,357,303 B2 | 7/2019 | Conlon et al. |
| 10,363,084 B2 | 7/2019 | Friedrichs |
| 10,376,305 B2 | 8/2019 | Yates et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,986 B2 | 10/2019 | Zikorus et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,485,607 B2 | 11/2019 | Strobl et al. |
| 10,492,849 B2 | 12/2019 | Juergens et al. |
| 10,512,795 B2 | 12/2019 | Voegele et al. |
| 10,517,627 B2 | 12/2019 | Timm et al. |
| 10,524,854 B2 | 1/2020 | Woodruff et al. |
| 10,524,872 B2 | 1/2020 | Stewart et al. |
| 10,537,351 B2 | 1/2020 | Shelton, IV et al. |
| 10,543,008 B2 | 1/2020 | Vakharia et al. |
| 10,548,655 B2 | 2/2020 | Scheib et al. |
| 10,555,769 B2 | 2/2020 | Worrell et al. |

(56) References Cited

U.S. PATENT DOCUMENTS

| | | |
|---|---|---|
| RE47,996 E | 5/2020 | Turner et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |

(56) References Cited

U.S. PATENT DOCUMENTS

| | | |
|---|---|---|
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0282335 A1* | 12/2007 | Young ................. B25B 23/142 606/50 |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0024141 A1* | 1/2009 | Stahler ................. A61B 34/37 606/130 |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0028964 A1 | 2/2011 | Edwards |
| 2011/0071523 A1 | 3/2011 | Dickhans |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0160725 A1 | 6/2011 | Kabaya et al. |
| 2011/0238010 A1 | 9/2011 | Kirschenman et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |

(56) References Cited

U.S. PATENT DOCUMENTS

| | | |
|---|---|---|
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136386 A1 | 5/2012 | Kishida et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0211542 A1 | 8/2012 | Racenet |
| 2012/0253328 A1 | 10/2012 | Cunningham et al. |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0277410 A1 | 10/2013 | Fernandez et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0121569 A1 | 5/2014 | Schafer et al. |
| 2014/0135804 A1 | 5/2014 | Weisenburgh, II et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0246475 A1 | 9/2014 | Hall et al. |
| 2014/0263541 A1 | 9/2014 | Leimbach et al. |
| 2014/0263552 A1 | 9/2014 | Hall et al. |
| 2014/0276754 A1 | 9/2014 | Gilbert et al. |
| 2014/0276797 A1 | 9/2014 | Batchelor et al. |
| 2014/0276806 A1 | 9/2014 | Heim |
| 2015/0032150 A1 | 1/2015 | Ishida et al. |
| 2015/0080876 A1 | 3/2015 | Worrell et al. |
| 2015/0080887 A1 | 3/2015 | Sobajima et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0238260 A1 | 8/2015 | Nau, Jr. |
| 2015/0257780 A1 | 9/2015 | Houser |
| 2015/0272659 A1 | 10/2015 | Boudreaux et al. |
| 2015/0282879 A1 | 10/2015 | Ruelas |
| 2015/0313667 A1 | 11/2015 | Allen, IV |
| 2015/0320481 A1 | 11/2015 | Cosman, Jr. et al. |
| 2016/0045248 A1 | 2/2016 | Unger et al. |
| 2016/0051316 A1 | 2/2016 | Boudreaux |
| 2016/0157927 A1 | 6/2016 | Corbett et al. |
| 2016/0175029 A1 | 6/2016 | Witt et al. |
| 2016/0199125 A1 | 7/2016 | Jones |
| 2016/0206342 A1 | 7/2016 | Robertson et al. |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0324537 A1 | 11/2016 | Green et al. |
| 2016/0367281 A1 | 12/2016 | Gee et al. |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000553 A1 | 1/2017 | Wiener et al. |
| 2017/0000554 A1 | 1/2017 | Yates et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0164994 A1 | 6/2017 | Smith |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0245875 A1 | 8/2017 | Timm et al. |
| 2017/0312014 A1 | 11/2017 | Strobl et al. |
| 2017/0312015 A1 | 11/2017 | Worrell et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325874 A1 | 11/2017 | Noack et al. |
| 2017/0360468 A1 | 12/2017 | Eichmann et al. |
| 2018/0014872 A1 | 1/2018 | Dickerson |
| 2018/0028257 A1 | 2/2018 | Yates et al. |
| 2018/0042658 A1 | 2/2018 | Shelton, IV et al. |
| 2018/0064961 A1 | 3/2018 | Wiener et al. |
| 2018/0078277 A1 | 3/2018 | Illizaliturri-Sanchez et al. |
| 2018/0098785 A1 | 4/2018 | Price et al. |
| 2018/0098808 A1 | 4/2018 | Yates et al. |
| 2018/0146976 A1 | 5/2018 | Clauda et al. |
| 2018/0177545 A1 | 6/2018 | Boudreaux et al. |
| 2018/0235691 A1 | 8/2018 | Voegele et al. |
| 2018/0280083 A1 | 10/2018 | Parihar et al. |
| 2019/0021783 A1 | 1/2019 | Asher et al. |
| 2019/0105067 A1 | 4/2019 | Boudreaux et al. |
| 2019/0201048 A1 | 7/2019 | Stulen et al. |
| 2019/0209201 A1 | 7/2019 | Boudreaux et al. |
| 2019/0262030 A1 | 8/2019 | Faller et al. |

(56) References Cited

U.S. PATENT DOCUMENTS

| | | |
|---|---|---|
| 2019/0274700 A1 | 9/2019 | Robertson et al. |
| 2019/0282288 A1 | 9/2019 | Boudreaux |
| 2019/0282292 A1 | 9/2019 | Wiener et al. |
| 2020/0015883 A1 | 1/2020 | Batross et al. |
| 2020/0022724 A1 | 1/2020 | Worrell et al. |
| 2020/0030021 A1 | 1/2020 | Yates et al. |
| 2020/0054382 A1 | 2/2020 | Yates et al. |
| 2020/0078085 A1 | 3/2020 | Yates et al. |
| 2020/0078609 A1 | 3/2020 | Messerly et al. |
| 2020/0085465 A1 | 3/2020 | Timm et al. |
| 2020/0113624 A1 | 4/2020 | Worrell et al. |
| 2020/0138473 A1 | 5/2020 | Shelton, IV et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 101474081 A | 7/2009 |
| CN | 102100582 A | 6/2011 |
| CN | 202027624 U | 11/2011 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | 2000210299 A | 8/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2007008710 A2 | 1/2007 |
| WO | WO-2008118709 A1 | 10/2008 |
| WO | WO-2008130793 A1 | 10/2008 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |

(56) References Cited

FOREIGN PATENT DOCUMENTS

| WO | WO-2011060031 A1 | 5/2011 |
|---|---|---|
| WO | WO-2012044606 A2 | 4/2012 |
| WO | WO-2012/150567 A1 | 11/2012 |

OTHER PUBLICATIONS

Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
http://www.apicalinstr.com/generators.htm.
http://www.medicalexpo.com/medical-manufacturer/electrosurgical-generator-6951.html.
Covidien 501(k) Summary Sonicision, dated Feb. 24, 2011 (7 pages).
Fowler, K.R., "A Programmable, Arbitrary Waveform Electrosurgical Device," IEEE Engineering in Medicine and Biology Society 10th Annual International Conference, pp. 1324, 1325 (1988).
http://www.dotmed.com/listing/electrosurical-unit/ethicon/ultracision-g110-/1466724.
http:/www.ethicon.com/gb-en/healthcare-professionals/products/energy-devices/capital//ge . . . .
http://www.megadyne.com/es_generator.php.
Incropera et al., Fundamentals of Heat and Mass Transfer, Wiley, New York (1990). (Book—not attached).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Campbell et al, "Thermal Imaging in Surgery," p. 19-3, in Medical Infrared Imaging, N. A. Diakides and J. D. Bronzino, Eds. (2008).
http://www.4-traders.com/JOHNSON-JOHNSON-4832/news/Johnson-Johnson-Ethicon-E . . . .
http://www.valleylab.com/product/es/generators/index.html.
Gerhard, Glen C., "Surgical Electrotechnology: Quo Vadis?," IEEE Transactions on Biomedical Engineering, vol. BME-31, No. 12, pp. 787-792, Dec. 1984.
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Graff, K.F., "Elastic Wave Propagation in a Curved Sonic Transmission Line," IEEE Transactions on Sonics and Ultrasonics, SU-17(1), 1-6 (1970).
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).

(56) References Cited

OTHER PUBLICATIONS

Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe,Integrated Circuit Engineering, Addison-Wesley Publishing, Reading, MA (1979). (book—not attached).
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.

* cited by examiner

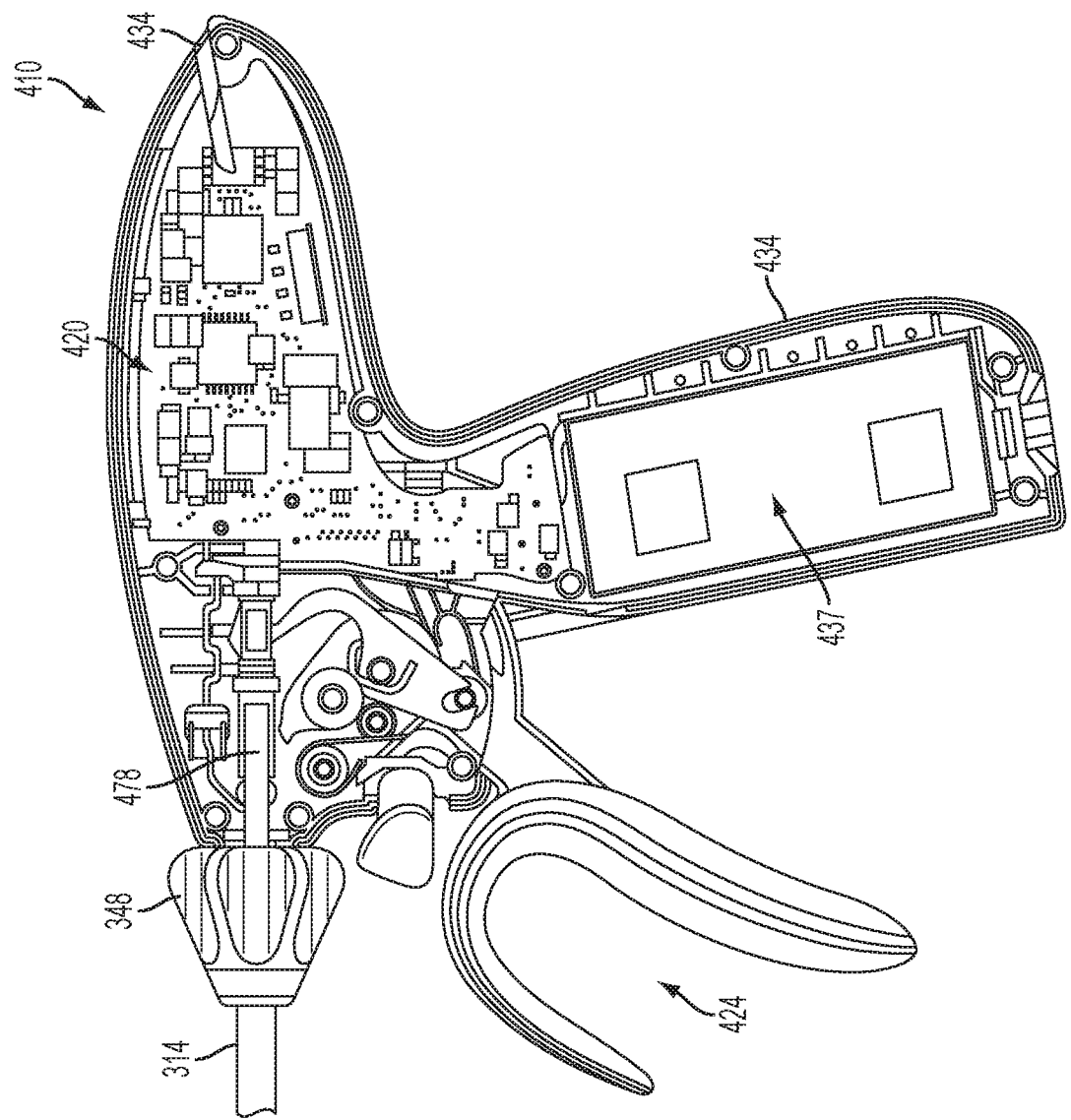

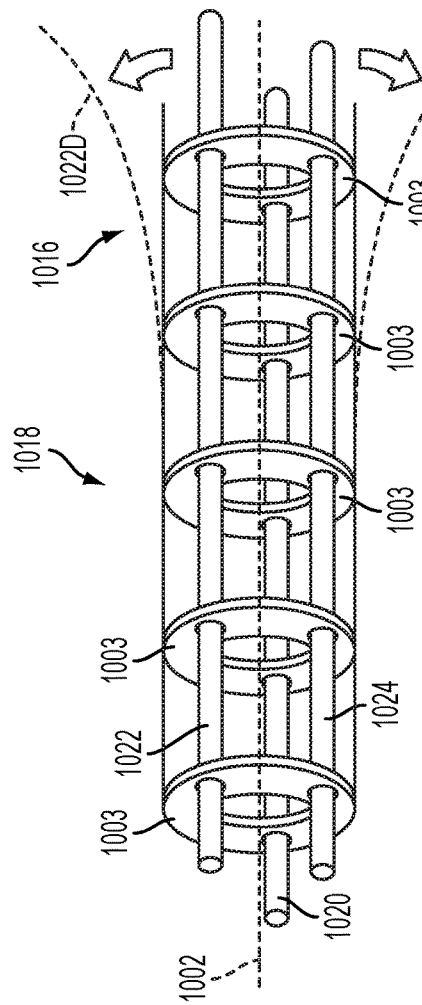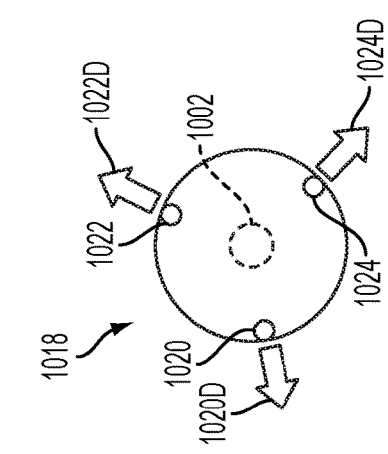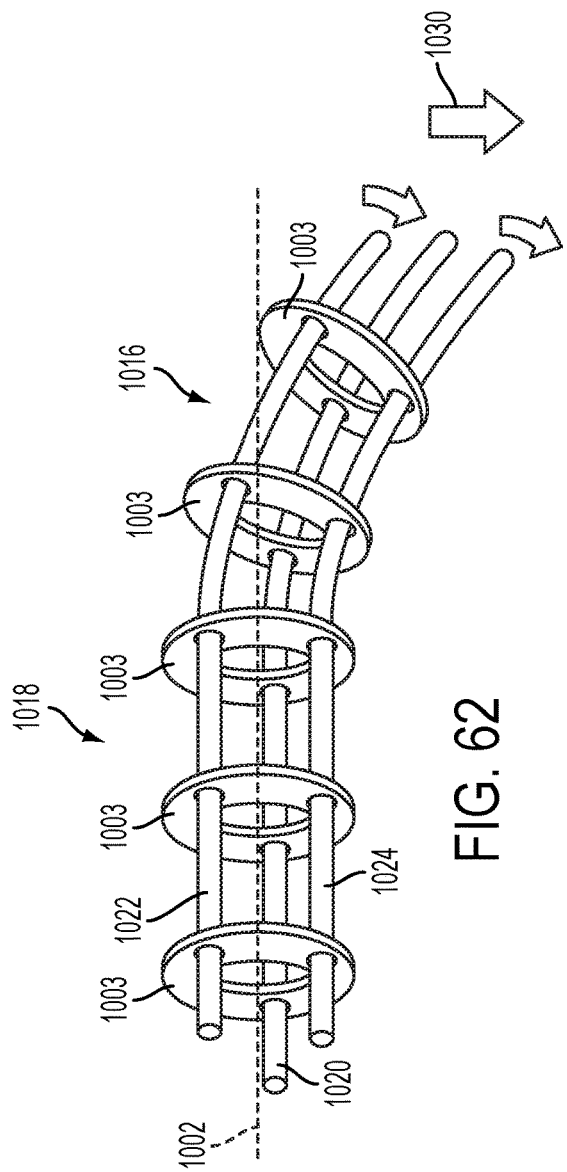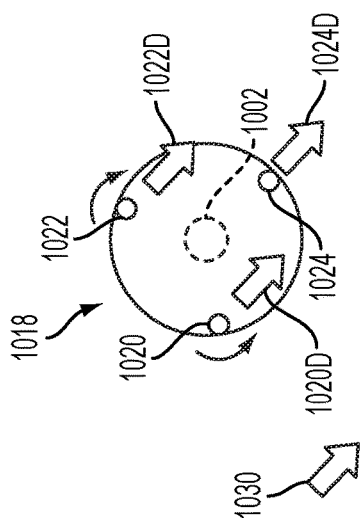

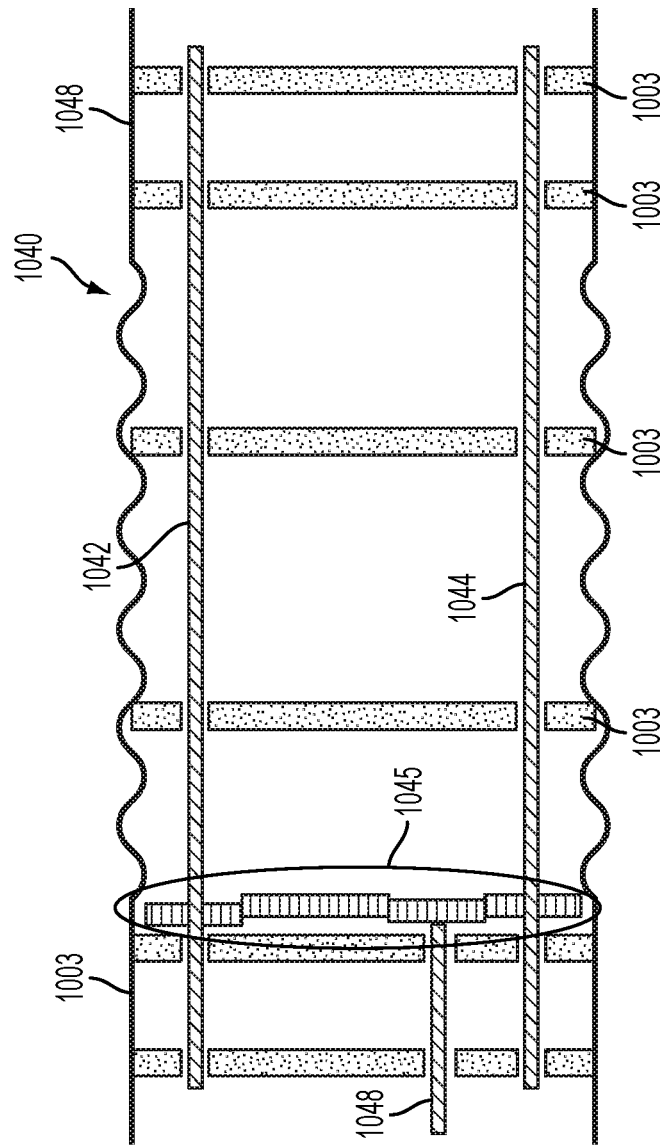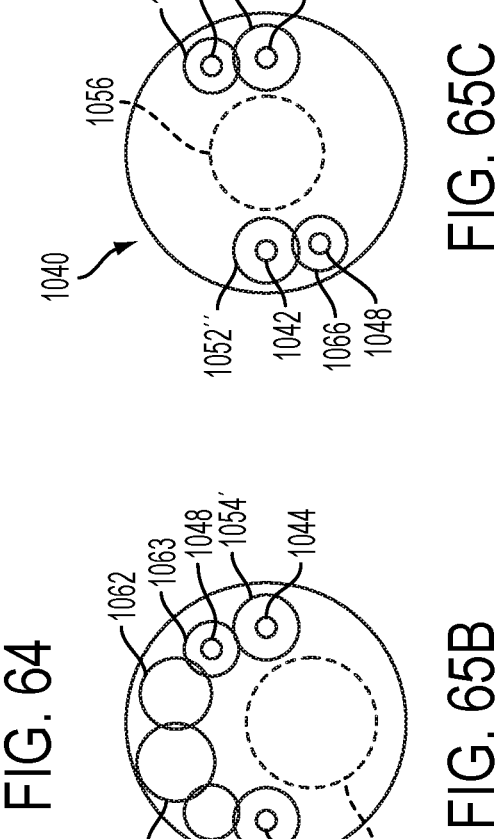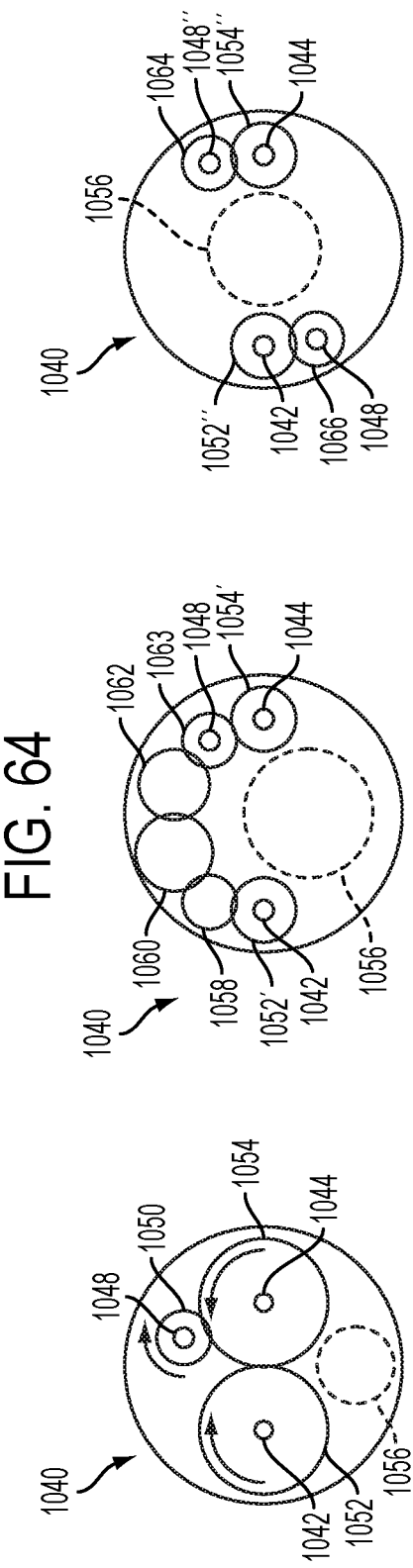

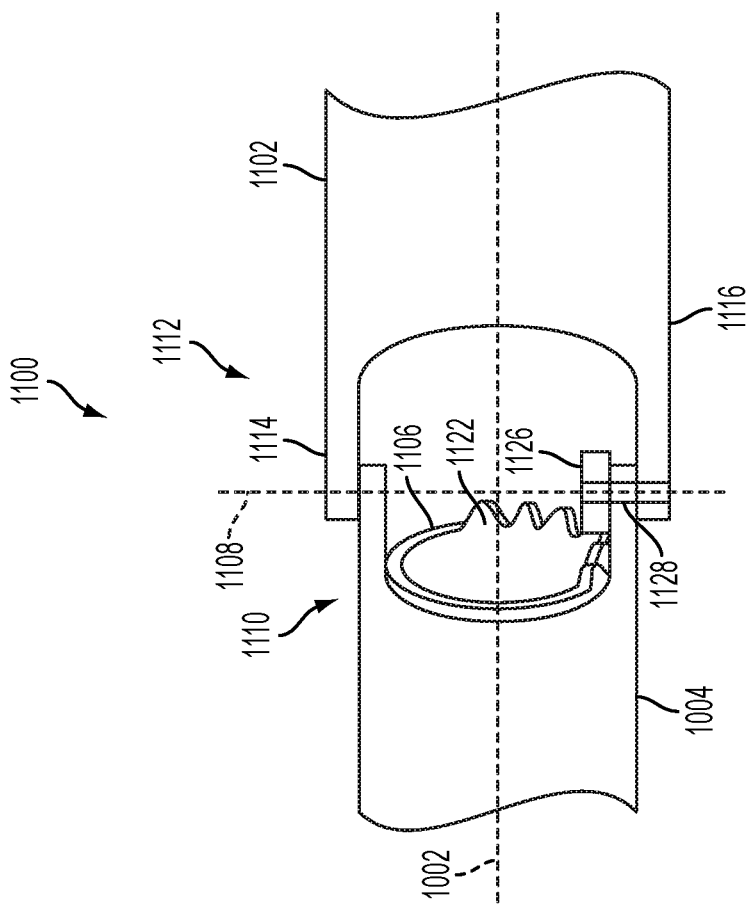

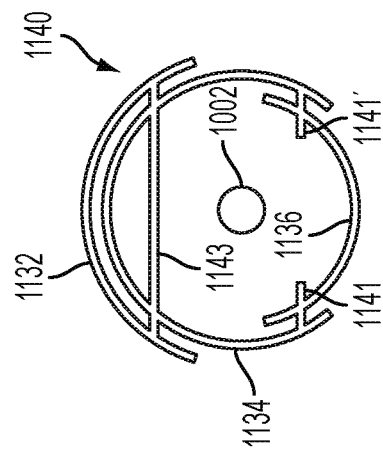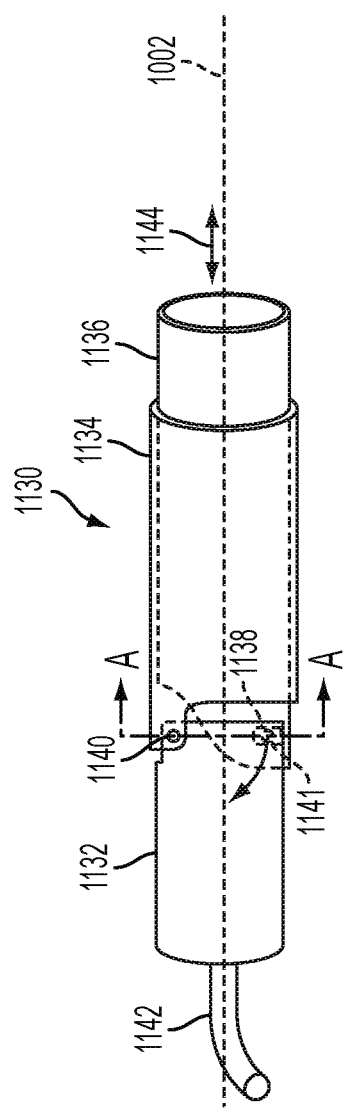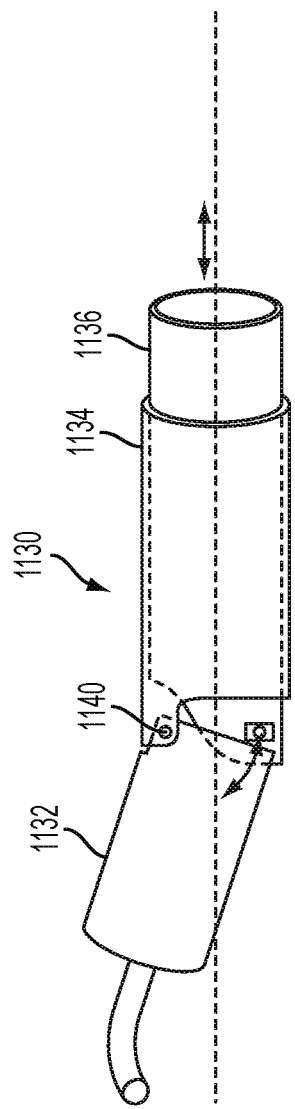

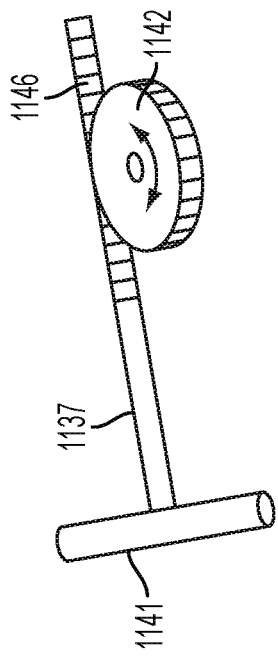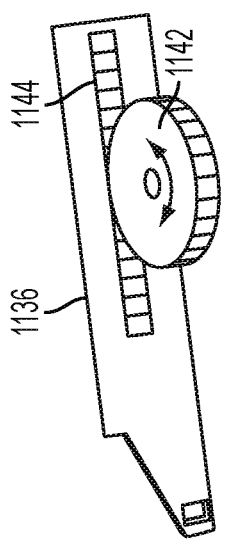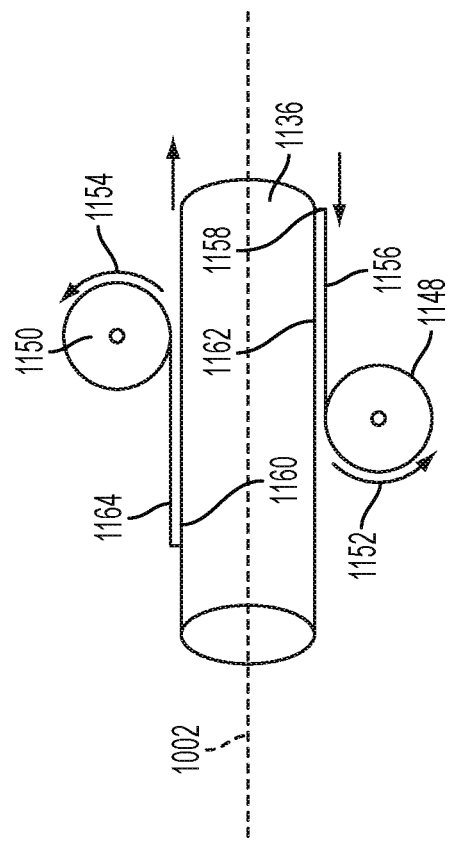
FIG. 77
FIG. 78
FIG. 79

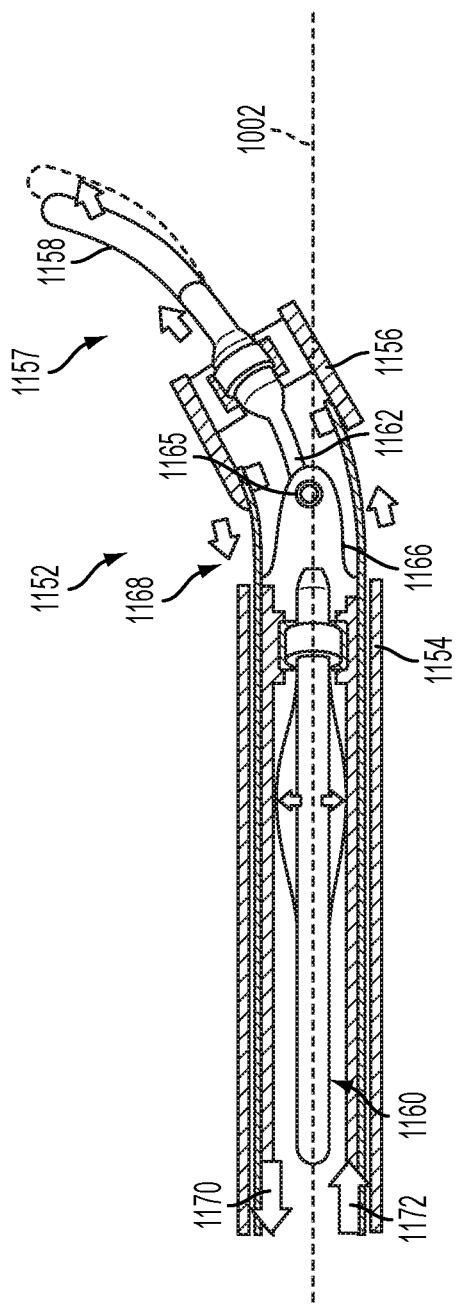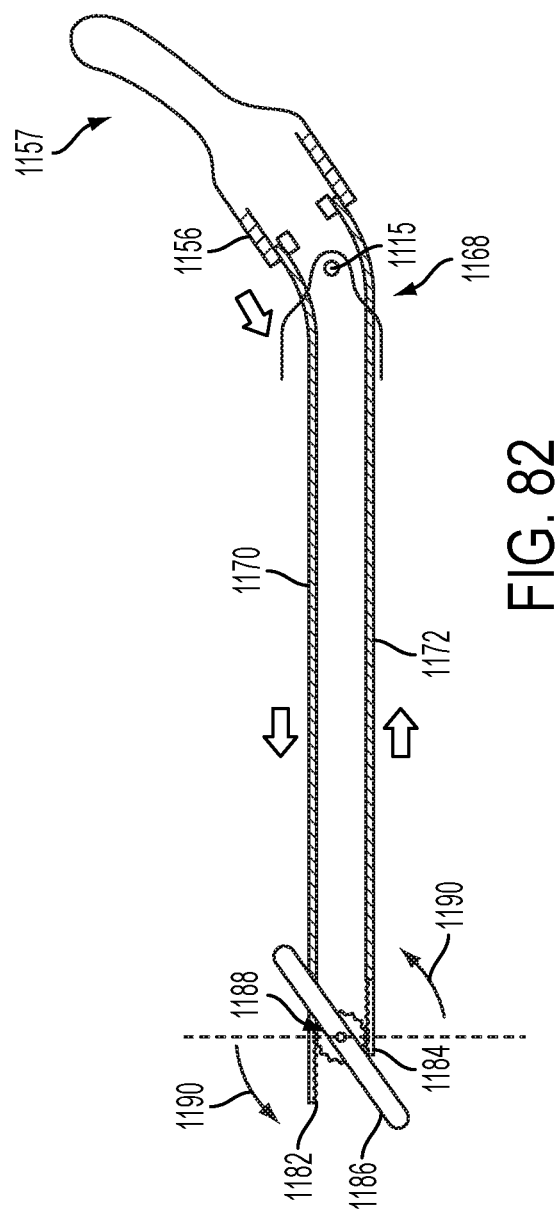

SURGICAL INSTRUMENTS WITH ARTICULATING SHAFTS

CROSS-REFERENCE TO RELATED APPLICATIONS

This application is a continuation application claiming priority under 35 U.S.C. § 120 to U.S. patent application Ser. No. 13/538,720, entitled "Surgical Instruments with Articulating Shafts," filed on Jun. 29, 2012, now U.S. Patent Application Publication No. 2014/0005705, the entire disclosure of which is hereby incorporated by reference herein.

The present application is related to the following, commonly owned U.S. patent applications, which are incorporated herein by reference in their entirety:

U.S. application Ser. No. 13/539,096, entitled "Haptic Feedback Devices for Surgical Robot," now U.S. Pat. No. 9,198,714;

U.S. application Ser. No. 13/539,110, entitled "Lockout Mechanism for Use with Robotic Electrosurgical Device," now U.S. Pat. No. 9,326,788;

U.S. application Ser. No. 13/539,117, entitled "Closed Feedback Control for Electrosurgical Device," now U.S. Pat. No. 9,226,767;

U.S. application Ser. No. 13/538,588, entitled "Surgical Instruments with Articulating Shafts," now U.S. Pat. No. 9,393,037;

U.S. application Ser. No. 13/538,601, entitled "Ultrasonic Surgical Instruments with Distally Positioned Transducers," now U.S. Patent Application Publication No. 2014/0005702;

U.S. application Ser. No. 13/538,700, entitled "Surgical Instruments with Articulating Shafts," now U.S. Pat. No. 9,408,622;

U.S. application Ser. No. 13/538,711, entitled "Ultrasonic Surgical Instruments with Distally Positioned Jaw Assemblies," now U.S. Pat. No. 9,351,754;

U.S. application Ser. No. 13/538,733, entitled "Ultrasonic Surgical Instruments with Control Mechanisms," now U.S. Patent Application Publication No. 2014/0005681; and U.S. application Ser. No. 13/657,553, entitled "Surgical Instruments with Fluid Management System," now U.S. Pat. No. 9,095,367.

Applicant also owns the following patent applications that are each incorporated by reference in their respective entireties:

U.S. patent application Ser. No. 13/536,271, filed on Jun. 28, 2012 and entitled "Flexible Drive Member," now U.S. Pat. No. 9,204,879.

U.S. patent application Ser. No. 13/536,288, filed on Jun. 28, 2012 and entitled "Multi-Functional Powered Surgical Device with External Dissection Features," now U.S. Patent Application Publication No. 2014/0005718.

U.S. patent application Ser. No. 13/536,295, filed on Jun. 28, 2012 and entitled "Rotary Actuatable Closure Arrangement for Surgical End Effector," now U.S. Pat. No. 9,119,657.

U.S. patent application Ser. No. 13/536,326, filed on Jun. 28, 2012 and entitled "Surgical End Effectors Having Angled Tissue-Contacting Surfaces," now U.S. Pat. No. 9,289,256.

U.S. patent application Ser. No. 13/536,303, filed on Jun. 28, 2012 and entitled "Interchangeable End Effector Coupling Arrangement," now U.S. Pat. No. 9,028,494.

U.S. patent application Ser. No. 13/536,393, filed on Jun. 28, 2012 and entitled "Surgical End Effector Jaw and Electrode Configurations," now U.S. Patent Application Publication No. 2014/0005640.

U.S. patent application Ser. No. 13/536,362, filed on Jun. 28, 2012 and entitled "Multi-Axis Articulating and Rotating Surgical Tools," now U.S. Pat. No. 9,125,662.

U.S. patent application Ser. No. 13/536,417, filed on Jun. 28, 2012 and entitled "Electrode Connections for Rotary Driven Surgical Tools," now U.S. Pat. No. 9,101,385.

BACKGROUND

Various embodiments are directed to surgical devices, including various articulatable shafts for use with surgical devices.

Ultrasonic surgical devices, such as ultrasonic scalpels, are used in many applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device comprises a proximally-positioned ultrasonic transducer and an instrument coupled to the ultrasonic transducer having a distally-mounted end effector comprising an ultrasonic blade to cut and seal tissue. The end effector is typically coupled either to a handle and/or a robotic surgical implement via a shaft. The blade is acoustically coupled to the transducer via a waveguide extending through the shaft. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a haemostatic seal. A surgeon can control the cutting speed and coagulation by the force applied to the tissue by the end effector, the time over which the force is applied and the selected excursion level of the end effector.

Also used in many surgical applications are electrosurgical devices. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form haemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

With respect to both ultrasonic and electrosurgical devices, it is often desirable for clinicians to articulate a distal portion of the instrument shaft in order to direct the application of ultrasonic and/or RF energy. Bringing about and controlling such articulation, however, is often a considerable challenge.

DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 18A illustrates a side view of a handle of one example embodiment of the surgical instrument of FIG. 17 with a half handle body removed to illustrate various components therein.

FIGS. 43-46A illustrate an alternate embodiment of the instrument mounting portion showing an alternate example mechanism for differential translation of members along the axis of the shaft (e.g., for articulation).

FIG. 59 illustrates a diagram showing a cut-away view of one example embodiment of a pivotable portion of a shaft comprising three biased rotatable members.

FIG. 60 illustrates a cross-sectional diagram of the example embodiment of FIG. 59.

FIG. 61 illustrates a diagram showing a cut-away view of one example embodiment of a pivotable portion of the shaft of FIGS. 59-60 with the rotatable members rotated such that their respective bias directions are aligned.

FIG. 62 illustrates a cross-sectional diagram of shaft of FIG. 59 arranged as illustrated in FIG. 61.

FIG. 64 illustrates a cross-sectional view of the shaft of the instrument of FIG. 63 including a gear cluster for coupling rotating members to the knob of the instrument of FIG. 63.

FIGS. 65A-65C illustrate cross-sectional views of the shaft of the instrument of FIG. 63 showing different embodiments of the gear cluster.

FIGS. 67-70 illustrate various example embodiments of a geared articulating shaft for use with a surgical instrument.

FIG. 71 illustrates one example embodiment of an articulating shaft that may be articulated by reciprocating motion along a longitudinal axis of a translating member, wherein the translating member is a hollow inner tube.

FIG. 72 illustrates a cross section of one example embodiment of the shaft taken along a line AB illustrated in FIG. 71.

FIG. 73 illustrates one example embodiment of the shaft as articulated by the translating member.

FIG. 77 illustrates another embodiment of a mechanism for translating the translating member of FIGS. 71-73 distally and proximally, for example, in the context of a surgical robot.

FIG. 78 illustrates an alternate embodiment of the mechanism shown in FIG. 77 implemented with respect to the translating member of FIGS. 74-76.

FIG. 79 illustrates yet another embodiment of a mechanism for translating the translating member.

FIG. 80 illustrates one embodiment of an articulating shaft that may be used in conjunction with an end effector comprising an ultrasonic blade.

FIG. 82 illustrates a diagram of one embodiment of the shaft utilized in conjunction with a manual device for actuating articulation.

DETAILED DESCRIPTION

Figure 1:
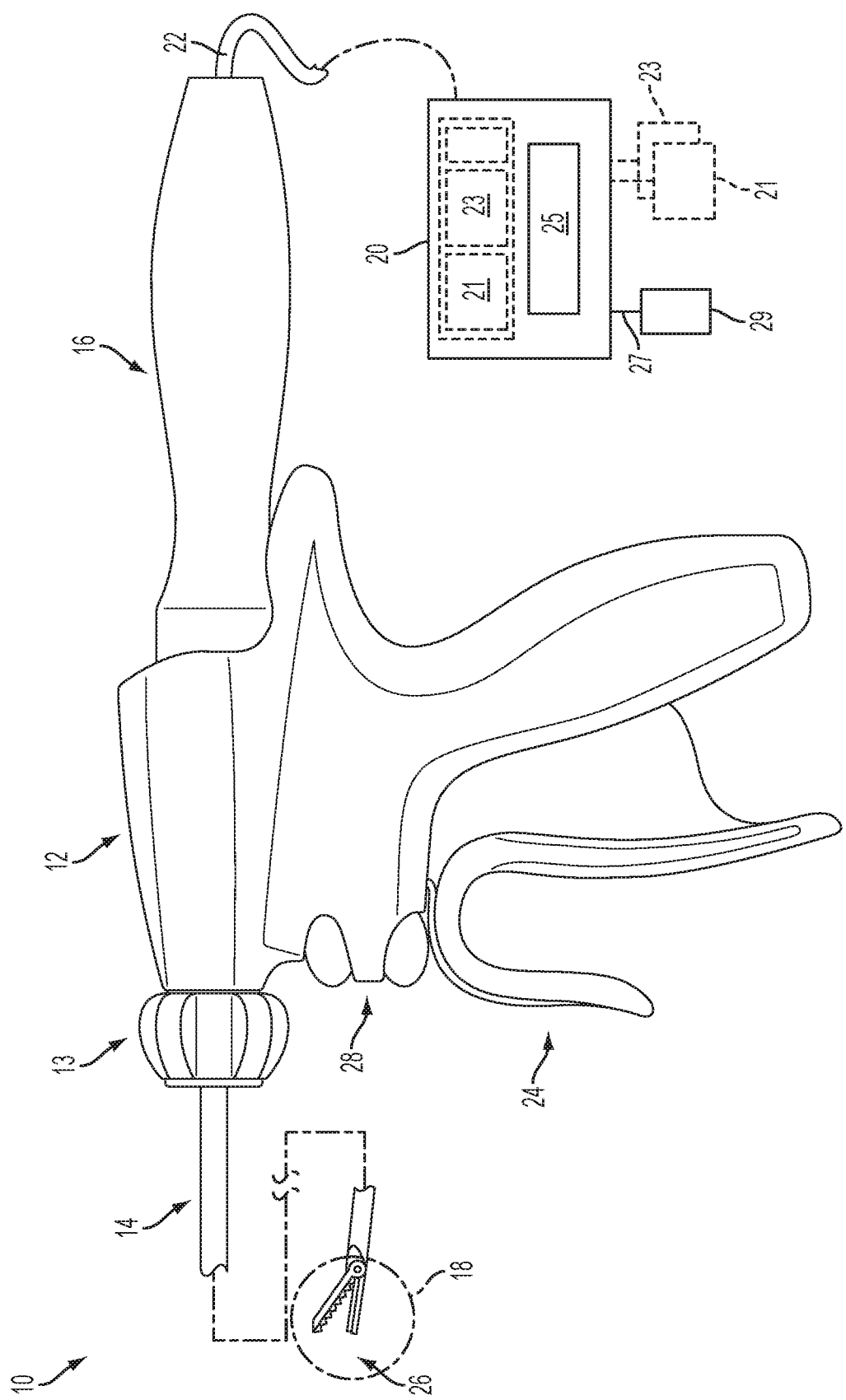
FIG. 1 illustrates one embodiment of a surgical system including a surgical instrument and an ultrasonic generator.

Example embodiments described herein are directed to articulating surgical instruments, shafts thereof, and methods of using the same. The surgical instruments may comprise an end effector configured to treat tissue in any suitable manner. In some example embodiments, the end effector comprises an ultrasonic blade for cutting and/or coagulating tissue. Details of example ultrasonic blades and the operation thereof are provided herein. Also, in some example embodiments, the end effector can comprise one or more electrodes for providing electrical energy to tissue for cutting, coagulating and/or "welding" tissue. Surgical instruments described herein may be utilized in different surgical settings. For example, different embodiments may be optimized for endoscopic, laparoscopic and/or traditional open surgical techniques. Also, different example embodiments of the surgical instruments described herein may be optimized for manual use by a clinician and/or for robotic use by a clinician in conjunction with a surgical robot.

Various example embodiments of surgical instruments described herein comprise an elongated shaft extending proximally from the end effector along a longitudinal axis. The shaft may be pivotable away from the longitudinal axis so as to articulate the end effector, allowing a clinician more flexibility to position the end effector at a desired location. Articulation of the shaft may be brought about in any suitable manner.

In some embodiments, the shaft comprises transverse spacer members extending along and transverse to the longitudinal axis. At least two pre-bent or otherwise biased rotatable members extend through some or all of the spacer members such that the direction of the bias of the rotatable members varies as the members rotate. When the at least two rotatable members are rotated such that the bias direction of all of the shafts oppose one another, the shaft may be straight. When the at least two rotatable members are rotated such that the bias directions of all of the shafts are in alignment, the shaft may articulate in a direction of the alignment.

In other example embodiments, the shaft comprises a proximal tube, and a distal tube pivotably coupled to one another at a pair of devises. The end effector may be coupled to the shaft distal from the distal tube. A rotatable inner tube may be positioned within the proximal tube and may define a distally directed set of teeth. The distal clevis may also define a set of teeth that interlock with the teeth of the rotatable inner tube such that rotation of the inner tube causes articulation of the distal tube about its interface with the distal tube.

In other example embodiments, the shaft comprises a proximal tube and a distal tube pivotably coupled to one another at a first hinge interface. A translating member may extend through the proximal tube and may be coupled to the distal tube at a second hinge interface. The first and second hinge interfaces may be offset from one another about the longitudinal axis such that translation of the translating member along the longitudinal axis causes the proximal tube to pivot relative to the distal tube about the first hinge interface.

In other example embodiments, the shaft comprises a proximal tube and a distal tube pivotably coupled to the proximal tube. First and second translating members may be coupled to the distal tube and extend through the proximal tube such that proximally directed translation of one translating member or the other causes the distal tube to pivot away from the longitudinal axis in the direction of the proximally translated member.

In still other example embodiments, the shaft again comprises a proximal and a distal tube pivotably coupled to the proximal tube. A rigid translating member may be coupled to the distal tube via an intermediate linkage member such that distal translation of the translating member causes the distal tube to pivot about the first hinge interface away from the translating member.

In an additional example embodiment, a surgical instrument comprises an articulation neck positioned between the shaft and the end effector. The articulation neck may comprise a plurality of hollow neck members. A first hollow neck member may define a proximal end configured to receive a distal end of a second hollow neck member such that the first and second hollow neck members are pivotally coupled to each other. One or more translating members may extend proximally from the end effector through some or all of the hollow neck members. In some example embodiments, the translating member or members may be pulled proximally to place the articulation neck in compression and prevent articulation. Also, in some example embodiments, proximal motion of one translating member may pull the end effector away from the longitudinal axis in the direction of the translating member.

Reference will now be made in detail to several example embodiments, including embodiments showing example implementations of manual and robotic surgical instruments with end effectors comprising ultrasonic and/or electrosurgical elements. Wherever practicable similar or like reference numbers may be used in the figures and may indicate similar or like functionality. The figures depict example embodiments of the disclosed surgical instruments and/or methods of use for purposes of illustration only. One skilled in the art will readily recognize from the following description that alternative example embodiments of the structures and methods illustrated herein may be employed without departing from the principles described herein.

FIG. 1 is a right side view of one embodiment of an ultrasonic surgical instrument 10. In the illustrated embodiment, the ultrasonic surgical instrument 10 may be employed in various surgical procedures including endoscopic or traditional open surgical procedures. In one example embodiment, the ultrasonic surgical instrument 10 comprises a handle assembly 12, an elongated shaft assembly 14, and an ultrasonic transducer 16. The handle assembly 12 comprises a trigger assembly 24, a distal rotation assembly 13, and a switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical instrument 10 may be employed in more traditional open surgical procedures and in other embodiments, may be configured for use in endoscopic procedures. For the purposes herein, the ultrasonic surgical instrument 10 is described in terms of an endoscopic instrument; however, it is contemplated that an open and/or laparoscopic version of the ultrasonic surgical instrument 10 also may include the same or similar operating components and features as described herein.

In various embodiments, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example embodiments, the generator 20 also comprises an electrosurgery/RF generator module 23 for driving an electrosurgical device (or an electrosurgical embodiment of the ultrasonic surgical instrument 10). In various embodiments, the generator 20 may be formed integrally within the handle assembly 12. In such implementations, a battery would be co-located within the handle assembly 12 to act as the energy source. FIG. 18A and accompanying disclosures provide one example of such implementations. In some embodiments, the electrosurgery/RF generator module 23 may be configured to generate a therapeutic and/or subtherapeutic energy level. In the example embodiment illustrated in FIG. 1, the generator 20 includes a control system 25 integral with the generator 20, and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level. The generator 20 drives or excites the acoustic assembly at any suitable resonant frequency of the acoustic assembly and/or derives the therapeutic/sub-therapeutic electromagnetic/RF energy.

In one embodiment, the electrosurgical/RF generator module 23 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization).

In one embodiment, the electrosurgical/RF generator module 23 may be configured to deliver a sub-therapeutic RF signal to implement a tissue impedance measurement module. In one embodiment, the electrosurgical/RF generator module 23 comprises a bipolar radio frequency generator as described in more detail below. In one embodiment, the electrosurgical/RF generator module 12 may be configured to monitor electrical impedance Z, of tissue T and to control the characteristics of time and power level based on the tissue T by way of a return electrode on provided on a clamp member of the end effector assembly 26. Accordingly, the electrosurgical/RF generator module 23 may be configured for sub-therapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, titled "Electrosurgical Generator for Ultrasonic Surgical Instruments," the disclosure of which is herein incorporated by reference in its entirety.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting Blade Breakage Using Rate and/or Impedance Information); U.S. Pat. No. 6,662,127 (Method for Detecting Presence of a Blade in an Ultrasonic System); U.S. Pat. No. 6,679,899 (Method for Detecting Transverse Vibrations in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

It will be appreciated that in various embodiments, the generator 20 may be configured to operate in several modes. In one mode, the generator 20 may be configured such that the ultrasonic generator module 21 and the electrosurgical/RF generator module 23 may be operated independently.

For example, the ultrasonic generator module 21 may be activated to apply ultrasonic energy to the end effector assembly 26 and subsequently, either therapeutic sub-therapeutic RF energy may be applied to the end effector assembly 26 by the electrosurgical/RF generator module 23. As previously discussed, the subtherapeutic electrosurgical/RF energy may be applied to tissue clamped between claim elements of the end effector assembly 26 to measure tissue impedance to control the activation, or modify the activation, of the ultrasonic generator module 21. Tissue impedance feedback from the application of the subtherapeutic energy also may be employed to activate a therapeutic level of the electrosurgical/RF generator module 23 to seal the tissue (e.g., vessel) clamped between claim elements of the end effector assembly 26.

In another embodiment, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while the ultrasonic blade of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade portion of the end effector assembly 26 is employed for cutting the damaged tissue while the electrosurgical/RF energy is applied to electrode portions of the end effector clamp assembly 26 for sealing the tissue (or vessel).

When the generator 20 is activated via the triggering mechanism, in one embodiment electrical energy is continuously applied by the generator 20 to a transducer stack or assembly of the acoustic assembly. In another embodiment, electrical energy is intermittently applied (e.g., pulsed) by the generator 20. A phase-locked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system maintains the electrical current supplied to the acoustic assembly at a pre-selected constant level in order to achieve substantially constant excursion at the end effector 18 of the acoustic assembly. In yet another embodiment, a third feedback loop in the control system 25 monitors impedance between electrodes located in the end effector assembly 26. Although FIGS. 1-9 show a manually operated ultrasonic surgical instrument, it will be appreciated that ultrasonic surgical instruments may also be used in robotic applications, for example, as described herein, as well as combinations of manual and robotic applications.

In ultrasonic operation mode, the electrical signal supplied to the acoustic assembly may cause the distal end of the end effector 18, to vibrate longitudinally in the range of, for example, approximately 20 kHz to 250 kHz. According to various embodiments, the blade 22 may vibrate in the range of about 54 kHz to 56 kHz, for example, at about 55.5 kHz. In other embodiments, the blade 22 may vibrate at other frequencies including, for example, about 31 kHz or about 80 kHz. The excursion of the vibrations at the blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

Figure 2:
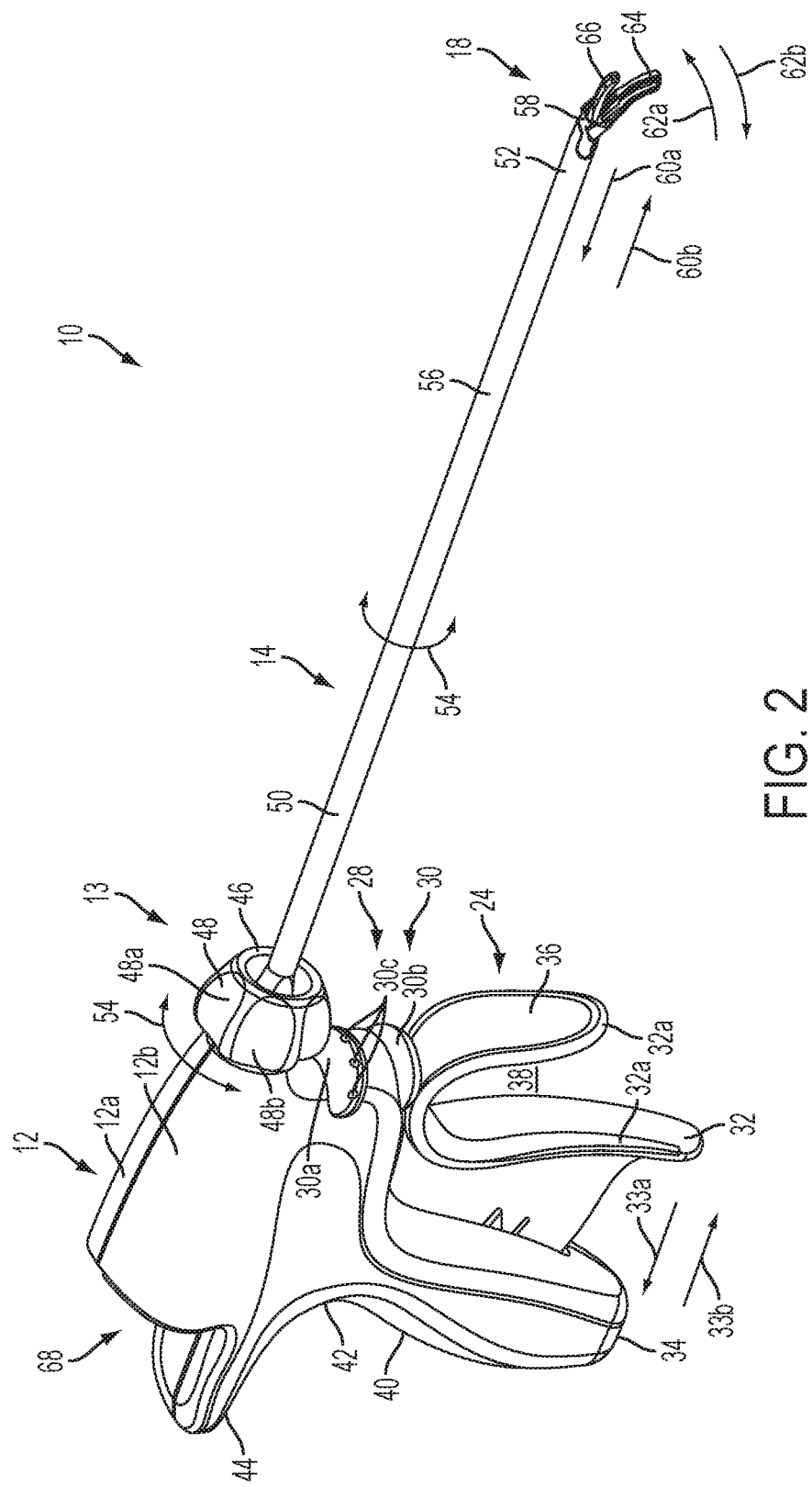
FIG. 2 illustrates one embodiment of the surgical instrument shown in FIG. 1.

FIG. 2 is a left perspective view of one example embodiment of the ultrasonic surgical instrument 10 showing the handle assembly 12, the distal rotation assembly 13, the elongated shaft assembly 14, and the end effector assembly 26. In the illustrated embodiment the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated shaft assembly 14 is received within the handle assembly 12 and the distal rotation assembly 13. More details relating to the connections between the elongated shaft assembly 14, the handle assembly 12, and the distal rotation assembly 13 are provided in the description of FIGS. 5 and 7.

In the illustrated embodiment, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33A toward the fixed handle 34 when the user applies a squeezing force against the trigger 32. A spring element 98 (FIG. 5) causes the trigger 32 to pivotally move in direction 33B when the user releases the squeezing force against the trigger 32.

In one example embodiment, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32a molded over the trigger 32 substrate. The overmolded resilient portion 32a is formed to provide a more comfortable contact surface for control of the trigger 32 in outward direction 33B. In one example embodiment, the overmolded resilient portion 32a may be provided over a portion of the elongated trigger hook 36. The proximal surface of the elongated trigger hook 32 remains uncoated or coated with a non-resilient substrate to enable the user to easily slide their fingers in and out of the aperture 38. In another embodiment, the geometry of the trigger forms a fully closed loop which defines an aperture suitably sized to receive one or multiple fingers of the user therethrough. The fully closed loop trigger also may comprise a resilient portion molded over the trigger substrate.

In one example embodiment, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example embodiment, the switch assembly 28 may comprise a toggle switch 30. The toggle switch 30 may be implemented as a single component with a central pivot 304 located within inside the handle assembly 12 to eliminate the possibility of simultaneous activation. In one example embodiment, the toggle switch 30 comprises a first projecting knob 30a and a second projecting knob 30b to set the power setting of the ultrasonic transducer 16 between a minimum power level (e.g., MIN) and a maximum power level (e.g., MAX). In another embodiment, the rocker switch may pivot between a standard setting and a special setting. The special setting may allow one or more special programs to be implemented by the device. The toggle switch 30 rotates about the central pivot as the first projecting knob 30a and the second projecting knob 30b are actuated. The one or more projecting knobs 30a, 30b are coupled to one or more arms that move through a small arc and cause electrical contacts to close or open an electric circuit to electrically energize or de-energize the ultrasonic transducer 16 in accordance with the activation of the first or second projecting knobs 30a, 30b. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30 is activated.

In one example embodiment, the first and second projecting knobs 30a, 30b are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30a, 30b may be configured to wrap around the side of the handle assembly 12 to some extent to be more easily accessible by variable finger lengths and to allow greater freedom of access to activation in awkward positions or for shorter fingers.

In the illustrated embodiment, the first projecting knob 30a comprises a plurality of tactile elements 30c, e.g., textured projections or "bumps" in the illustrated embodiment, to allow the user to differentiate the first projecting knob 30a from the second projecting knob 30b. It will be appreciated by those skilled in the art that several ergonomic features may be incorporated into the handle assembly 12. Such ergonomic features are described in U.S. Pat. App. Pub. No. 2009/0105750 entitled "Ergonomic Surgical Instruments" which is incorporated by reference herein in its entirety.

In one example embodiment, the toggle switch 30 may be operated by the hand of the user. The user may easily access the first and second projecting knobs 30*a*, 30*b* at any point while also avoiding inadvertent or unintentional activation at any time. The toggle switch 30 may readily operated with a finger to control the power to the ultrasonic assembly 16 and/or to the ultrasonic assembly 16. For example, the index finger may be employed to activate the first contact portion 30*a* to turn on the ultrasonic assembly 16 to a maximum (MAX) power level. The index finger may be employed to activate the second contact portion 30*b* to turn on the ultrasonic assembly 16 to a minimum (MIN) power level. In another embodiment, the rocker switch may pivot the instrument 10 between a standard setting and a special setting. The special setting may allow one or more special programs to be implemented by the instrument 10. The toggle switch 30 may be operated without the user having to look at the first or second projecting knob 30*a*, 30*b*. For example, the first projecting knob 30*a* or the second projecting knob 30*b* may comprise a texture or projections to tactilely differentiate between the first and second projecting knobs 30*a*, 30*b* without looking.

In other embodiments, the trigger 32 and/or the toggle switch 30 may be employed to actuate the electrosurgical/RF generator module 23 individually or in combination with activation of the ultrasonic generator module 21.

In one example embodiment, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46*a* that is exposed at the distal end. The end cap portion 46*a* of the hub 46 may contact the surface of a trocar during laparoscopic procedures. The hub 46 may be formed of a hard durable plastic such as polycarbonate to alleviate any friction that may occur between the end cap portion 46*a* and the trocar. The rotation knob 48 may comprise "scallops" or flutes formed of raised ribs 48*a* and concave portions 48*b* located between the ribs 48*a* to provide a more precise rotational grip. In one example embodiment, the rotation knob 48 may comprise a plurality of flutes (e.g., three or more flutes). In other embodiments, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example embodiment, the handle assembly 12 is formed from two (2) housing portions or shrouds comprising a first portion 12*a* and a second portion 12*b*. From the perspective of a user viewing the handle assembly 12 from the distal end towards the proximal end, the first portion 12*a* is considered the right portion and the second portion 12*b* is considered the left portion. Each of the first and second portions 12*a*, 12*b* includes a plurality of interfaces 69 (FIG. 5) dimensioned to mechanically align and engage each another to form the handle assembly 12 and enclosing the internal working components thereof. The fixed handle 34, which is integrally associated with the handle assembly 12, takes shape upon the assembly of the first and second portions 12*a* and 12*b* of the handle assembly 12. A plurality of additional interfaces (not shown) may be disposed at various points around the periphery of the first and second portions 12*a* and 12*b* of the handle assembly 12 for ultrasonic welding purposes, e.g., energy direction/deflection points. The first and second portions 12*a* and 12*b* (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example embodiment, the elongated shaft assembly 14 comprises a proximal end 50 adapted to mechanically engage the handle assembly 12 and the distal rotation assembly 13; and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated embodiment, the distal end of the tubular reciprocating tubular actuating member 58 is mechanically engaged to a clamp arm assembly 64, which is pivotable about a pivot point 70, to open and close the clamp arm assembly 64 in response to the actuation and/or release of the trigger 32. For example, in the illustrated embodiment, the clamp arm assembly 64 is movable in direction 62A from an open position to a closed position about a pivot point 70 when the trigger 32 is squeezed in direction 33A. The clamp arm assembly 64 is movable in direction 62B from a closed position to an open position about the pivot point 70 when the trigger 32 is released or outwardly contacted in direction 33B.

In one example embodiment, the end effector assembly 26 is attached at the distal end 52 of the elongated shaft assembly 14 and includes a clamp arm assembly 64 and a blade 66. The jaws of the clamping mechanism of the end effector assembly 26 are formed by clamp arm assembly 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33A moves the clamp arm assembly 64 in direction 62A from an open position, wherein the clamp arm assembly 64 and the blade 66 are disposed in a spaced relation relative to one another, to a clamped or closed position, wherein the clamp arm assembly 64 and the blade 66 cooperate to grasp tissue therebetween. The clamp arm assembly 64 may comprise a clamp pad 69 to engage tissue between the blade 66 and the clamp arm 64. Releasing the trigger 32 in direction 33B moves the clamp arm assembly 64 in direction 62B from a closed relationship, to an open position, wherein the clamp arm assembly 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

In one example embodiment, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33B to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 36 to activate the end effector assembly 26. The shorter span and rotation travel creates a more comfortable grip when closing or squeezing the trigger 32 in direction 33A or when opening the trigger 32 in the outward opening motion in direction 33B lessening the need to extend the fingers further outward. This substantially lessens hand fatigue and strain associated with the outward opening motion of the trigger 32 in direction 33B. The outward opening motion of the trigger may be spring-assisted by spring element 98 (FIG. 5) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user the may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

Figure 3:
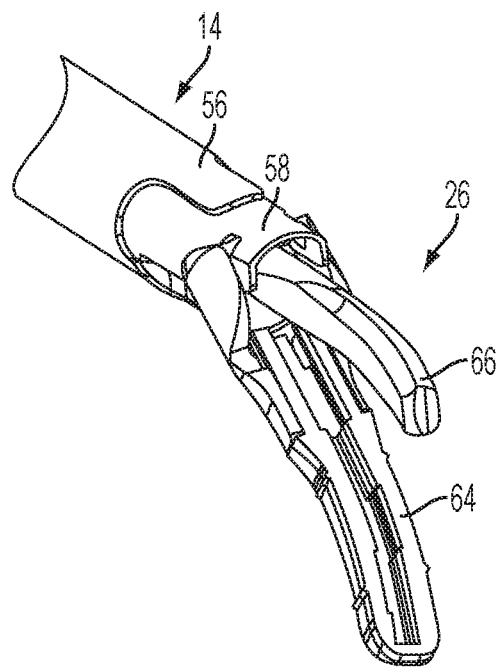
FIG. 3 illustrates one embodiment of an ultrasonic end effector.
Figure 4:
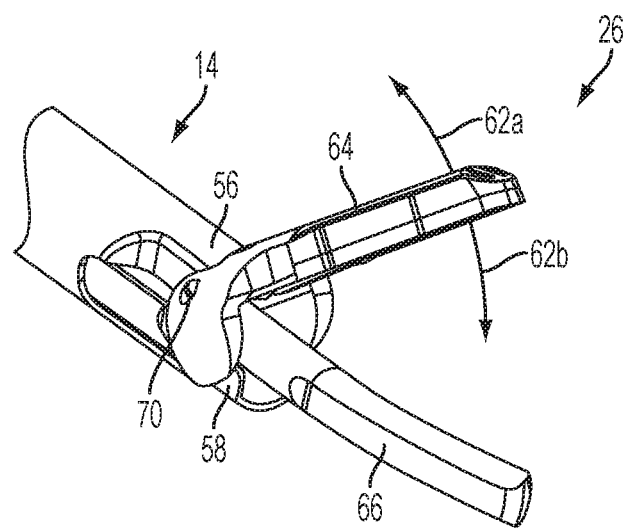
FIG. 4 illustrates another embodiment of an ultrasonic end effector.

FIGS. 3-4 illustrate the connection of the elongated shaft assembly 14 relative to the end effector assembly 26. As previously described, in the illustrated embodiment, the end effector assembly 26 comprises a clamp arm assembly 64 and a blade 66 to form the jaws of the clamping mechanism. The blade 66 may be an ultrasonically actuatable blade acoustically coupled to the ultrasonic transducer 16. The trigger 32 is mechanically connected to a drive assembly. Together, the trigger 32 and the drive assembly mechanically cooperate to move the clamp arm assembly 64 to an open position in direction 62A wherein the clamp arm assembly 64 and the blade 66 are disposed in spaced relation relative to one another, to a clamped or closed position in direction 62B wherein the clamp arm assembly 64 and the blade 66 cooperate to grasp tissue therebetween. The clamp arm assembly 64 may comprise a clamp pad 69 to engage tissue between the blade 66 and the clamp arm 64. The distal end of the tubular reciprocating tubular actuating member 58 is mechanically engaged to the end effector assembly 26. In the illustrated embodiment, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated embodiment, the clamp arm assembly 64 is movable from an open position to a closed position in direction 62B about a pivot point 70 when the trigger 32 is squeezed in direction 33A. The clamp arm assembly 64 is movable from a closed position to an open position in direction 62A about the pivot point 70 when the trigger 32 is released or outwardly contacted in direction 33B.

As previously discussed, the clamp arm assembly 64 may comprise electrodes electrically coupled to the electrosurgical/RF generator module 23 to receive therapeutic and/or sub-therapeutic energy, where the electrosurgical/RF energy may be applied to the electrodes either simultaneously or non-simultaneously with the ultrasonic energy being applied to the blade 66. Such energy activations may be applied in any suitable combinations to achieve a desired tissue effect in cooperation with an algorithm or other control logic.

Figure 5:
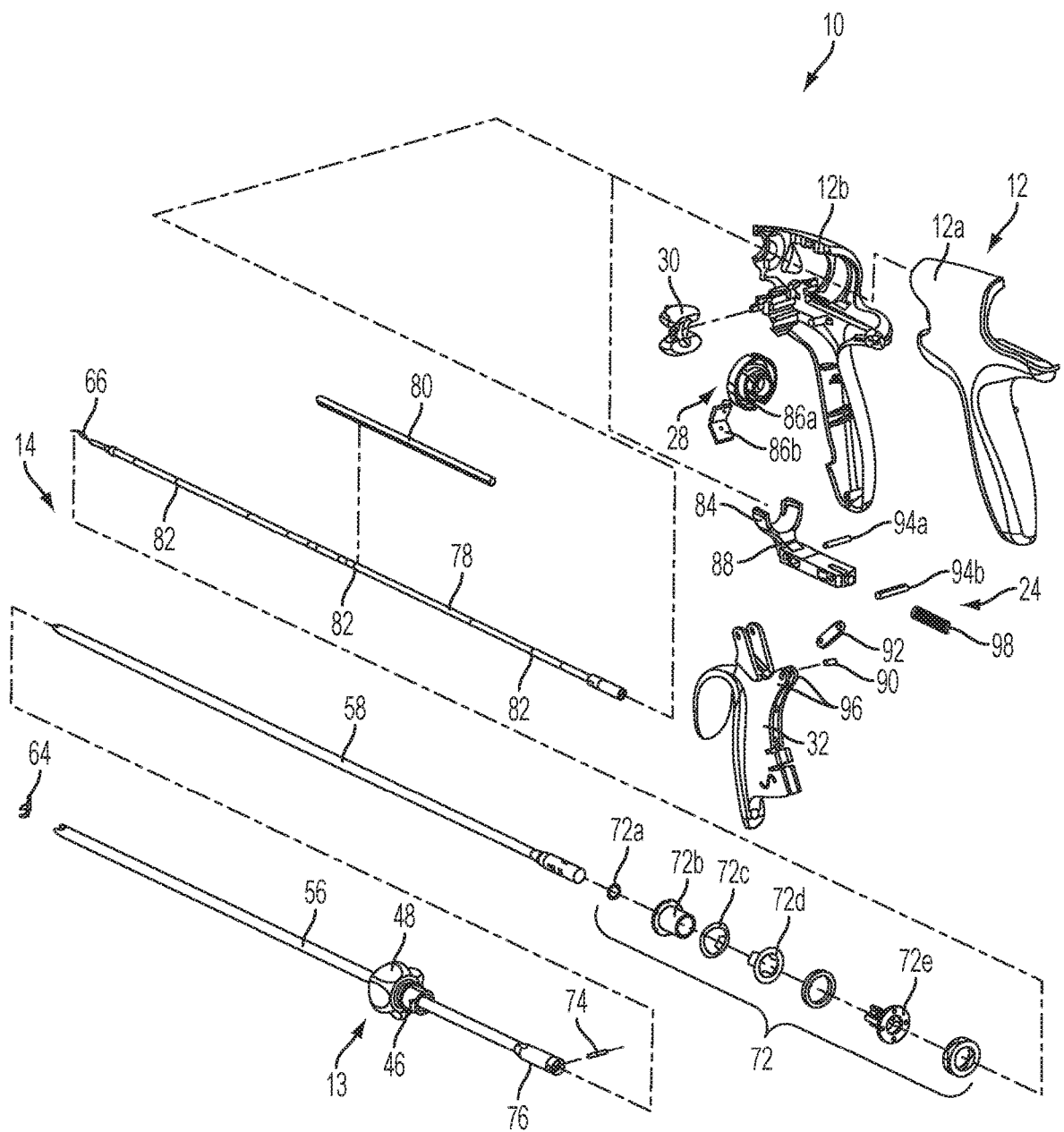
FIG. 5 illustrates an exploded view of one embodiment of the surgical instrument shown in FIG. 1.
Figure 7:
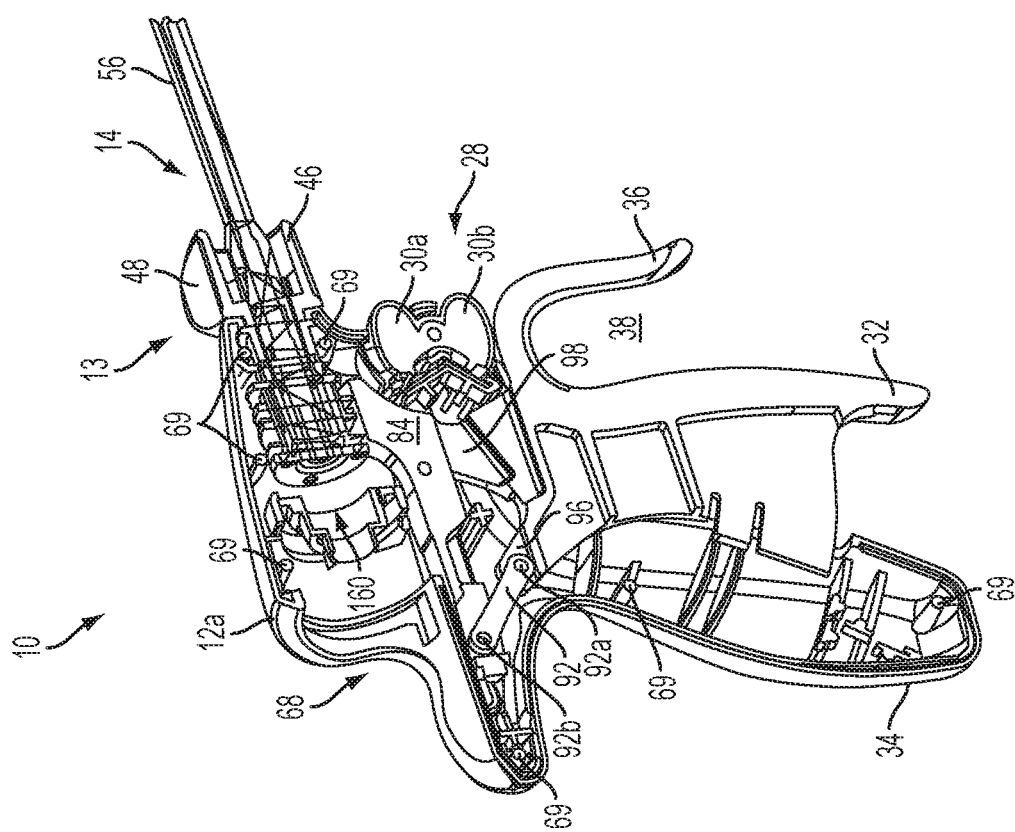
FIG. 7 illustrates various internal components of one example embodiment of the surgical instrument shown in FIG. 1
Figure 6:
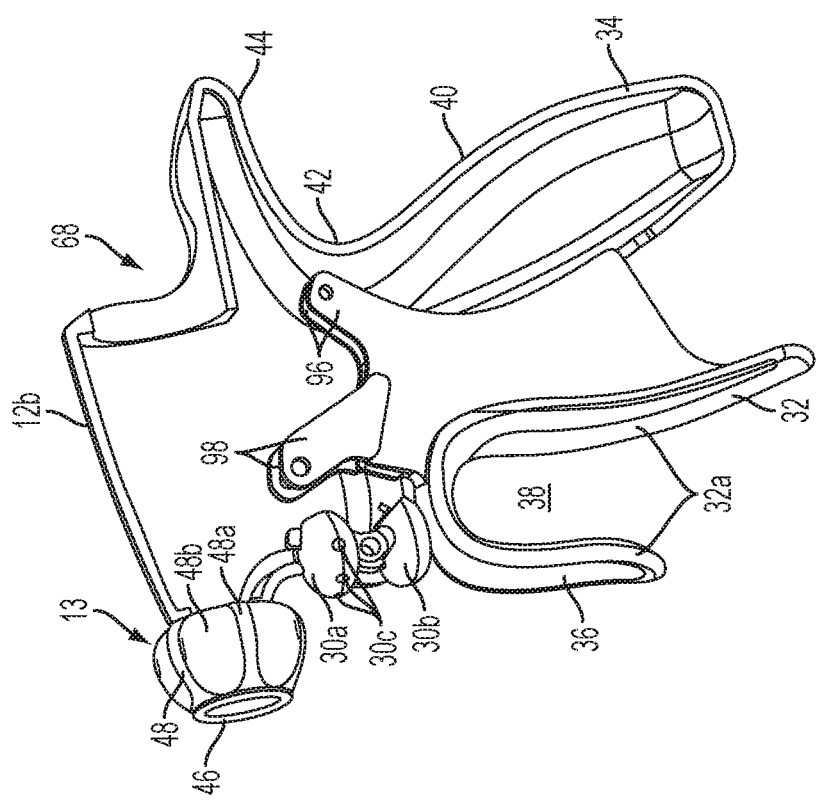
FIG. 6 illustrates a cut-away view of one embodiment of the surgical instrument shown in FIG. 1.

FIG. 5 is an exploded view of the ultrasonic surgical instrument 10 shown in FIG. 2. In the illustrated embodiment, the exploded view shows the internal elements of the handle assembly 12, the handle assembly 12, the distal rotation assembly 13, the switch assembly 28, and the elongated shaft assembly 14. In the illustrated embodiment, the first and second portions 12a, 12b mate to form the handle assembly 12. The first and second portions 12a, 12b each comprises a plurality of interfaces 69 dimensioned to mechanically align and engage one another to form the handle assembly 12 and enclose the internal working components of the ultrasonic surgical instrument 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an O-ring 72a, a tube collar cap 72b, a distal washer 72c, a proximal washer 72d, and a thread tube collar 72e. The reciprocating tubular actuating member 58 is located within a reciprocating yoke 84, which is retained between the first and second portions 12a, 12b of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical instrument 10. In one example embodiment, a four-link design provides mechanical advantage in a relatively short rotation span, for example.

In one example embodiment, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16 as discussed in more detail below. The ultrasonic transmission waveguide 78 is isolated from the other elements of the elongated shaft assembly 14 by a protective sheath 80 and a plurality of isolation elements 82, such as silicone rings. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86a,b to electrically energize the ultrasonic transducer 16 in accordance with the activation of the first or second projecting knobs 30a, 30b.

In one example embodiment, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 24 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 may allow the assembly to be torqued to a required level. In one example embodiment, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example embodiment, the distal end of the ultrasonic transmission waveguide 78 may be coupled to the proximal end of the blade 66 by an internal threaded connection, preferably at or near an antinode. It is contemplated that the blade 66 may be attached to the ultrasonic transmission waveguide 78 by any suitable means, such as a welded joint or the like. Although the blade 66 may be detachable from the ultrasonic transmission waveguide 78, it is also contemplated that the single element end effector (e.g., the blade 66) and the ultrasonic transmission waveguide 78 may be formed as a single unitary piece.

In one example embodiment, the trigger 32 is coupled to a linkage mechanism to translate the rotational motion of the trigger 32 in directions 33A and 33B to the linear motion of the reciprocating tubular actuating member 58 in corresponding directions 60A and 60B. The trigger 32 comprises a first set of flanges 98 with openings formed therein to receive a first yoke pin 92a. The first yoke pin 92a is also located through a set of openings formed at the distal end of the yoke 84. The trigger 32 also comprises a second set of flanges 96 to receive a first end 92a of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12a, 12b of the handle assembly 12 to form a trigger pivot point for the trigger 32. A second end 92b of the link 92 is received in a slot 384 formed in a proximal end of the yoke 84 and is retained therein by a second yoke pin 94b. As the trigger 32 is pivotally rotated about the pivot point 190 formed by the trigger pin 90, the yoke translates horizontally along longitudinal axis "T" in a direction indicated by arrows 60A,B.

Figure 8:
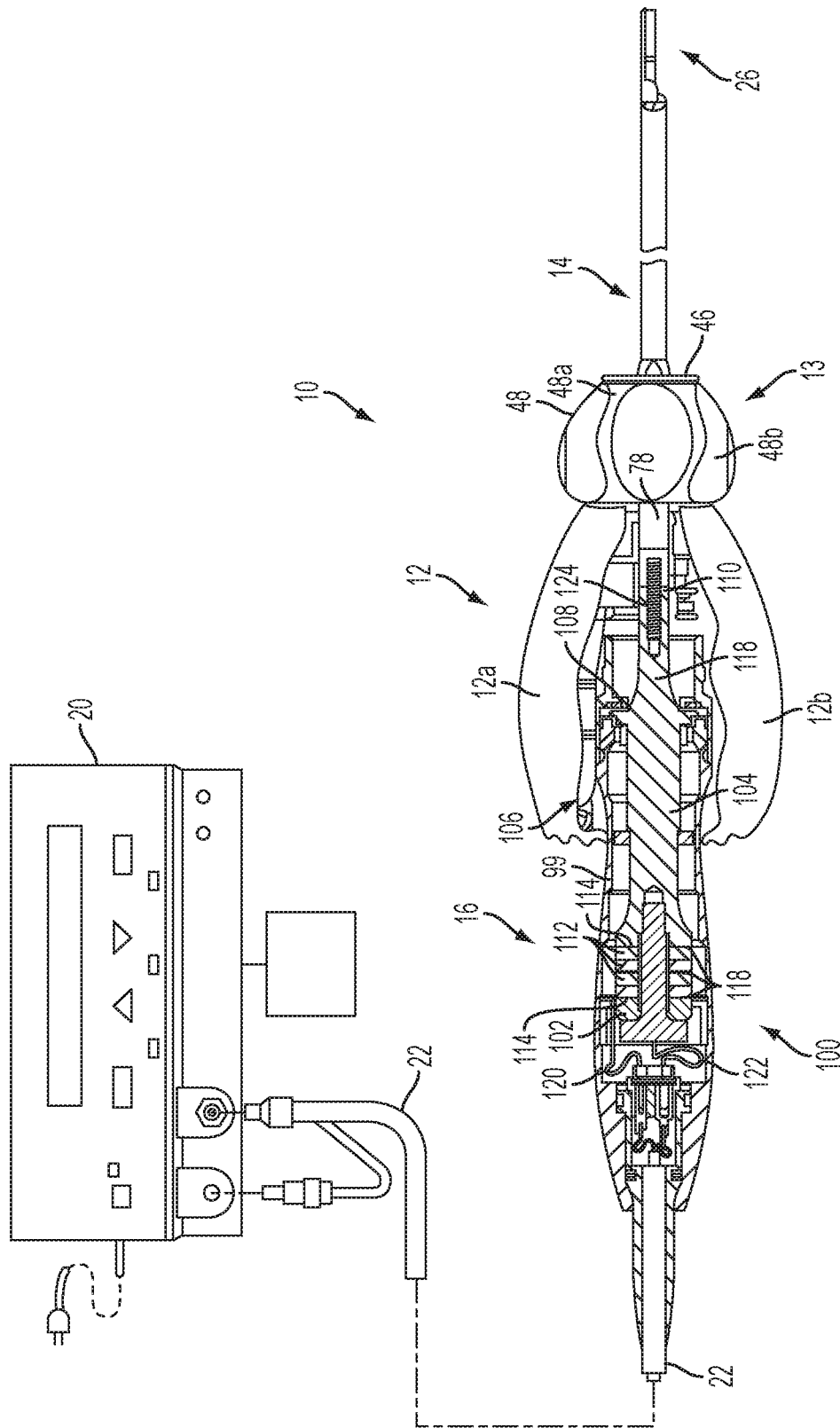
FIG. 8 illustrates a top view of one embodiment of a surgical system including a surgical instrument and an ultrasonic generator.

FIG. 8 illustrates one example embodiment of an ultrasonic surgical instrument 10. In the illustrated embodiment, a cross-sectional view of the ultrasonic transducer 16 is shown within a partial cutaway view of the handle assembly 12. One example embodiment of the ultrasonic surgical instrument 10 comprises the ultrasonic signal generator 20 coupled to the ultrasonic transducer 16, comprising a hand piece housing 99, and an ultrasonically actuatable single or multiple element end effector assembly 26. As previously discussed, the end effector assembly 26 comprises the ultrasonically actuatable blade 66 and the clamp arm 64. The ultrasonic transducer 16, which is known as a "Langevin stack", generally includes a transduction portion 100, a first resonator portion or end-bell 102, and a second resonator portion or fore-bell 104, and ancillary components. The total construction of these components is a resonator. The ultrasonic transducer 16 is preferably an integral number of one-half system wavelengths ($n\lambda/2$; where "n" is any positive integer; e.g., n=1, 2, 3 . . . ) in length as will be described in more detail later. An acoustic assembly 106 includes the ultrasonic transducer 16, a nose cone 108, a velocity transformer 118, and a surface 110.

In one example embodiment, the distal end of the end-bell 102 is connected to the proximal end of the transduction portion 100, and the proximal end of the fore-bell 104 is connected to the distal end of the transduction portion 100. The fore-bell 104 and the end-bell 102 have a length determined by a number of variables, including the thickness of the transduction portion 100, the density and modulus of elasticity of the material used to manufacture the end-bell 102 and the fore-bell 22, and the resonant frequency of the ultrasonic transducer 16. The fore-bell 104 may be tapered inwardly from its proximal end to its distal end to amplify the ultrasonic vibration amplitude as the velocity transformer 118, or alternately may have no amplification. A suitable vibrational frequency range may be about 20 Hz to 32 kHz and a well-suited vibrational frequency range may be about 30-10 kHz. A suitable operational vibrational frequency may be approximately 55.5 kHz, for example.

In one example embodiment, the piezoelectric elements 112 may be fabricated from any suitable material, such as, for example, lead zirconate-titanate, lead meta-niobate, lead titanate, barium titanate, or other piezoelectric ceramic material. Each of positive electrodes 114, negative electrodes 116, and the piezoelectric elements 112 has a bore extending through the center. The positive and negative electrodes 114 and 116 are electrically coupled to wires 120 and 122, respectively. The wires 120 and 122 are encased within the cable 22 and electrically connectable to the ultrasonic signal generator 20.

The ultrasonic transducer 16 of the acoustic assembly 106 converts the electrical signal from the ultrasonic signal generator 20 into mechanical energy that results in primarily a standing acoustic wave of longitudinal vibratory motion of the ultrasonic transducer 16 and the blade 66 portion of the end effector assembly 26 at ultrasonic frequencies. In another embodiment, the vibratory motion of the ultrasonic transducer may act in a different direction. For example, the vibratory motion may comprise a local longitudinal component of a more complicated motion of the tip of the elongated shaft assembly 14. A suitable generator is available as model number GEN11, from Ethicon Endo-Surgery, Inc., Cincinnati, Ohio. When the acoustic assembly 106 is energized, a vibratory motion standing wave is generated through the acoustic assembly 106. The ultrasonic surgical instrument 10 is designed to operate at a resonance such that an acoustic standing wave pattern of predetermined amplitude is produced. The amplitude of the vibratory motion at any point along the acoustic assembly 106 depends upon the location along the acoustic assembly 106 at which the vibratory motion is measured. A minimum or zero crossing in the vibratory motion standing wave is generally referred to as a node (i.e., where motion is minimal), and a local absolute value maximum or peak in the standing wave is generally referred to as an anti-node (e.g., where local motion is maximal). The distance between an anti-node and its nearest node is one-quarter wavelength ($\lambda/4$).

The wires 120 and 122 transmit an electrical signal from the ultrasonic signal generator 20 to the positive electrodes 114 and the negative electrodes 116. The piezoelectric elements 112 are energized by the electrical signal supplied from the ultrasonic signal generator 20 in response to an actuator 224, such as a foot switch, for example, to produce an acoustic standing wave in the acoustic assembly 106. The electrical signal causes disturbances in the piezoelectric elements 112 in the form of repeated small displacements resulting in large alternating compression and tension forces within the material. The repeated small displacements cause the piezoelectric elements 112 to expand and contract in a continuous manner along the axis of the voltage gradient, producing longitudinal waves of ultrasonic energy. The ultrasonic energy is transmitted through the acoustic assembly 106 to the blade 66 portion of the end effector assembly 26 via a transmission component or an ultrasonic transmission waveguide portion 78 of the elongated shaft assembly 14.

In one example embodiment, in order for the acoustic assembly 106 to deliver energy to the blade 66 portion of the end effector assembly 26, all components of the acoustic assembly 106 must be acoustically coupled to the blade 66. The distal end of the ultrasonic transducer 16 may be acoustically coupled at the surface 110 to the proximal end of the ultrasonic transmission waveguide 78 by a threaded connection such as a stud 124.

In one example embodiment, the components of the acoustic assembly 106 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 106. It is also contemplated that the acoustic assembly 106 may incorporate any suitable arrangement of acoustic elements.

In one example embodiment, the blade 66 may have a length substantially equal to an integral multiple of one-half system wavelengths ($n\lambda/2$). A distal end of the blade 66 may be disposed near an antinode in order to provide the maximum longitudinal excursion of the distal end. When the transducer assembly is energized, the distal end of the blade 66 may be configured to move in the range of, for example, approximately 10 to 500 microns peak-to-peak, and preferably in the range of about 30 to 64 microns at a predetermined vibrational frequency of 55 kHz, for example.

In one example embodiment, the blade 66 may be coupled to the ultrasonic transmission waveguide 78. The blade 66 and the ultrasonic transmission waveguide 78 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the blade 66 may be separable (and of differing composition) from the ultrasonic transmission waveguide 78, and coupled by, for example, a stud, weld, glue, quick connect, or other suitable known methods. The length of the ultrasonic transmission waveguide 78 may be substantially equal to an integral number of one-half wavelengths ($n\lambda/2$), for example. The ultrasonic transmission waveguide 78 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

In one example embodiment, the ultrasonic transmission waveguide 78 comprises a longitudinally projecting attachment post at a proximal end to couple to the surface 110 of the ultrasonic transmission waveguide 78 by a threaded connection such as the stud 124. The ultrasonic transmission waveguide 78 may include a plurality of stabilizing silicone rings or compliant supports 82 (FIG. 5) positioned at a plurality of nodes. The silicone rings 82 dampen undesirable vibration and isolate the ultrasonic energy from an outer protective sheath 80 (FIG. 5) assuring the flow of ultrasonic energy in a longitudinal direction to the distal end of the blade 66 with maximum efficiency.

Figure 9:
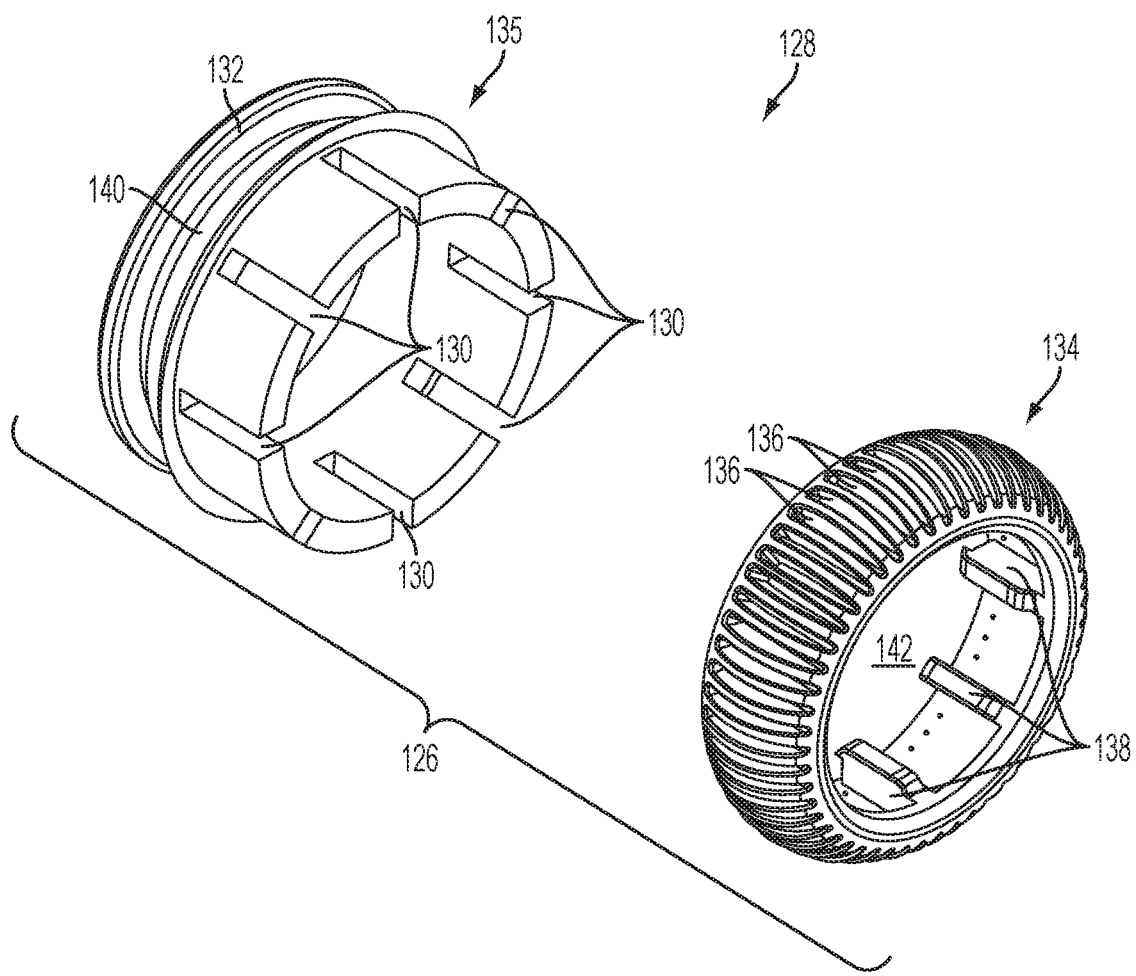
FIG. 9 illustrates one embodiment of a rotation assembly included in one example embodiment of the surgical instrument of FIG. 1.

FIG. 9 illustrates one example embodiment of the proximal rotation assembly 128. In the illustrated embodiment, the proximal rotation assembly 128 comprises the proximal rotation knob 134 inserted over the cylindrical hub 135. The proximal rotation knob 134 comprises a plurality of radial projections 138 that are received in corresponding slots 130 formed on a proximal end of the cylindrical hub 135. The proximal rotation knob 134 defines an opening 142 to receive the distal end of the ultrasonic transducer 16. The radial projections 138 are formed of a soft polymeric material and define a diameter that is undersized relative to the outside diameter of the ultrasonic transducer 16 to create a friction interference fit when the distal end of the ultrasonic transducer 16. The polymeric radial projections 138 protrude radially into the opening 142 to form "gripper" ribs that firmly grip the exterior housing of the ultrasonic transducer 16. Therefore, the proximal rotation knob 134 securely grips the ultrasonic transducer 16.

The distal end of the cylindrical hub 135 comprises a circumferential lip 132 and a circumferential bearing surface 140. The circumferential lip engages a groove formed in the housing 12 and the circumferential bearing surface 140 engages the housing 12. Thus, the cylindrical hub 135 is mechanically retained within the two housing portions (not shown) of the housing 12. The circumferential lip 132 of the cylindrical hub 135 is located or "trapped" between the first and second housing portions 12a, 12b and is free to rotate in place within the groove. The circumferential bearing surface 140 bears against interior portions of the housing to assist proper rotation. Thus, the cylindrical hub 135 is free to rotate in place within the housing. The user engages the flutes 136 formed on the proximal rotation knob 134 with either the finger or the thumb to rotate the cylindrical hub 135 within the housing 12.

In one example embodiment, the cylindrical hub 135 may be formed of a durable plastic such as polycarbonate. In one example embodiment, the cylindrical hub 135 may be formed of a siliconized polycarbonate material. In one example embodiment, the proximal rotation knob 134 may be formed of pliable, resilient, flexible polymeric materials including Versaflex® TPE alloys made by GLS Corporation, for example. The proximal rotation knob 134 may be formed of elastomeric materials, thermoplastic rubber known as Santoprene®, other thermoplastic vulcanizates (TPVs), or elastomers, for example. The embodiments, however, are not limited in this context.

Figure 10:
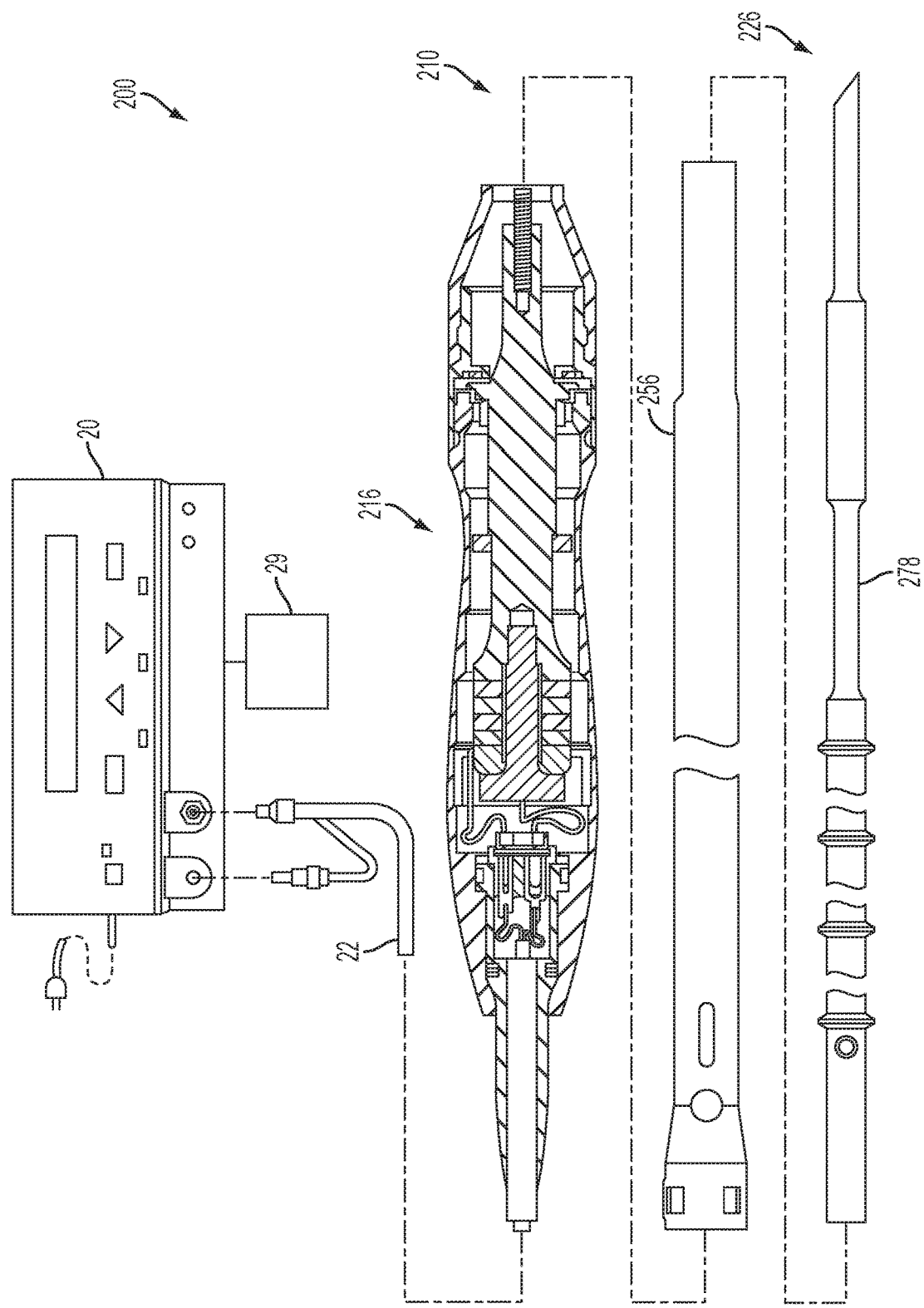
FIG. 10 illustrates one embodiment of a surgical system including a surgical instrument having a single element end effector.

FIG. 10 illustrates one example embodiment of a surgical system 200 including a surgical instrument 210 having single element end effector 278. The system 200 may include a transducer assembly 216 coupled to the end effector 278 and a sheath 256 positioned around the proximal portions of the end effector 278 as shown. The transducer assembly 216 and end effector 278 may operate in a manner similar to that of the transducer assembly 16 and end effector 18 described above to produce ultrasonic energy that may be transmitted to tissue via blade 226'.

Figure 11:
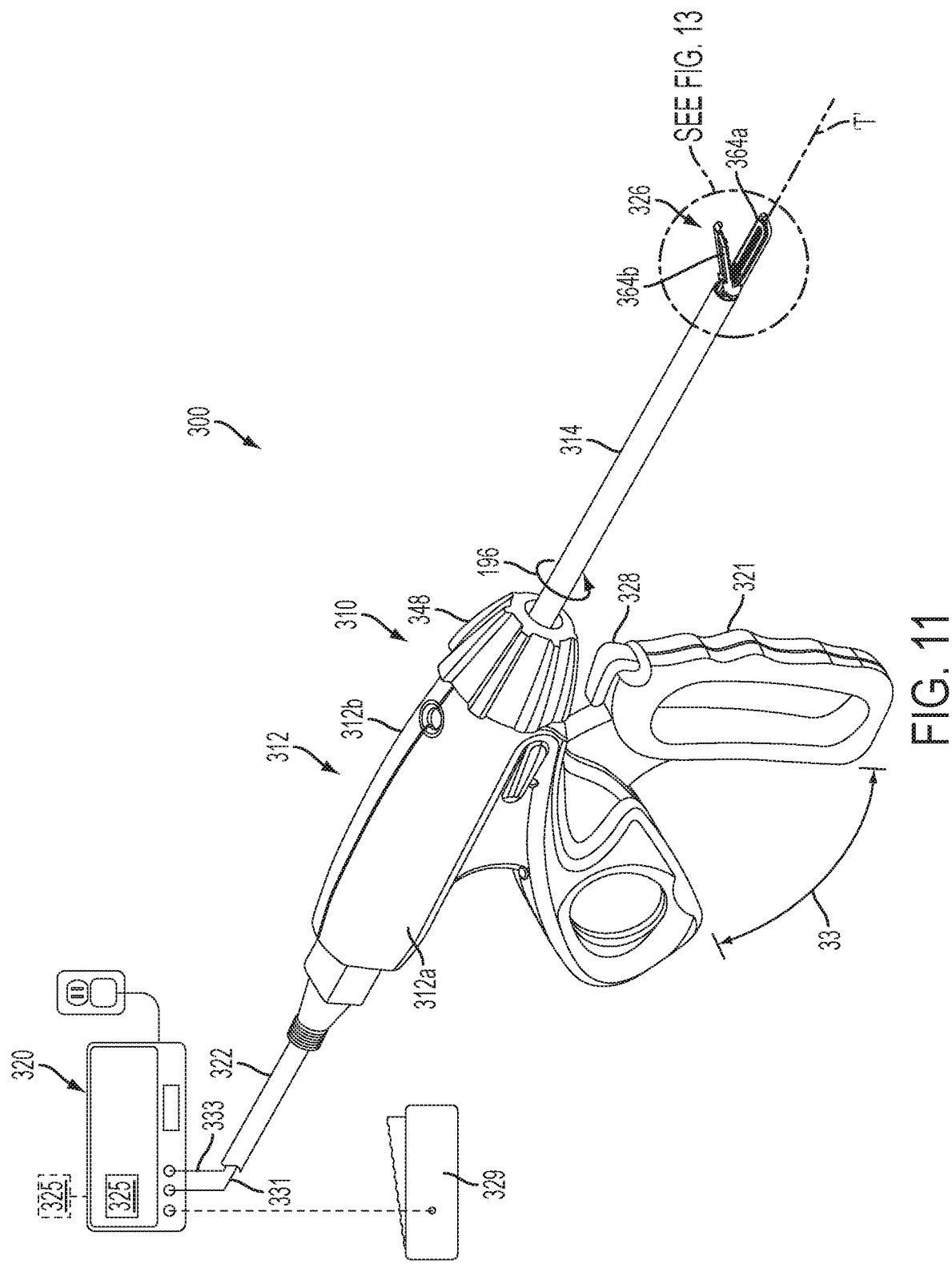
FIG. 11 is a perspective view of one embodiment of an electrical energy surgical instrument.

FIGS. 11-18C illustrate various embodiments of surgical instruments that utilize therapeutic and/or sub-therapeutic electrical energy to treat and/or destroy tissue or provide feedback to the generators (e.g., electrosurgical instruments). The embodiments of FIGS. 11-18C are adapted for use in a manual or hand-operated manner, although electrosurgical instruments may be utilized in robotic applications as well. FIG. 11 is a perspective view of one example embodiment of a surgical instrument system 300 comprising an electrical energy surgical instrument 310. The electrosurgical instrument 310 may comprise a proximal handle 312, a distal working end or end effector 326 and an introducer or elongated shaft 314 disposed in-between.

The electrosurgical system 300 can be configured to supply energy, such as electrical energy, ultrasonic energy, heat energy or any combination thereof, for, to the tissue of a patient either independently or simultaneously as described, for example, in connection with FIG. 1, for example. In one example embodiment, the electrosurgical system 300 includes a generator 320 in electrical communication with the electrosurgical instrument 310. The generator 320 is connected to electrosurgical instrument 310 via a suitable transmission medium such as a cable 322. In one example embodiment, the generator 320 is coupled to a controller, such as a control unit 325, for example. In various embodiments, the control unit 325 may be formed integrally with the generator 320 or may be provided as a separate circuit module or device electrically coupled to the generator 320 (shown in phantom to illustrate this option). Although in the presently disclosed embodiment, the generator 320 is shown separate from the electrosurgical instrument 310, in one example embodiment, the generator 320 (and/or the control unit 325) may be formed integrally with the electrosurgical instrument 310 to form a unitary electrosurgical system 300, where a battery located within the electrosurgical instrument 310 is the energy source and a circuit coupled to the battery produces the suitable electrical energy, ultrasonic energy, or heat energy. One such example is described herein below in connection with FIGS. 17-18C.

The generator 320 may comprise an input device 335 located on a front panel of the generator 320 console. The input device 335 may comprise any suitable device that generates signals suitable for programming the operation of the generator 320, such as a keyboard, or input port, for example. In one example embodiment, various electrodes in the first jaw 364A and the second jaw 364B may be coupled to the generator 320. The cable 322 may comprise multiple electrical conductors for the application of electrical energy to positive (+) and negative (−) electrodes of the electrosurgical instrument 310. The control unit 325 may be used to activate the generator 320, which may serve as an electrical source. In various embodiments, the generator 320 may comprise an RF source, an ultrasonic source, a direct current source, and/or any other suitable type of electrical energy source, for example, which may be activated independently or simultaneously.

In various embodiments, the electrosurgical system 300 may comprise at least one supply conductor 331 and at least one return conductor 333, wherein current can be supplied to electrosurgical instrument 300 via the supply conductor 331 and wherein the current can flow back to the generator 320 via return conductor 333. In various embodiments, the supply conductor 331 and the return conductor 333 may comprise insulated wires and/or any other suitable type of conductor. In certain embodiments, as described below, the supply conductor 331 and the return conductor 333 may be contained within and/or may comprise the cable 322 extending between, or at least partially between, the generator 320 and the end effector 326 of the electrosurgical instrument 310. In any event, the generator 320 can be configured to apply a sufficient voltage differential between the supply conductor 331 and the return conductor 333 such that sufficient current can be supplied to the end effector 110.

Figure 12:
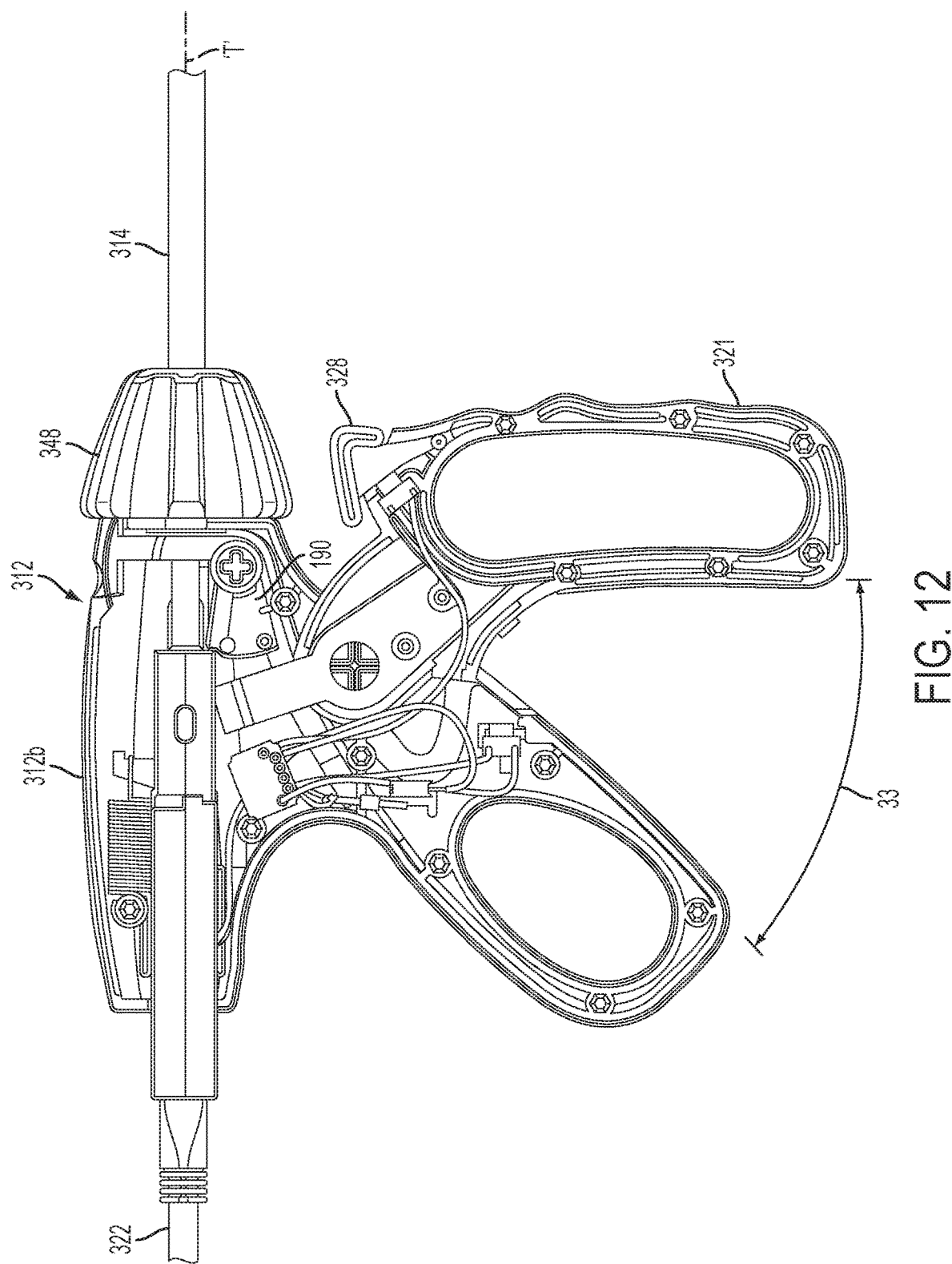
FIG. 12 is a side view of a handle of one embodiment of the surgical instrument of FIG. 11 with a half of a handle body removed to illustrate some of the components therein.

FIG. 12 is a side view of one example embodiment of the handle 312 of the surgical instrument 310. In FIG. 12, the handle 312 is shown with half of a first handle body 312A (see FIG. 11) removed to illustrate various components within second handle body 312B. The handle 312 may comprise a lever arm 321 (e.g., a trigger) which may be pulled along a path 33. The lever arm 321 may be coupled to an axially moveable member 378 (FIGS. 13-16) disposed within elongated shaft 314 by a shuttle 384 operably engaged to an extension 398 of lever arm 321. The shuttle 384 may further be connected to a biasing device, such as a spring 388, which may also be connected to the second handle body 312B, to bias the shuttle 384 and thus the axially moveable member 378 in a proximal direction, thereby urging the jaws 364A and 364B to an open position as seen in FIG. 11. Also, referring to FIGS. 11-12, a locking member 190 (see FIG. 12) may be moved by a locking switch 328 (see FIG. 11) between a locked position, where the shuttle 384 is substantially prevented from moving distally as illustrated, and an unlocked position, where the shuttle 384 may be allowed to freely move in the distal direction, toward the elongated shaft 314. The handle 312 can be any type of pistol-grip or other type of handle known in the art that is configured to carry actuator levers, triggers or sliders for actuating the first jaw 364A and the second jaw 364B. The elongated shaft 314 may have a cylindrical or rectangular cross-section, for example, and can comprise a thin-wall tubular sleeve that extends from handle 312. The elongated shaft 314 may include a bore extending therethrough for carrying actuator mechanisms, for example, the axially moveable member 378, for actuating the jaws and for carrying electrical leads for delivery of electrical energy to electrosurgical components of the end effector 326.

The end effector 326 may be adapted for capturing and transecting tissue and for the contemporaneously welding the captured tissue with controlled application of energy (e.g., RF energy). The first jaw 364A and the second jaw 364B may close to thereby capture or engage tissue about a longitudinal axis "T" defined by the axially moveable member 378. The first jaw 364A and second jaw 364B may also apply compression to the tissue. In some embodiments, the elongated shaft 314, along with first jaw 364A and second jaw 364B, can be rotated a full 360° degrees, as shown by arrow 196 (see FIG. 11), relative to handle 312. For example, a rotation knob 348 may be rotatable about the longitudinal axis of the shaft 314 and may be coupled to the shaft 314 such that rotation of the knob 348 causes corresponding rotation of the shaft 314. The first jaw 364A and the second jaw 364B can remain openable and/or closeable while rotated.

Figure 13:
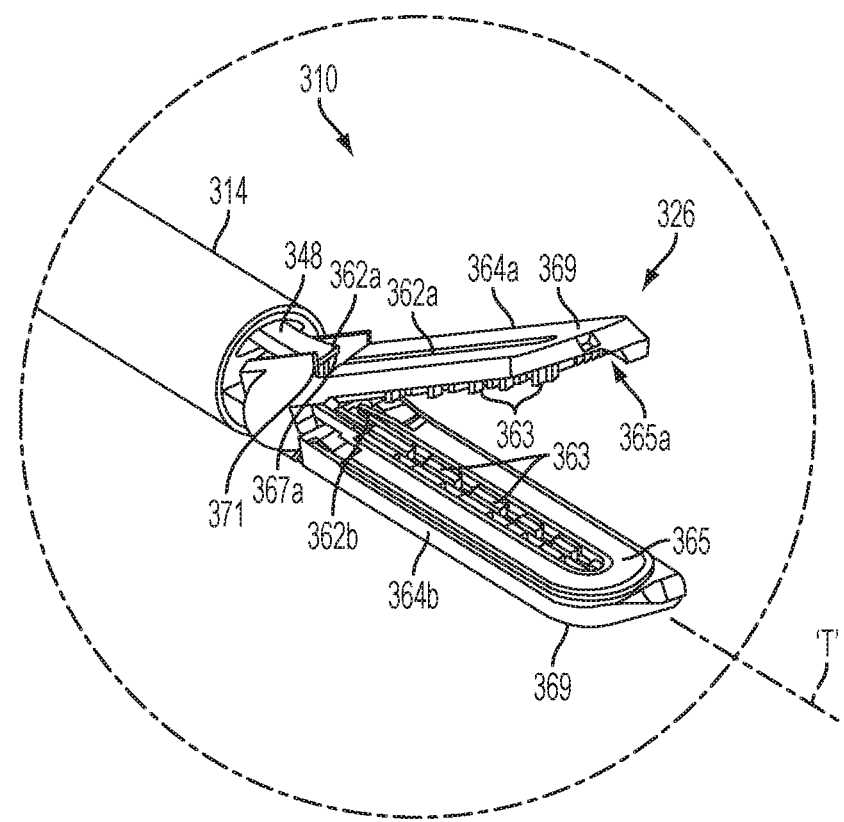
FIG. 13 illustrates a perspective view of one embodiment of the end effector of the surgical instrument of FIG. 11 with the jaws open and the distal end of an axially movable member in a retracted position.
Figure 14:
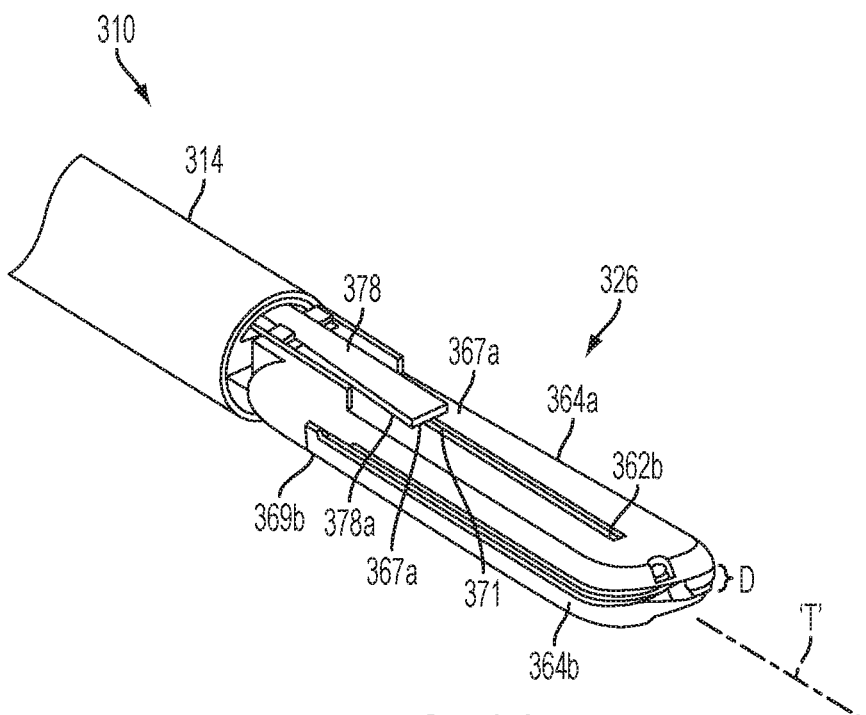
FIG. 14 illustrates a perspective view of one embodiment of the end effector of the surgical instrument of FIG. 11 with the jaws closed and the distal end of an axially movable member in a partially advanced position.

FIG. 13 shows a perspective view of one example embodiment of the end effector 326 with the jaws 364A, 364B open, while FIG. 14 shows a perspective view of one example embodiment of the end effector 326 with the jaws 364A, 364B closed. As noted above, the end effector 326 may comprise the upper first jaw 364A and the lower second jaw 364B, which may be straight or curved. The first jaw 364A and the second jaw 364B may each comprise an elongated slot or channel 362A and 362B, respectively, disposed outwardly along their respective middle portions. Further, the first jaw 364A and second jaw 364B may each have tissue-gripping elements, such as teeth 363, disposed on the inner portions of first jaw 364A and second jaw 364B. The first jaw 364A may comprise an upper first jaw body 200A with an upper first outward-facing surface 202A and an upper first energy delivery surface 365A. The second jaw 364B may comprise a lower second jaw body 200B with a lower second outward-facing surface 202B and a lower second energy delivery surface 365B. The first energy delivery surface 365A and the second energy delivery surface 365B may both extend in a "U" shape about the distal end of the end effector 326.

The lever arm 321 of the handle 312 (FIG. 12) may be adapted to actuate the axially moveable member 378, which may also function as a jaw-closing mechanism. For example, the axially moveable member 378 may be urged distally as the lever arm 321 is pulled proximally along the path 33 via the shuttle 384, as shown in FIG. 12 and discussed above.

Figure 15:
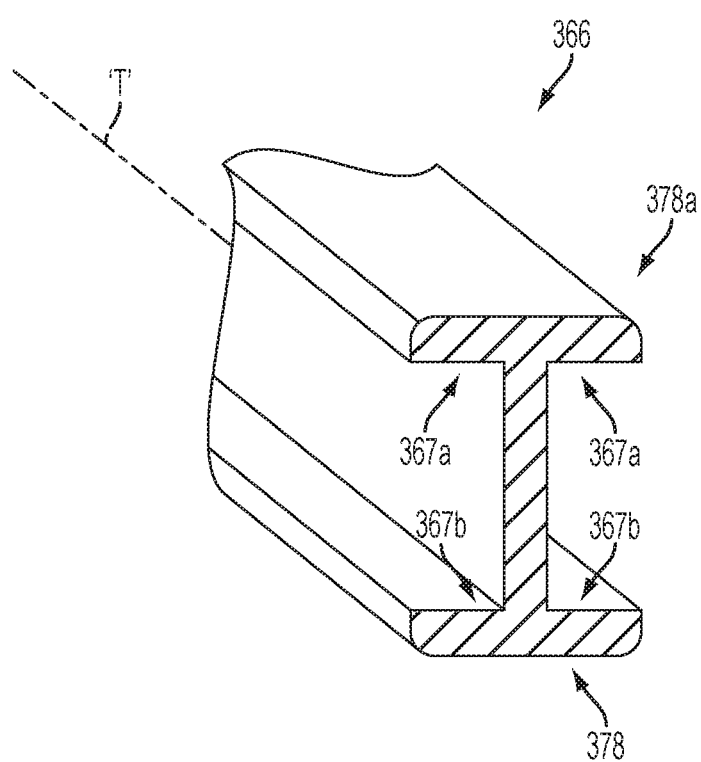
FIG. 15 illustrates a perspective view of one embodiment of the axially moveable member of the surgical instrument of FIG. 11.

FIG. 15 is a perspective view of one example embodiment of the axially moveable member 378 of the surgical instrument 310. The axially moveable member 378 may comprise one or several pieces, but in any event, may be movable or translatable with respect to the elongated shaft 314 and/or the jaws 364A, 364B. Also, in at least one example embodiment, the axially moveable member 378 may be made of 17-4 precipitation hardened stainless steel. The distal end of axially moveable member 378 may comprise a flanged "I"-beam configured to slide within the channels 362A and 362B in jaws 364A and 364B. The axially moveable member 378 may slide within the channels 362A, 362B to open and close first jaw 364A and second jaw 364B. The distal end of the axially moveable member 378 may also comprise an upper flange or "c"-shaped portion 378A and a lower flange or "c"-shaped portion 378B. The flanges 378A and 378B respectively define inner cam surfaces 367A and 367B for engaging outward facing surfaces of the first jaw 364A and the second jaw 364B. The opening-closing of jaws 364A and 364B can apply very high compressive forces on tissue using cam mechanisms which may include movable "I-beam" axially moveable member 378 and the outward facing surfaces 369A, 369B of jaws 364A, 364B.

More specifically, referring now to FIGS. 13-15, collectively, the inner cam surfaces 367A and 367B of the distal end of axially moveable member 378 may be adapted to slidably engage the first outward-facing surface 369A and the second outward-facing surface 369B of the first jaw 364A and the second jaw 364B, respectively. The channel 362A within first jaw 364A and the channel 362B within the second jaw 364B may be sized and configured to accommodate the movement of the axially moveable member 378, which may comprise a tissue-cutting element 371, for example, comprising a sharp distal edge. FIG. 14, for example, shows the distal end of the axially moveable member 378 advanced at least partially through channels 362A and 362B (FIG. 13). The advancement of the axially moveable member 378 may close the end effector 326 from the open configuration shown in FIG. 13. In the closed position shown by FIG. 14, the upper first jaw 364A and lower second jaw 364B define a gap or dimension D between the first energy delivery surface 365A and second energy delivery surface 365B of first jaw 364A and second jaw 364B, respectively. In various embodiments, dimension D can equal from about 0.0005" to about 0.040", for example, and in some embodiments, between about 0.001" to about 0.010", for example. Also, the edges of the first energy delivery surface 365A and the second energy delivery surface 365B may be rounded to prevent the dissection of tissue.

Figure 16:
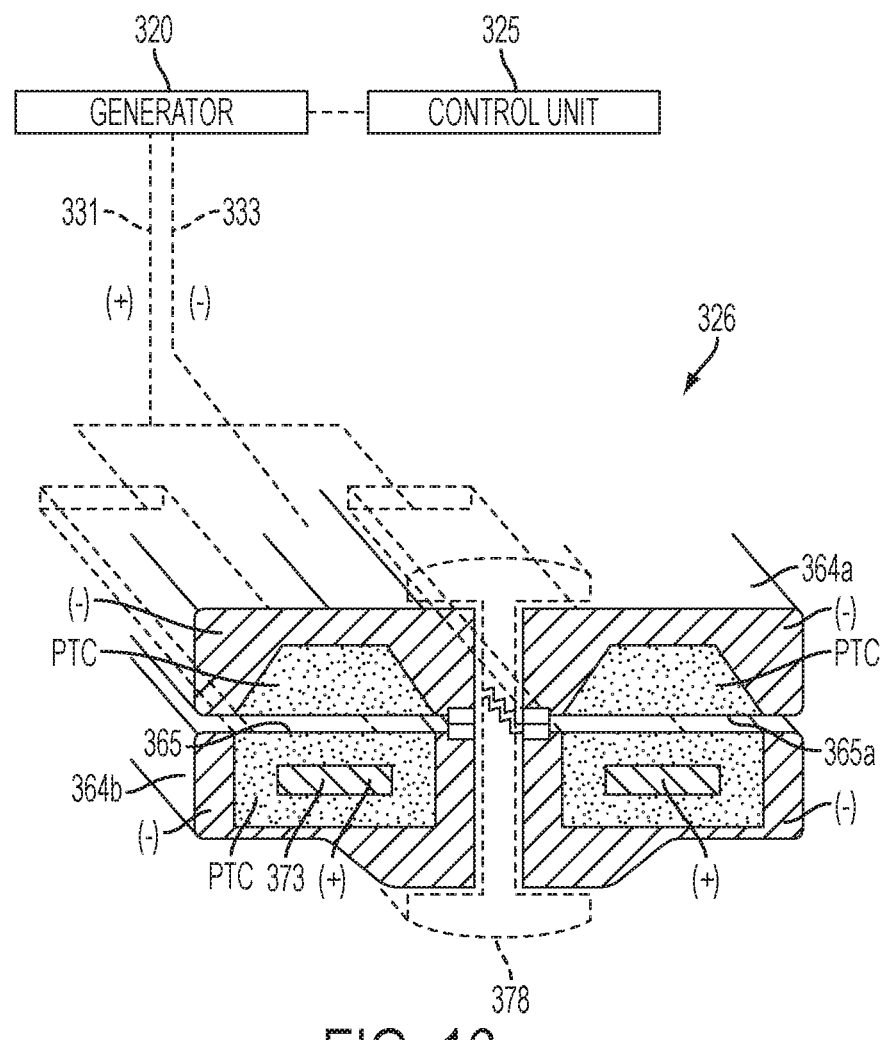
FIG. 16 illustrates a section view of one embodiment of the end effector of the surgical instrument of FIG. 11.

FIG. 16 is a section view of one example embodiment of the end effector 326 of the surgical instrument 310. The engagement, or tissue-contacting, surface 365B of the lower jaw 364B is adapted to deliver energy to tissue, at least in part, through a conductive-resistive matrix, such as a variable resistive positive temperature coefficient (PTC) body, as discussed in more detail below. At least one of the upper and lower jaws 364A, 364B may carry at least one electrode 373 configured to deliver the energy from the generator 320 to the captured tissue. The engagement, or tissue-contacting, surface 365A of upper jaw 364A may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 365A and the second energy delivery surface 365B may each be in electrical communication with the generator 320. The first energy delivery surface 365A and the second energy delivery surface 365B may be configured to contact tissue and deliver electrosurgical energy to captured tissue which are adapted to seal or weld the tissue. The control unit 325 regulates the electrical energy delivered by electrical generator 320 which in turn delivers electrosurgical energy to the first energy delivery surface 365A and the second energy delivery surface 365B. The energy delivery may be initiated by an activation button 328 (FIG. 12) operably engaged with the lever arm 321 and in electrical communication with the generator 320 via cable 322. In one example embodiment, the electrosurgical instrument 310 may be energized by the generator 320 by way of a foot switch 329 (FIG. 11). When actuated, the foot switch 329 triggers the generator 320 to deliver electrical energy to the end effector 326, for example. The control unit 325 may regulate the power generated by the generator 320 during activation. Although the foot switch 329 may be suitable in many circumstances, other suitable types of switches can be used.

As mentioned above, the electrosurgical energy delivered by electrical generator 320 and regulated, or otherwise controlled, by the control unit 325 may comprise radio frequency (RF) energy, or other suitable forms of electrical energy. Further, the opposing first and second energy delivery surfaces 365A and 365B may carry variable resistive positive temperature coefficient (PTC) bodies that are in electrical communication with the generator 320 and the control unit 325. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,312; and U.S. Pat. App. Pub. Nos. 2010/0036370 and 2009/0076506, all of which are incorporated herein in their entirety by reference and made a part of this specification.

In one example embodiment, the generator 320 may be implemented as an electrosurgery unit (ESU) capable of supplying power sufficient to perform bipolar electrosurgery using radio frequency (RF) energy. In one example embodiment, the ESU can be a bipolar ERBE ICC 350 sold by ERBE USA, Inc. of Marietta, Ga. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the positive temperature coefficient (PTC) bodies and to the return electrode through the tissue. Thus, in various embodiments, the electrosurgical system 300 may comprise a supply path and a return path, wherein the captured tissue being treated completes, or closes, the circuit. In one example embodiment, the generator 320 may be a monopolar RF ESU and the electrosurgical instrument 310 may comprise a monopolar end effector 326 in which one or more active electrodes are integrated. For such a system, the generator 320 may require a return pad in intimate contact with the patient at a location remote from the operative site and/or other suitable return path. The return pad may be connected via a cable to the generator 320. In other embodiments, the operator 20 may provide sub-therapeutic RF energy levels for purposes of evaluating tissue conditions and providing feedback in the electrosurgical system 300. Such feedback may be employed to control the therapeutic RF energy output of the electrosurgical instrument 310.

During operation of electrosurgical instrument 300, the user generally grasps tissue, supplies energy to the captured tissue to form a weld or a seal (e.g., by actuating button 328 and/or pedal 216), and then drives a tissue-cutting element 371 at the distal end of the axially moveable member 378 through the captured tissue. According to various embodiments, the translation of the axial movement of the axially moveable member 378 may be paced, or otherwise controlled, to aid in driving the axially moveable member 378 at a suitable rate of travel. By controlling the rate of the travel, the likelihood that the captured tissue has been properly and functionally sealed prior to transection with the cutting element 371 is increased.

Figure 17:
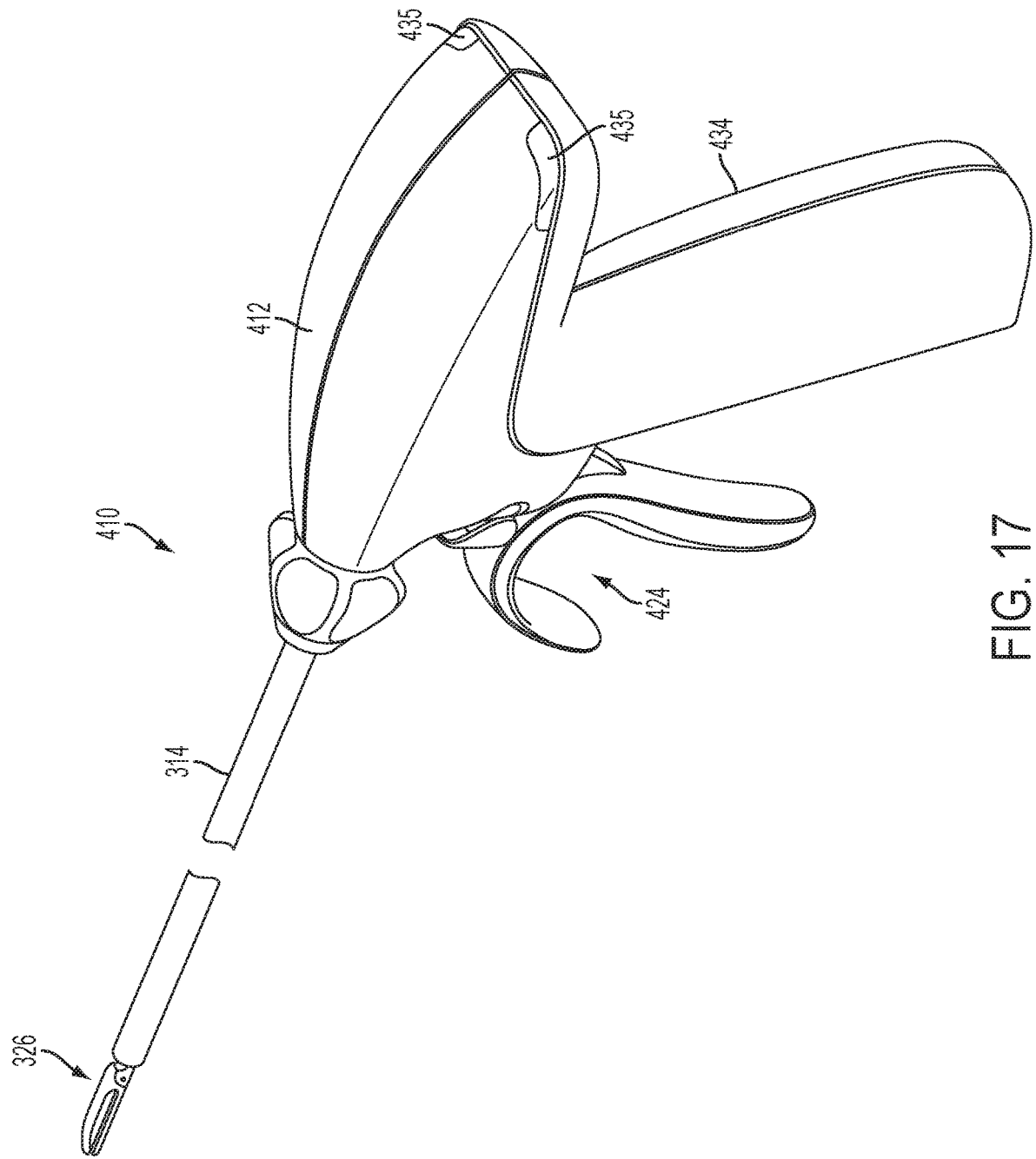
FIG. 17 illustrates a section a perspective view of one embodiment of a wireless electrical energy surgical instrument.

FIG. 17 is a perspective view of one example embodiment of a surgical instrument system comprising a wireless electrical energy surgical instrument 410. The electrosurgical system is similar to the electrosurgical system 300. The electrosurgical system can be configured to supply energy, such as electrical energy, ultrasonic energy, heat energy, or any combination thereof, to the tissue of a patient either independently or simultaneously as described in connection with FIGS. 1 and 11, for example. The electrosurgical instrument may utilize the end effector 326 and elongated shaft 314 described herein in conjunction with a wireless proximal handle 412. In one example embodiment, the handle 412 includes a generator circuit 420 (see FIG. 18A). The generator circuit 420 performs a function substantially similar to that of generator 320. In one example embodiment, the generator circuit 420 is coupled to a controller, such as a control circuit. In the illustrated embodiment, the control circuit is integrated into the generator circuit 420. In other embodiments, the control circuit may be separate from the generator circuit 420.

In one example embodiment, various electrodes in the end effector 326 (including jaws 364A, 364B thereof) may be coupled to the generator circuit 420. The control circuit may be used to activate the generator 420, which may serve as an electrical source. In various embodiments, the generator 420 may comprise an RF source, an ultrasonic source, a direct current source, and/or any other suitable type of electrical energy source, for example. In one example embodiment, a button 328 may be provided to activate the generator circuit 420 to provide energy to the end effectors 326, 326.

FIG. 18A is a side view of one example embodiment of the handle 412 of the wireless surgical instrument 410. In FIG. 18A, the handle 412 is shown with half of a first handle body removed to illustrate various components within second handle body 434. The handle 412 may comprise a lever arm 424 (e.g., a trigger) which may be pulled along a path 33 around a pivot point. The lever arm 424 may be coupled to an axially moveable member 478 disposed within elongated shaft 314 by a shuttle operably engaged to an extension of lever arm 424. In one example embodiment, the lever arm 424 defines a shepherd's hook shape comprising a distal member 424a and a proximal member 424b.

In one example embodiment, the wireless electrosurgical instrument comprises a battery 437. The battery 437 provides electrical energy to the generator circuit 420. The battery 437 may be any battery suitable for driving the generator circuit 420 at the desired energy levels. In one example embodiment, the battery 437 is a 100 mAh, triple-cell Lithium Ion Polymer battery. The battery may be fully charged prior to use in a surgical procedure, and may hold a voltage of about 12.6V. The battery 437 may have two fuses fitted to the wireless electrosurgical instrument 410, arranged in line with each battery terminal. In one example embodiment, a charging port 439 is provided to connect the battery 437 to a DC current source (not shown).

Figure 18B:
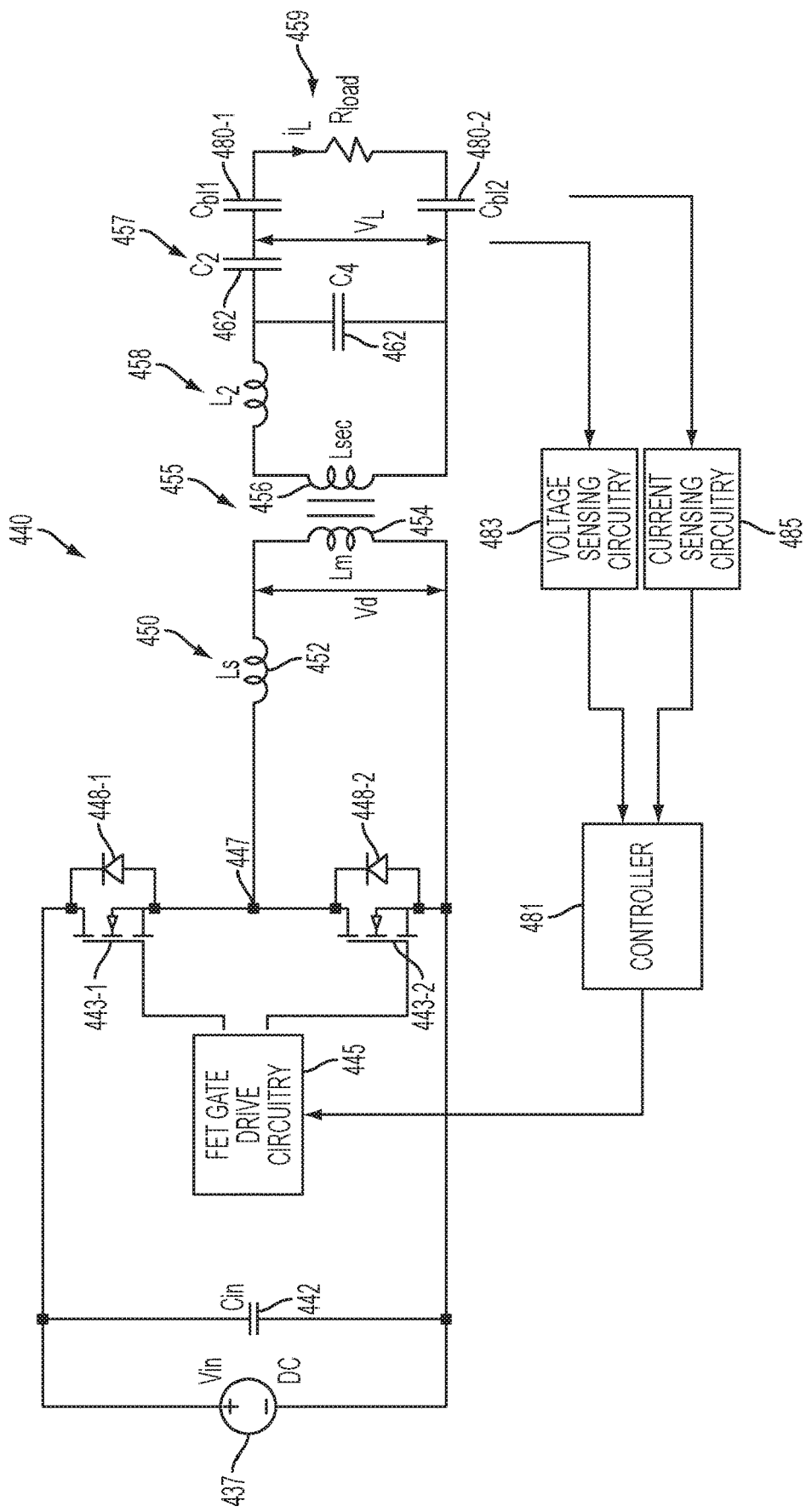
FIG. 18B illustrates an RF drive and control circuit, according to one embodiment.

The generator circuit 420 may be configured in any suitable manner. In some embodiments, the generator circuit comprises an RF drive and control circuit 440 and a controller circuit 482. FIG. 18B illustrates an RF drive and control circuit 440, according to one embodiment. FIG. 18B is a part schematic part block diagram illustrating the RF drive and control circuitry 440 used in this embodiment to generate and control the RF electrical energy supplied to the end effector 326. As will be explained in more detail below, in this embodiment, the drive circuitry 440 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the end effector 326. The way that this is achieved will become apparent from the following description.

As shown in FIG. 18B, the RF drive and control circuit 440 comprises the above described battery 437 are arranged to supply, in this example, about 0V and about 12V rails. An input capacitor ($C_{in}$) 442 is connected between the 0V and the 12V for providing a low source impedance. A pair of FET switches 443-1 and 443-2 (both of which are N-channel in this embodiment to reduce power losses) is connected in series between the 0V rail and the 12V rail. FET gate drive circuitry 805 is provided that generates two drive signals—one for driving each of the two FETs 443. The FET gate drive circuitry 445 generates drive signals that causes the upper FET (443-1) to be on when the lower FET (443-2) is off and vice versa. This causes the node 447 to be alternately connected to the 12V rail (when the FET 443-1 is switched on) and the 0V rail (when the FET 443-2 is switched on). FIG. 18B also shows the internal parasitic diodes 448-1 and 448-2 of the corresponding FETs 443, which conduct during any periods that the FETs 443 are open.

As shown in FIG. 18B, the node 447 is connected to an inductor-inductor resonant circuit 450 formed by inductor $L_s$ 452 and inductor $L_m$ 454. The FET gate driving circuitry 445 is arranged to generate drive signals at a drive frequency ($f_d$) that opens and crosses the FET switches 443 at the resonant frequency of the parallel resonant circuit 450. As a result of the resonant characteristic of the resonant circuit 450, the square wave voltage at node 447 will cause a substantially sinusoidal current at the drive frequency ($f_d$) to flow within the resonant circuit 450. As illustrated in FIG. 18B, the inductor $L_m$ 454 is the primary of a transformer 455, the secondary of which is formed by inductor $L_{sec}$ 456. The inductor $L_{sec}$ 456 of the transformer 455 secondary is connected to an inductor-capacitor-capacitor parallel resonant circuit 457 formed by inductor $L_2$ 458, capacitor $C_4$ 460, and capacitor $C_2$ 462. The transformer 455 up-converts the drive voltage ($V_d$) across the inductor $L_m$ 454 to the voltage that is applied to the output parallel resonant circuit 457. The load voltage ($V_L$) is output by the parallel resonant circuit 457 and is applied to the load (represented by the load resistance $R_{load}$ 459 in FIG. 18B) corresponding to the impedance of the forceps' jaws and any tissue or vessel gripped by the end effector 326. As shown in FIG. 18B, a pair of DC blocking capacitors $C_{bl}$ 480-1 and 480-2 is provided to prevent any DC signal being applied to the load 459.

In one embodiment, the transformer 455 may be implemented with a Core Diameter (mm), Wire Diameter (mm), and Gap between secondary windings in accordance with the following specifications:

Core Diameter, D (mm)
D=19.9×10-3
Wire diameter, W (mm) for 22 AWG wire
W=7.366×10-4
Gap between secondary windings, in gap=0.125
G=gap/25.4

In this embodiment, the amount of electrical power supplied to the end effector 326 is controlled by varying the frequency of the switching signals used to switch the FETs 443. This works because the resonant circuit 450 acts as a frequency dependent (loss less) attenuator. The closer the drive signal is to the resonant frequency of the resonant circuit 450, the less the drive signal is attenuated. Similarly, as the frequency of the drive signal is moved away from the resonant frequency of the circuit 450, the more the drive signal is attenuated and so the power supplied to the load reduces. In this embodiment, the frequency of the switching signals generated by the FET gate drive circuitry 445 is controlled by a controller 481 based on a desired power to be delivered to the load 459 and measurements of the load voltage ($V_L$) and of the load current ($I_L$) obtained by conventional voltage sensing circuitry 483 and current sensing circuitry 485. The way that the controller 481 operates will be described in more detail below.

In one embodiment, the voltage sensing circuitry 483 and the current sensing circuitry 485 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 483 and the current sensing circuitry 485. In one-embodiment, a step-down regulator (e.g., LT3502 by Linear Technologies) may be employed by the power save circuit to reduce the supply voltage of the rail-to-rail amplifiers and thus extend the life of the battery 437.

Figure 18C:
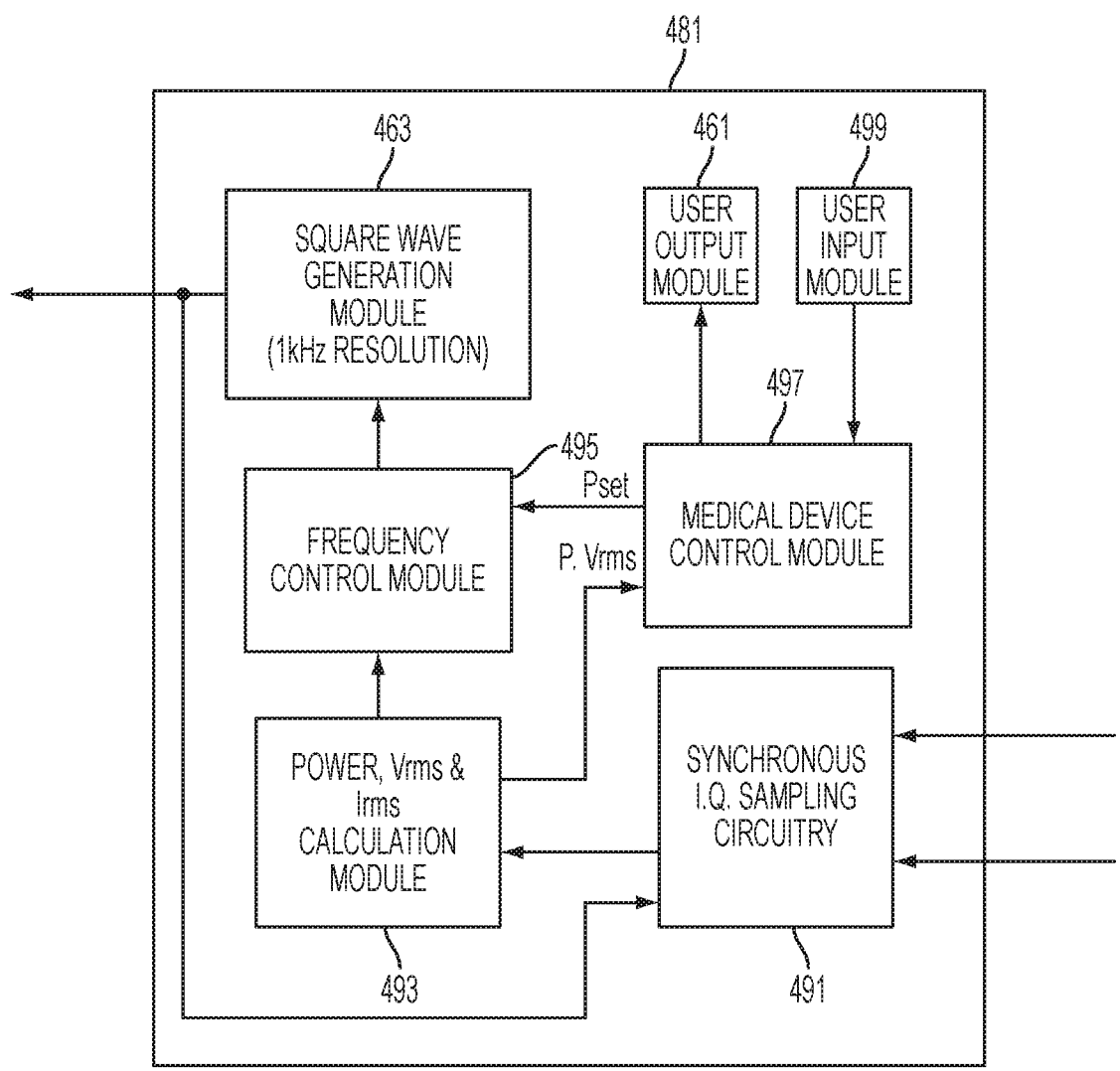
FIG. 18C illustrates the main components of the controller, according to one embodiment

FIG. 18C illustrates the main components of the controller 481, according to one embodiment. In the embodiment illustrated in FIG. 18C, the controller 481 is a microprocessor based controller and so most of the components illustrated in FIG. 16 are software based components. Nevertheless, a hardware based controller 481 may be used instead. As shown, the controller 481 includes synchronous I,Q sampling circuitry 491 that receives the sensed voltage and current signals from the sensing circuitry 483 and 485 and obtains corresponding samples which are passed to a power, $V_{rms}$ and $I_{rms}$ calculation module 493. The calculation module 493 uses the received samples to calculate the RMS voltage and RMS current applied to the load 459 (FIG. 18B; end effector 326 and tissue/vessel gripped thereby) and from them the power that is presently being supplied to the load 459. The determined values are then passed to a frequency control module 495 and a medical device control module 497. The medical device control module 497 uses the values to determine the present impedance of the load 459 and based on this determined impedance and a pre-defined algorithm, determines what set point power ($P_{set}$) should be applied to the frequency control module 495. The medical device control module 497 is in turn controlled by signals received from a user input module 499 that receives inputs from the user (for example pressing buttons or activating the control levers 114, 110 on the handle 104) and also controls output devices (lights, a display, speaker or the like) on the handle 104 via a user output module 461.

The frequency control module 495 uses the values obtained from the calculation module 493 and the power set point ($P_{set}$) obtained from the medical device control module 497 and predefined system limits (to be explained below), to determine whether or not to increase or decrease the applied frequency. The result of this decision is then passed to a square wave generation module 463 which, in this embodiment, increments or decrements the frequency of a square wave signal that it generates by 1 kHz, depending on the received decision. As those skilled in the art will appreciate, in an alternative embodiment, the frequency control module 495 may determine not only whether to increase or decrease the frequency, but also the amount of frequency change required. In this case, the square wave generation module 463 would generate the corresponding square wave signal with the desired frequency shift. In this embodiment, the square wave signal generated by the square wave generation module 463 is output to the FET gate drive circuitry 445, which amplifies the signal and then applies it to the FET 443-1. The FET gate drive circuitry 445 also inverts the signal applied to the FET 443-1 and applies the inverted signal to the FET 443-2.

The electrosurgical instrument 410 may comprise additional features as discussed with respect to electrosurgical system 300. Those skilled in the art will recognize that electrosurgical instrument 410 may include a rotation knob 348, an elongated shaft 314, and an end effector 326. These elements function in a substantially similar manner to that discussed above with respect to the electrosurgical system 300. In one example embodiment, the wireless electrosurgical instrument 410 may include visual indicators 435. The visual indicators 435 may provide a visual indication signal to an operator. In one example embodiment, the visual indication signal may alert an operator that the device is on, or that the device is applying energy to the end effector. Those skilled in the art will recognize that the visual indicators 435 may be configured to provide information on multiple states of the device.

Over the years a variety of minimally invasive robotic (or "telesurgical") systems have been developed to increase surgical dexterity as well as to permit a surgeon to operate on a patient in an intuitive manner. Robotic surgical systems can be used with many different types of surgical instruments including, for example, ultrasonic or electrosurgical instruments, as described herein. Example robotic systems include those manufactured by Intuitive Surgical, Inc., of Sunnyvale, Calif., U.S.A. Such systems, as well as robotic systems from other manufacturers, are disclosed in the following U.S. patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUs For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Wristed Monopolar Electrosurgical End Effectors". Many of such systems, however, have in the past been unable to generate the magnitude of forces required to effectively cut and fasten tissue.

FIGS. 19-46C illustrate example embodiments of robotic surgical systems. In some embodiments, the disclosed robotic surgical systems may utilize the ultrasonic or electrosurgical instruments described herein. Those skilled in the art will appreciate that the illustrated robotic surgical systems are not limited to only those instruments described herein, and may utilize any compatible surgical instruments. Those skilled in the art will further appreciate that while various embodiments described herein may be used with the described robotic surgical systems, the disclosure is not so limited, and may be used with any compatible robotic surgical system.

Figure 19:
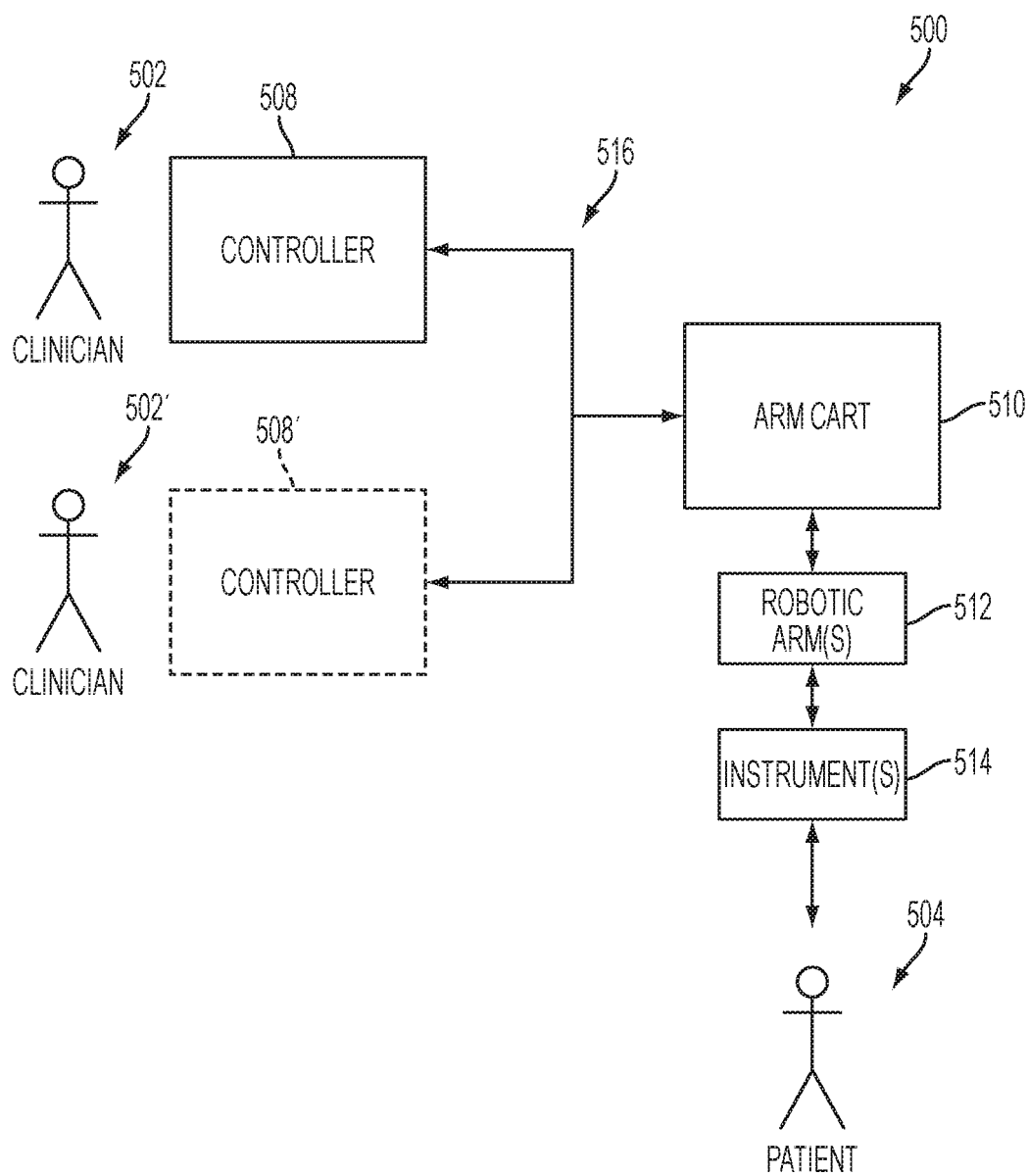
FIG. 19 illustrates a block diagram of one embodiment of a robotic surgical system.

FIGS. 19-25 illustrate the structure and operation of several example robotic surgical systems and components thereof. FIG. 19 shows a block diagram of an example robotic surgical system 1000. The system 1000 comprises at least one controller 508 and at least one arm cart 510. The arm cart 510 may be mechanically coupled to one or more robotic manipulators or arms, indicated by box 512. Each of the robotic arms 512 may comprise one or more surgical instruments 514 for performing various surgical tasks on a patient 504. Operation of the arm cart 510, including the arms 512 and instruments 514 may be directed by a clinician 502 from a controller 508. In some embodiments, a second controller 508', operated by a second clinician 502' may also direct operation of the arm cart 510 in conjunction with the first clinician 502'. For example, each of the clinicians 502, 502' may control different arms 512 of the cart or, in some cases, complete control of the arm cart 510 may be passed between the clinicians 502, 502'. In some embodiments, additional arm carts (not shown) may be utilized on the patient 504. These additional arm carts may be controlled by one or more of the controllers 508, 508'. The arm cart(s) 510 and controllers 508, 508' may be in communication with one another via a communications link 516, which may be any suitable type of wired or wireless communications link carrying any suitable type of signal (e.g., electrical, optical, infrared, etc.) according to any suitable communications protocol. Example implementations of robotic surgical systems, such as the system 1000, are disclosed in U.S. Pat. No. 7,524,320 which has been herein incorporated by reference. Thus, various details of such devices will not be described in detail herein beyond that which may be necessary to understand various embodiments of the claimed device.

Figure 20:
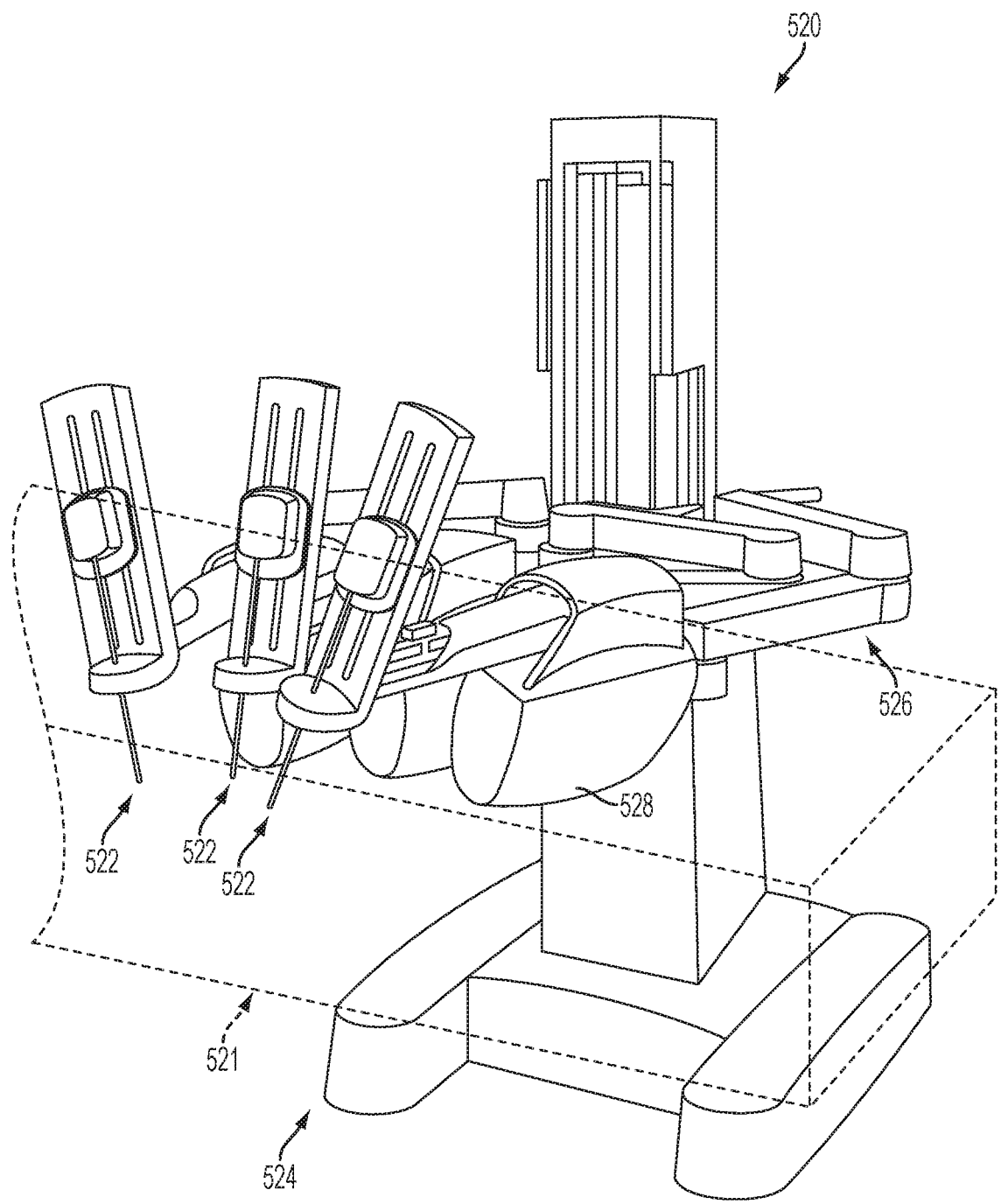
FIG. 20 illustrates one embodiment of a robotic arm cart.

FIG. 20 shows one example embodiment of a robotic arm cart 520. The robotic arm cart 520 is configured to actuate a plurality of surgical instruments or instruments, generally designated as 522 within a work envelope 519. Various robotic surgery systems and methods employing master controller and robotic arm cart arrangements are disclosed in U.S. Pat. No. 6,132,368, entitled "Multi-Component Telepresence System and Method", the full disclosure of which is incorporated herein by reference. In various forms, the robotic arm cart 520 includes a base 524 from which, in the illustrated embodiment, three surgical instruments 522 are supported. In various forms, the surgical instruments 522 are each supported by a series of manually articulatable linkages, generally referred to as set-up joints 526, and a robotic manipulator 528. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 520. Cart 520 will generally have dimensions suitable for transporting the cart 520 between operating rooms. The cart 520 may be configured to typically fit through standard operating room doors and onto standard hospital elevators. In various forms, the cart 520 would preferably have a weight and include a wheel (or other transportation) system that allows the cart 520 to be positioned adjacent an operating table by a single attendant.

Figure 21:
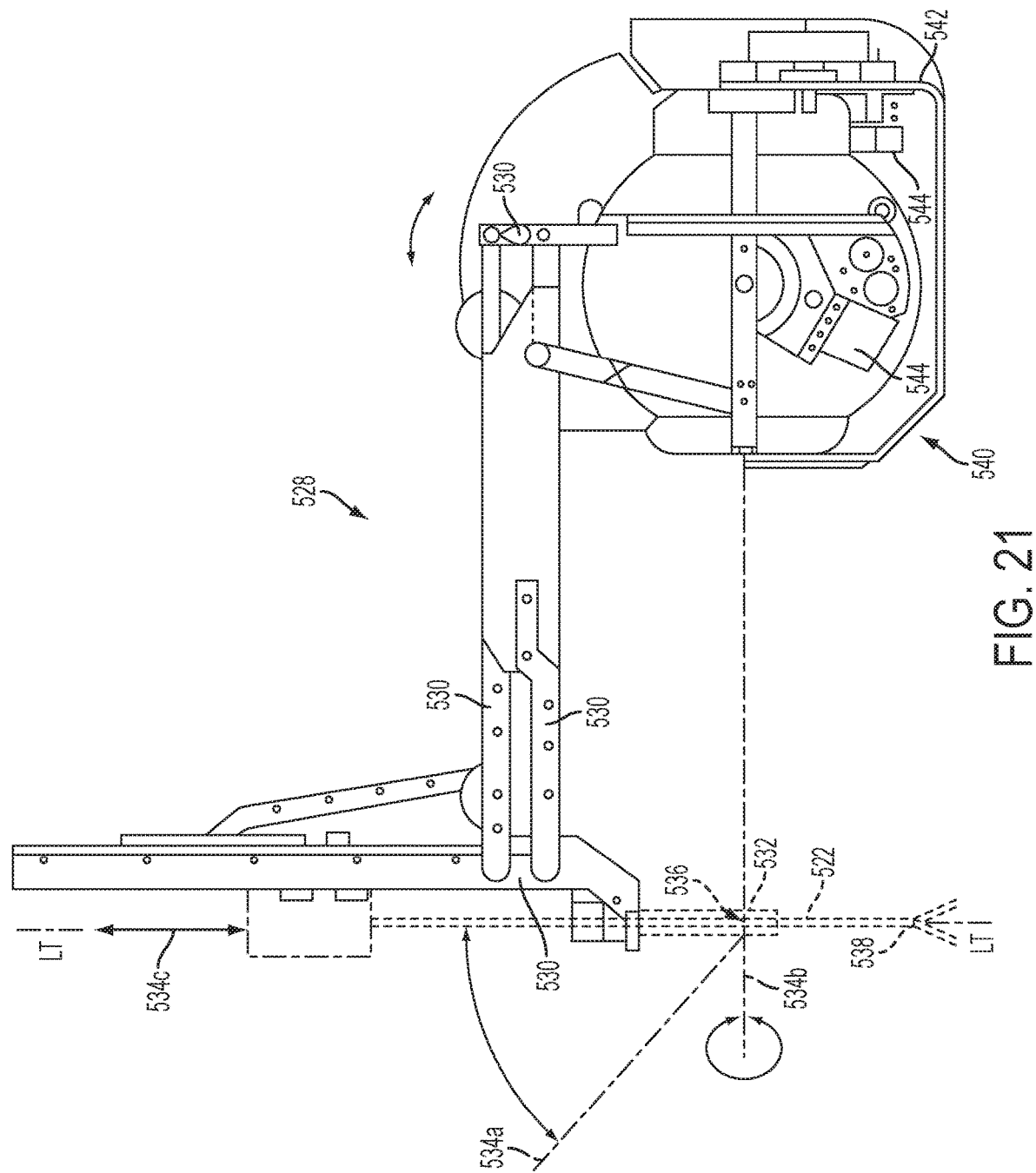
FIG. 21 illustrates one embodiment of the robotic manipulator of the robotic arm cart of FIG. 20.

FIG. 21 shows one example embodiment of the robotic manipulator 528 of the robotic arm cart 520. In the example shown in FIG. 21, the robotic manipulators 528 may include a linkage 530 that constrains movement of the surgical instrument 522. In various embodiments, linkage 530 includes rigid links coupled together by rotational joints in a parallelogram arrangement so that the surgical instrument 522 rotates around a point in space 532, as more fully described in issued U.S. Pat. No. 5,817,084, the full disclosure of which is herein incorporated by reference. The parallelogram arrangement constrains rotation to pivoting about an axis 534a, sometimes called the pitch axis. The links supporting the parallelogram linkage are pivotally mounted to set-up joints 526 (FIG. 20) so that the surgical instrument 522 further rotates about an axis 534b, sometimes called the yaw axis. The pitch and yaw axes 534a, 534b intersect at the remote center 536, which is aligned along a shaft 538 of the surgical instrument 522. The surgical instrument 522 may have further degrees of driven freedom as supported by manipulator 540, including sliding motion of the surgical instrument 522 along the longitudinal instrument axis "LT-LT". As the surgical instrument 522 slides along the instrument axis LT-LT relative to manipulator 540 (arrow 534c), remote center 536 remains fixed relative to base 542 of manipulator 540. Hence, the entire manipulator 540 is generally moved to re-position remote center 536. Linkage 530 of manipulator 540 is driven by a series of motors 544. These motors 544 actively move linkage 530 in response to commands from a processor of a control system. As will be discussed in further detail below, motors 544 are also employed to manipulate the surgical instrument 522.

Figure 22:
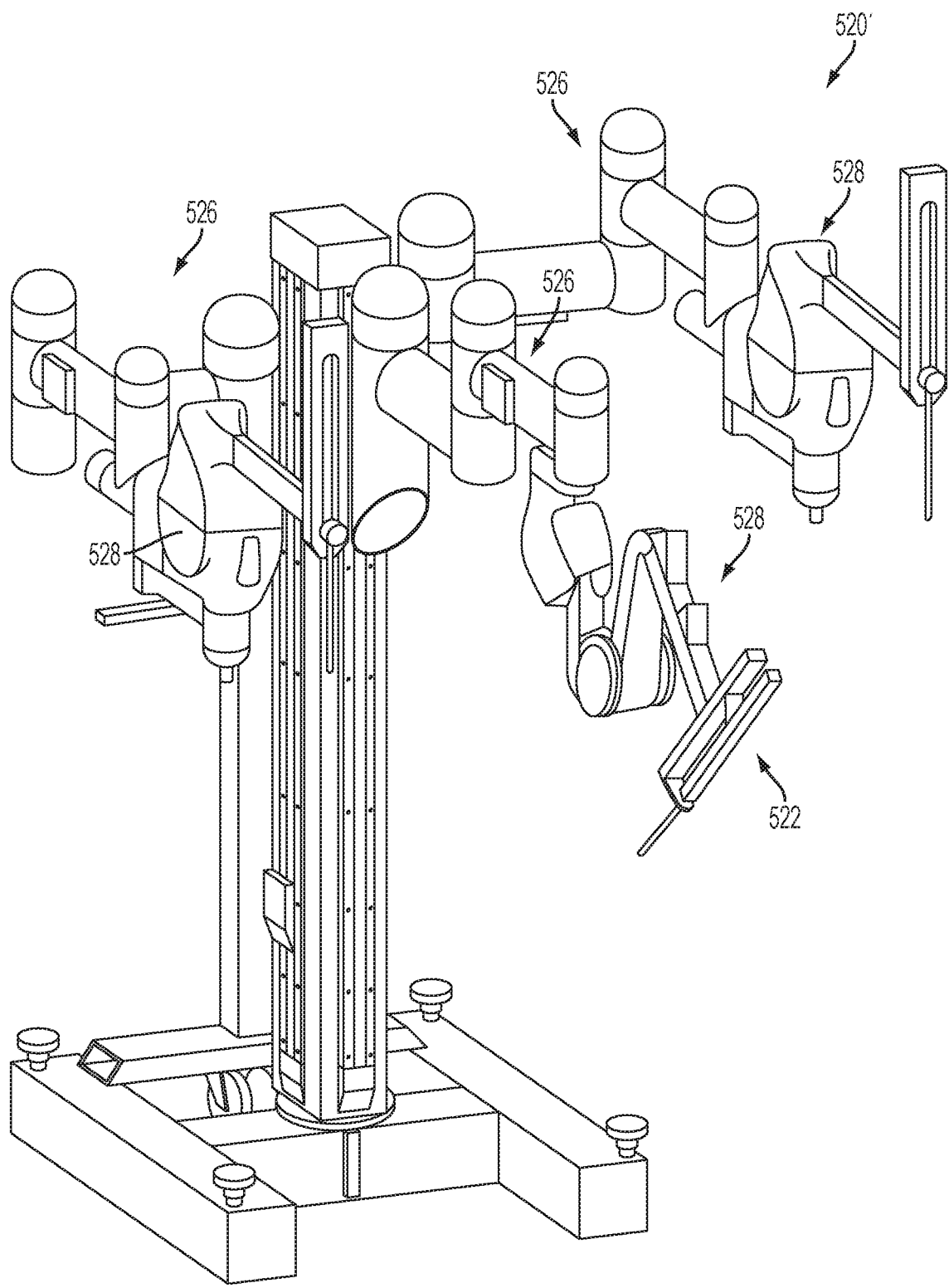
FIG. 22 illustrates one embodiment of a robotic arm cart having an alternative set-up joint structure.

FIG. 22 shows one example embodiment of a robotic arm cart 520' having an alternative set-up joint structure. In this example embodiment, a surgical instrument 522 is supported by an alternative manipulator structure 528' between two tissue manipulation instruments. Those of ordinary skill in the art will appreciate that various embodiments of the claimed device may incorporate a wide variety of alternative robotic structures, including those described in U.S. Pat. No. 5,878,193, the full disclosure of which is incorporated herein by reference. Additionally, while the data communication between a robotic component and the processor of the robotic surgical system is primarily described herein with reference to communication between the surgical instrument 522 and the controller, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 23:
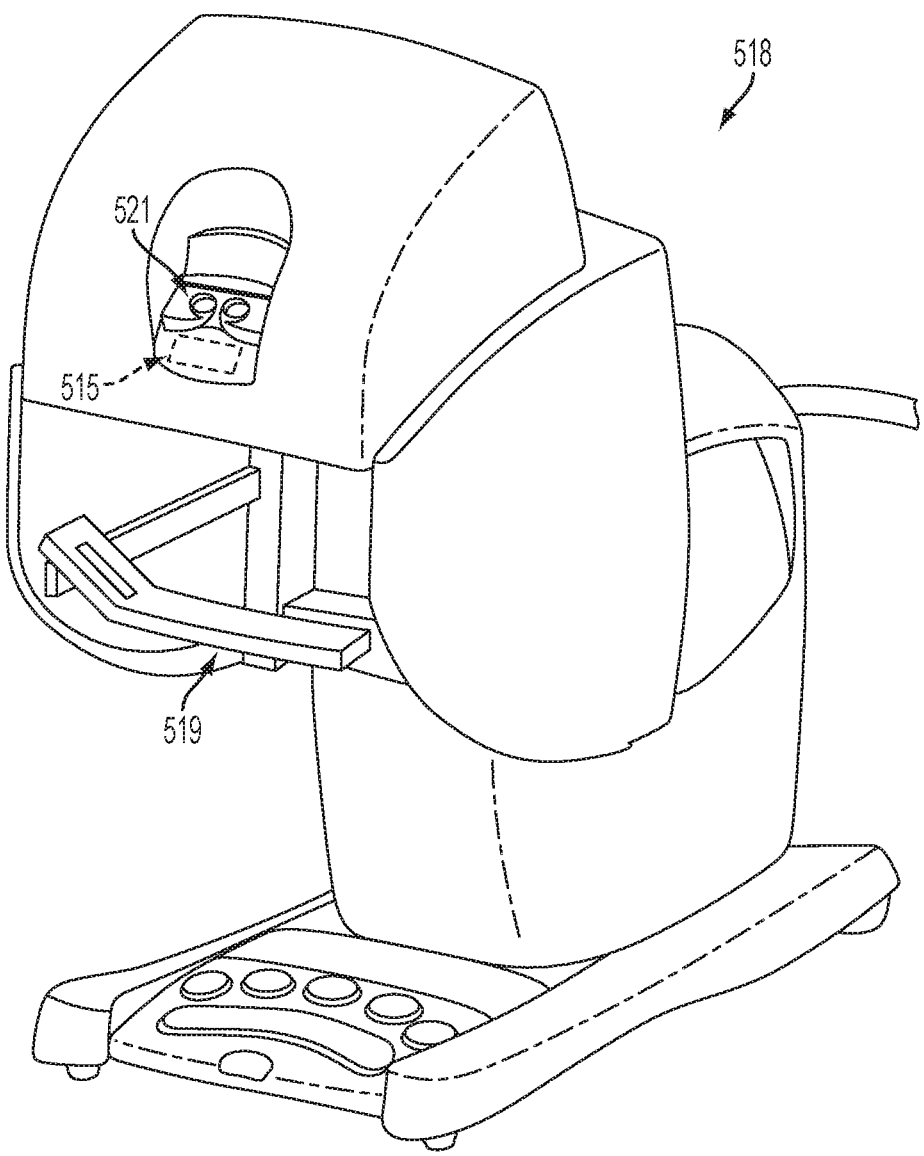
FIG. 23 illustrates one embodiment of a controller that may be used in conjunction with a robotic arm cart, such as the robotic arm carts of FIGS. 19-22.

FIG. 23 shows one example embodiment of a controller 518 that may be used in conjunction with a robotic arm cart, such as the robotic arm carts 520, 520' depicted in FIGS. 20-22. The controller 518 generally includes master controllers (generally represented as 519 in FIG. 23) which are grasped by the clinician and manipulated in space while the clinician views the procedure via a stereo display 521. A surgeon feed back meter 515 may be viewed via the display 521 and provide the surgeon with a visual indication of the amount of force being applied to the cutting instrument or dynamic clamping member. The master controllers 519 generally comprise manual input devices which preferably move with multiple degrees of freedom, and which often further have a handle or trigger for actuating instruments (for example, for closing grasping saws, applying an electrical potential to an electrode, or the like).

Figure 24:
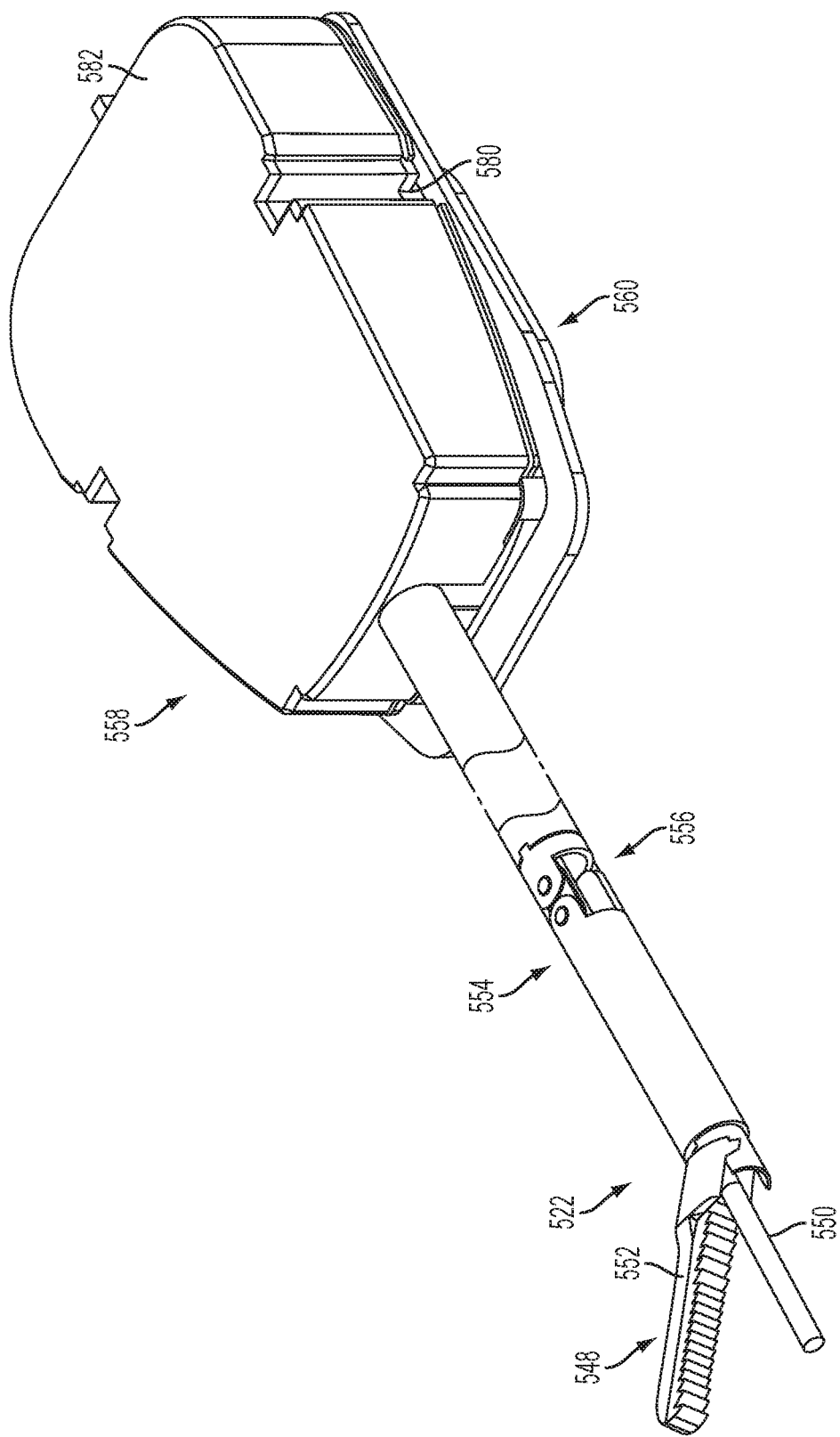
FIG. 24 illustrates one embodiment of an ultrasonic surgical instrument adapted for use with a robotic system.
Figure 25:
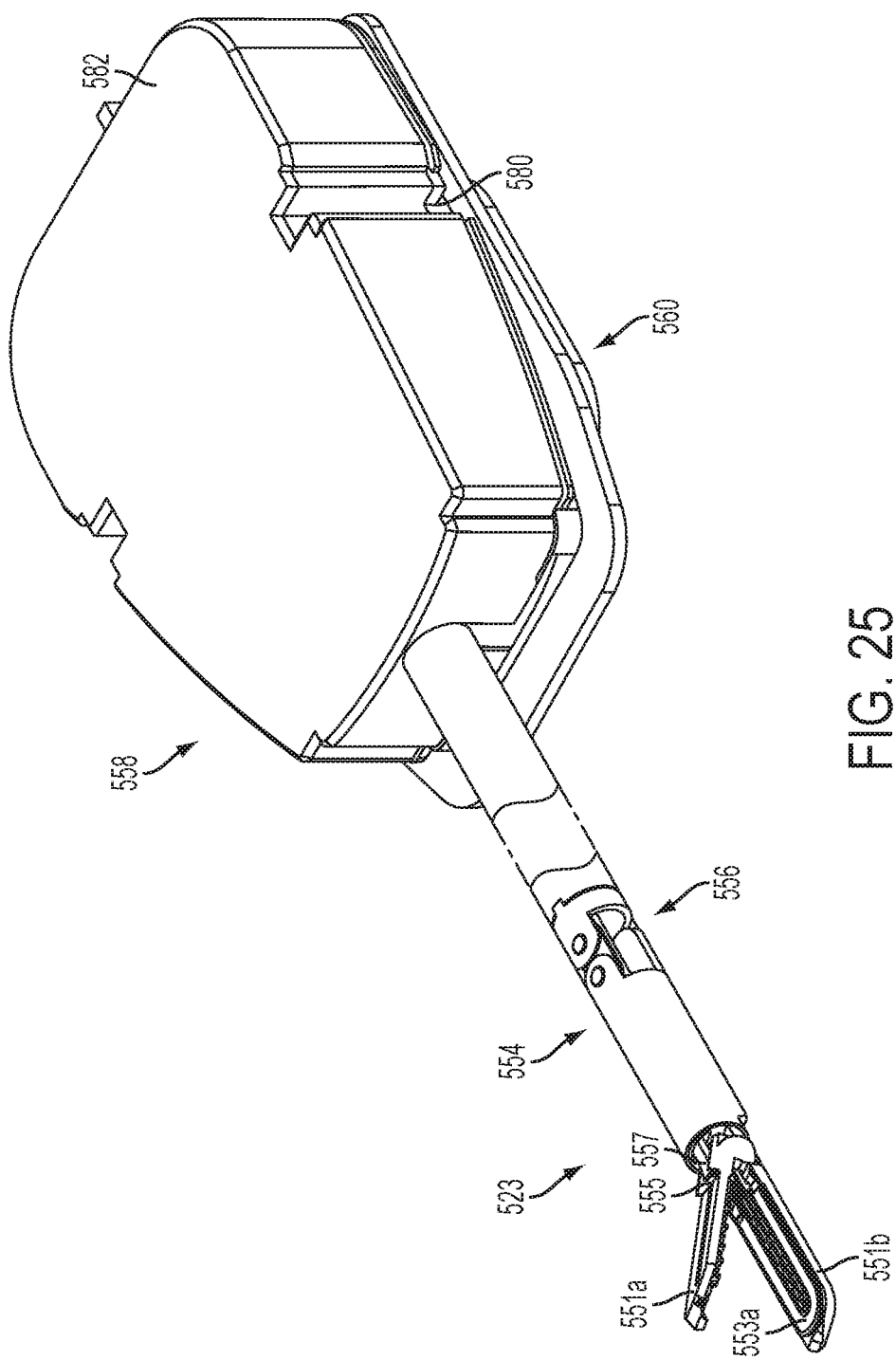
FIG. 25 illustrates one embodiment of an electrosurgical instrument adapted for use with a robotic system.
Figure 26:
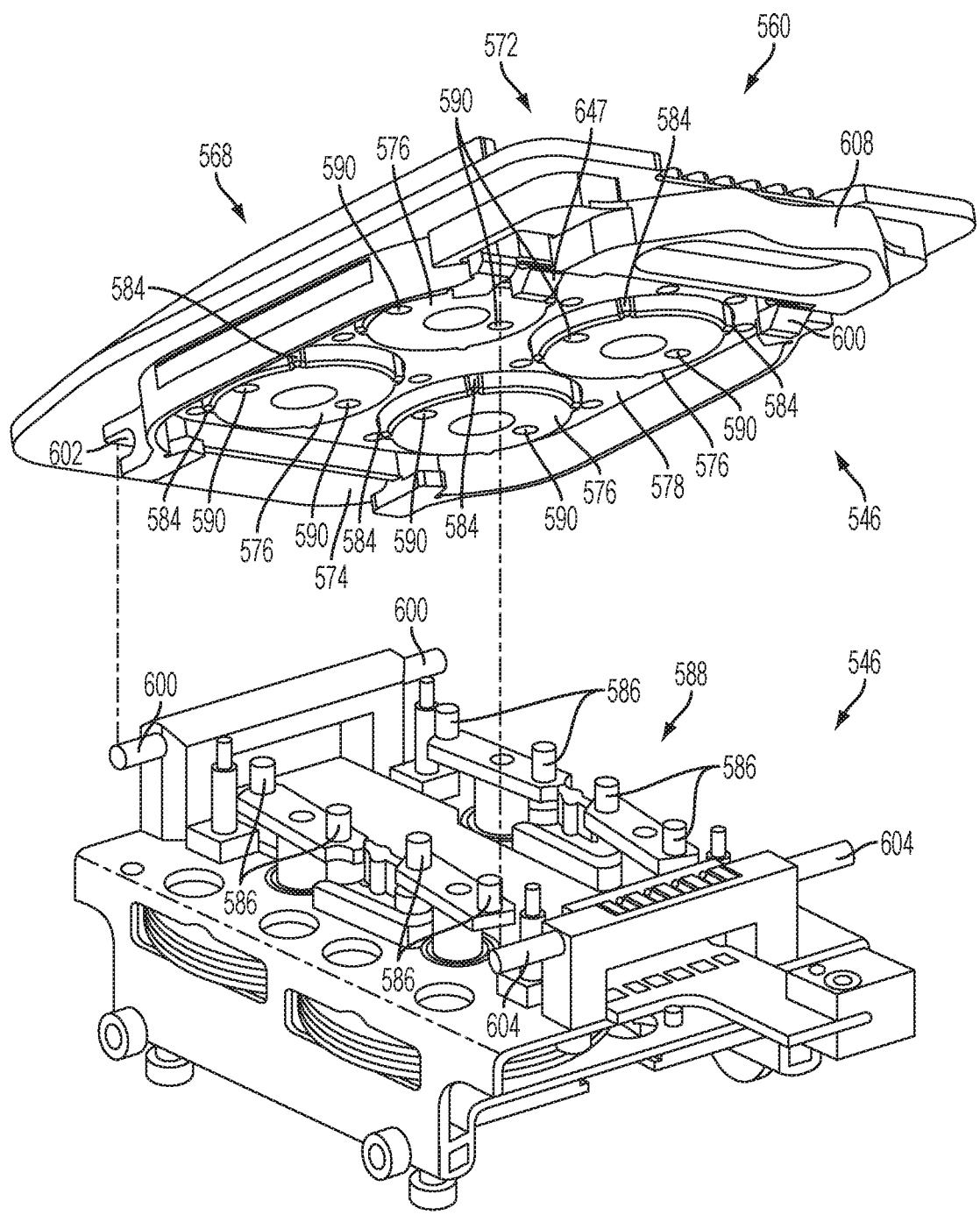
FIG. 26 illustrates one embodiment of an instrument drive assembly that may be coupled to a surgical manipulator to receive and control the surgical instrument shown in FIG. 24.

FIG. 24 shows one example embodiment of an ultrasonic surgical instrument 522 adapted for use with a robotic surgical system. For example, the surgical instrument 522 may be coupled to one of the surgical manipulators 528, 528' described hereinabove. As can be seen in FIG. 24, the surgical instrument 522 comprises a surgical end effector 548 that comprises an ultrasonic blade 550 and clamp arm 552, which may be coupled to an elongated shaft assembly 554 that, in some embodiments, may comprise an articulation joint 556. FIG. 25 shows another example embodiment having an electrosurgical instrument 523 in place of the ultrasonic surgical instrument 522. The surgical instrument 523 comprises a surgical end effector 548 that comprises closable jaws 551A, 551B having energy delivery surfaces 553A, 553B for engaging and providing electrical energy to tissue between the jaws 551A, 551B. A tissue cutting element or knife 555 may be positioned at the distal end of an axially movable member 557 that may extend through the elongated shaft assembly 554 to the instrument mounting portion 558. FIG. 26 shows one example embodiment of an instrument drive assembly 546 that may be coupled to one of the surgical manipulators 528, 528' to receive and control the surgical instruments 522, 523. The instrument drive assembly 546 may also be operatively coupled to the controller 518 to receive inputs from the clinician for controlling the instrument 522, 523. For example, actuation (e.g., opening and closing) of the clamp arm 552, actuation (e.g., opening and closing) of the jaws 551A, 551B, actuation of the ultrasonic blade 550, extension of the knife 555 and actuation of the energy delivery surfaces 553A, 553B, etc. may be controlled through the instrument drive assembly 546 based on inputs from the clinician provided through the controller 518. The surgical instrument 522 is operably coupled to the manipulator by an instrument mounting portion, generally designated as 558. The surgical instruments 522 further include an interface 560 which mechanically and electrically couples the instrument mounting portion 558 to the manipulator.

Figure 27:
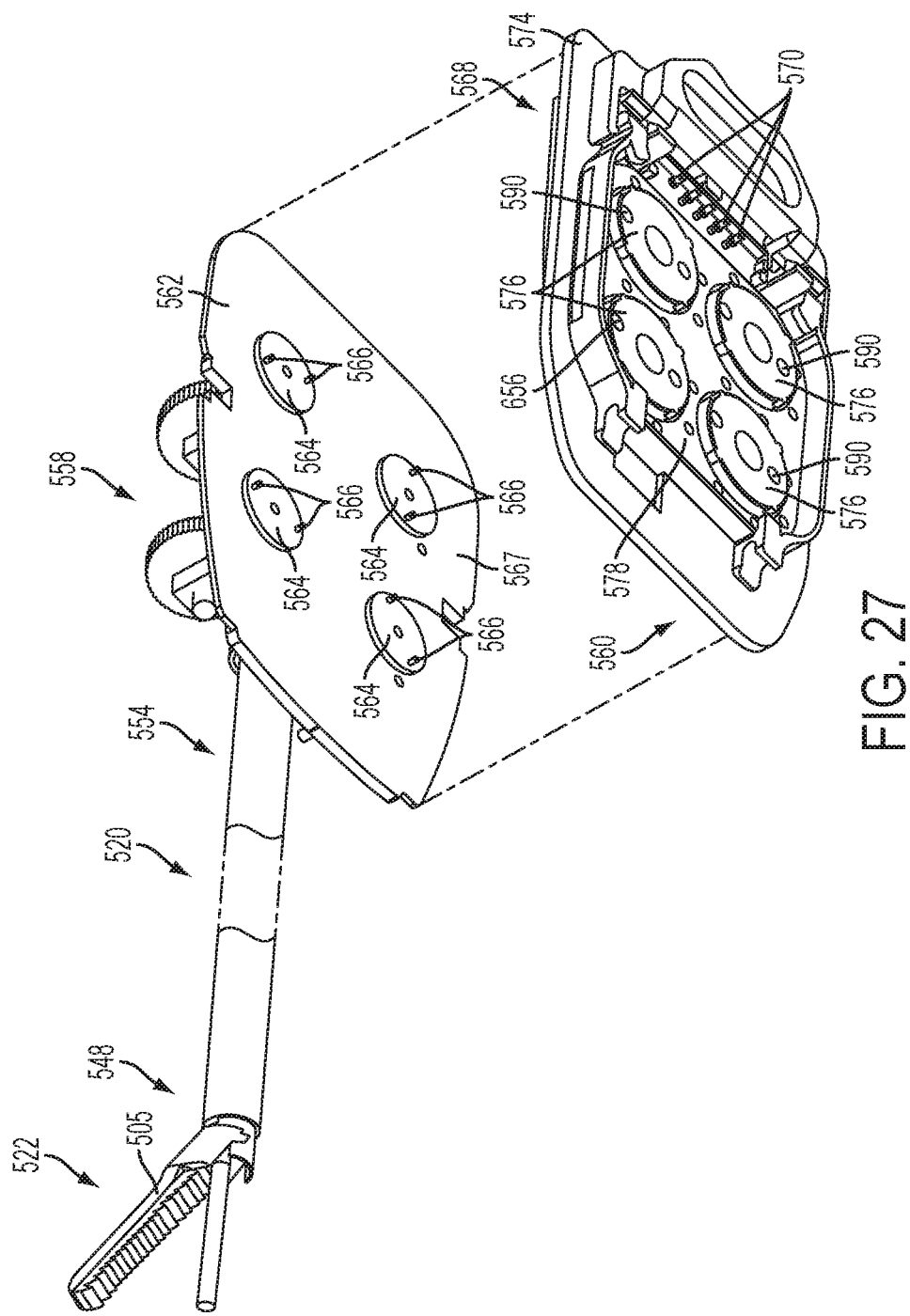
FIG. 27 illustrates another view of the instrument drive assembly embodiment of FIG. 26 including the surgical instrument of FIG. 24.
Figure 28:
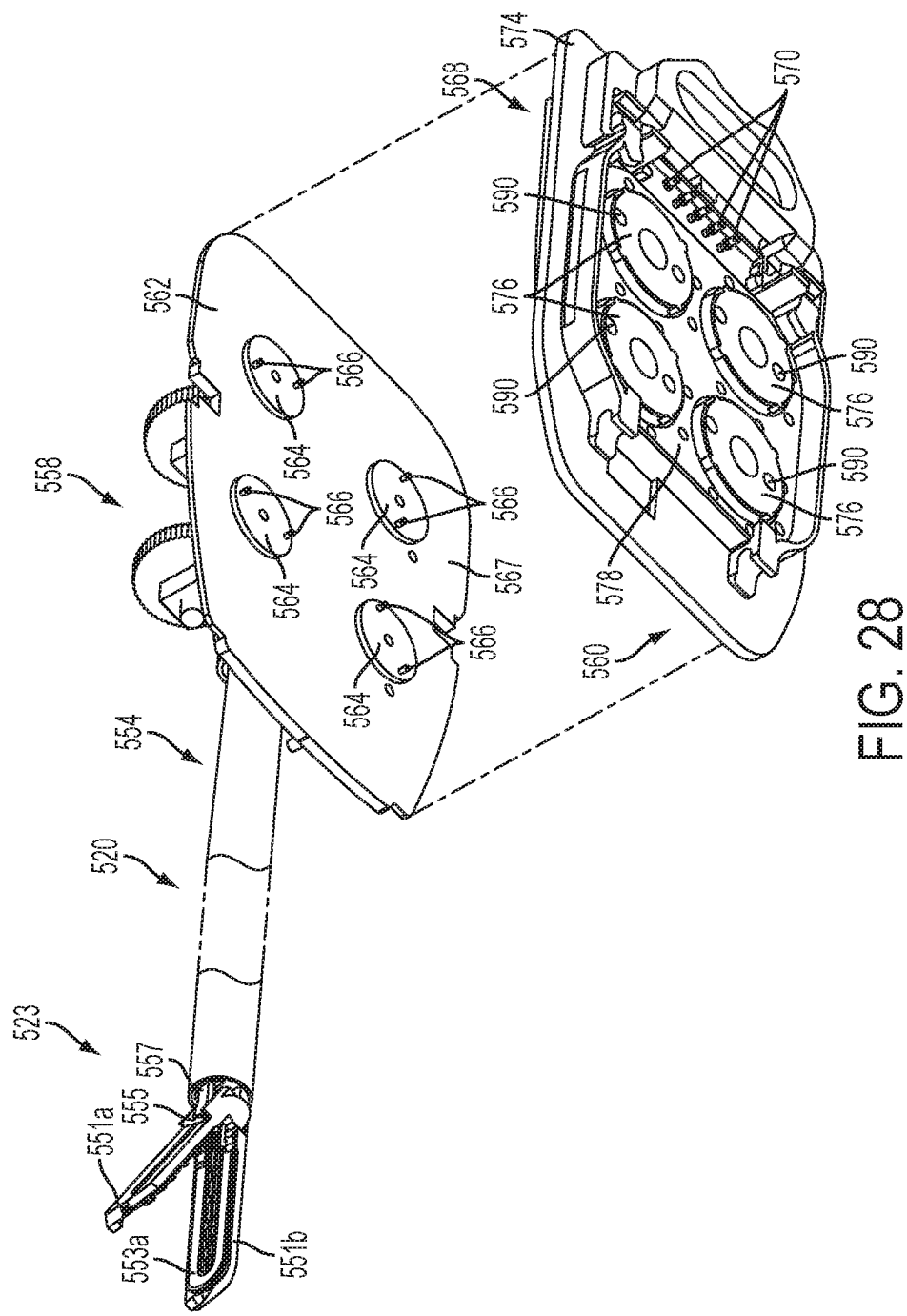
FIG. 28 illustrates another view of the instrument drive assembly embodiment of FIG. 26 including the electrosurgical instrument of FIG. 25.

FIG. 27 shows another view of the instrument drive assembly of FIG. 26 including the ultrasonic surgical instrument 522. FIG. 28 shows another view of the instrument drive assembly of FIG. 26 including the electrosurgical instrument 523. The instrument mounting portion 558 includes an instrument mounting plate 562 that operably supports a plurality of (four are shown in FIG. 26) rotatable body portions, driven discs or elements 564, that each include a pair of pins 566 that extend from a surface of the driven element 564. One pin 566 is closer to an axis of rotation of each driven elements 564 than the other pin 566 on the same driven element 564, which helps to ensure positive angular alignment of the driven element 564. The driven elements 564 and pints 566 may be positioned on an adapter side 567 of the instrument mounting plate 562.

Interface 560 also includes an adaptor portion 568 that is configured to mountingly engage the mounting plate 562 as will be further discussed below. The adaptor portion 568 may include an array of electrical connecting pins 570, which may be coupled to a memory structure by a circuit board within the instrument mounting portion 558. While interface 560 is described herein with reference to mechanical, electrical, and magnetic coupling elements, it should be understood that a wide variety of telemetry modalities might be used, including infrared, inductive coupling, or the like.

Figure 29:
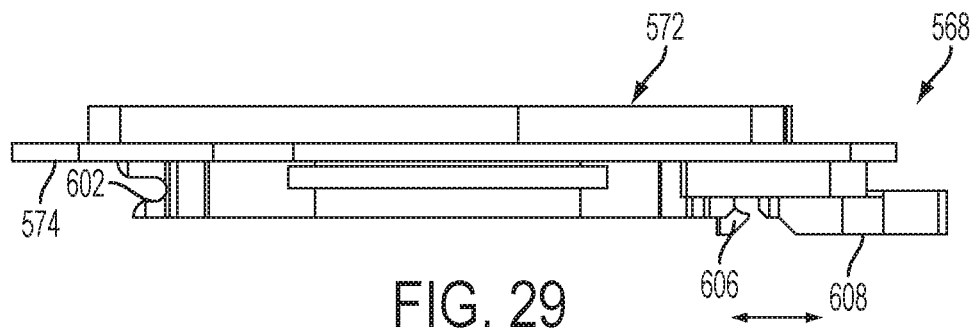
FIGS. 29-31 illustrate additional views of the adapter portion of the instrument drive assembly embodiment of FIG. 26.
Figure 30:
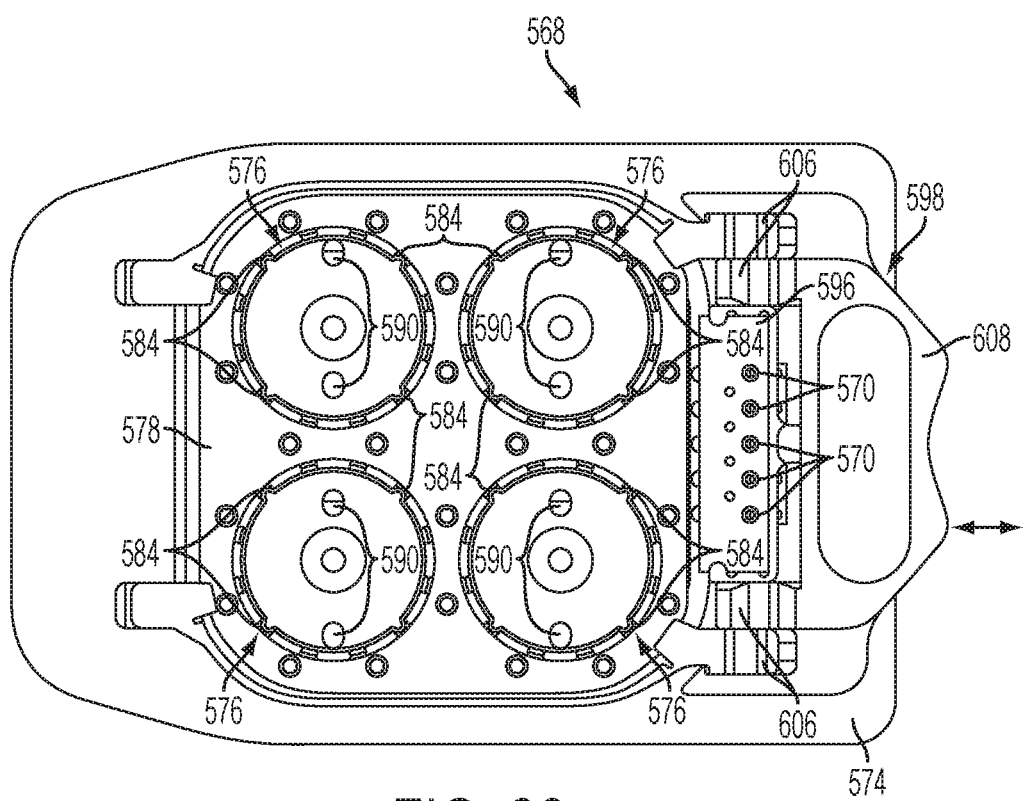
Figure 31:
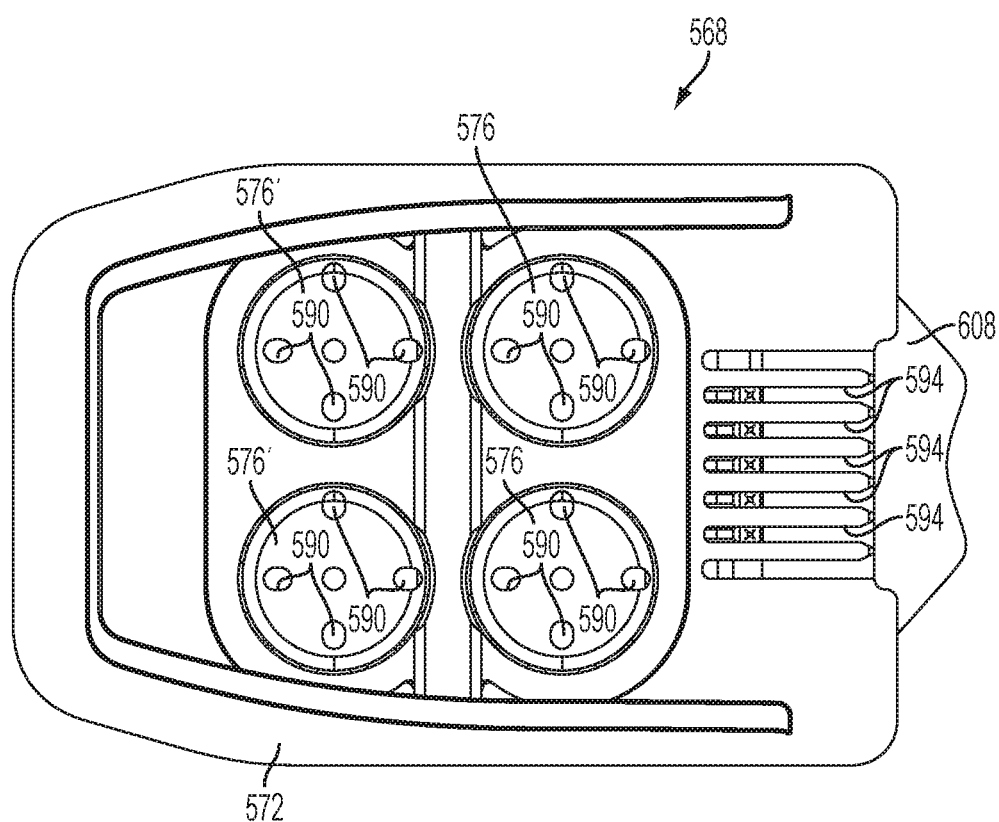

FIGS. 29-31 show additional views of the adapter portion 568 of the instrument drive assembly 546 of FIG. 26. The adapter portion 568 generally includes an instrument side 572 and a holder side 574 (FIG. 29). In various embodiments, a plurality of rotatable bodies 576 are mounted to a floating plate 578 which has a limited range of movement relative to the surrounding adaptor structure normal to the major surfaces of the adaptor 568. Axial movement of the floating plate 578 helps decouple the rotatable bodies 576 from the instrument mounting portion 558 when the levers 580 along the sides of the instrument mounting portion housing 582 are actuated (See FIGS. 24, 25) Other mechanisms/arrangements may be employed for releasably coupling the instrument mounting portion 558 to the adaptor 568. In at least one form, rotatable bodies 576 are resiliently mounted to floating plate 578 by resilient radial members which extend into a circumferential indentation about the rotatable bodies 576. The rotatable bodies 576 can move axially relative to plate 578 by deflection of these resilient structures. When disposed in a first axial position (toward instrument side 572) the rotatable bodies 576 are free to rotate without angular limitation. However, as the rotatable bodies 576 move axially toward instrument side 572, tabs 584 (extending radially from the rotatable bodies 576) laterally engage detents on the floating plates so as to limit angular rotation of the rotatable bodies 576 about their axes.

This limited rotation can be used to help drivingly engage the rotatable bodies 576 with drive pins 586 of a corresponding instrument holder portion 588 of the robotic system, as the drive pins 586 will push the rotatable bodies 576 into the limited rotation position until the pins 586 are aligned with (and slide into) openings 590.

Openings 590 on the instrument side 572 and openings 590 on the holder side 574 of rotatable bodies 576 are configured to accurately align the driven elements 564 (FIGS. 27, 28) of the instrument mounting portion 558 with the drive elements 592 of the instrument holder 588. As described above regarding inner and outer pins 566 of driven elements 564, the openings 590 are at differing distances from the axis of rotation on their respective rotatable bodies 576 so as to ensure that the alignment is not 33 degrees from its intended position. Additionally, each of the openings 590 may be slightly radially elongated so as to fittingly receive the pins 566 in the circumferential orientation. This allows the pins 566 to slide radially within the openings 590 and accommodate some axial misalignment between the instrument 522, 523 and instrument holder 588, while minimizing any angular misalignment and backlash between the drive and driven elements. Openings 590 on the instrument side 572 may be offset by about 90 degrees from the openings 590 (shown in broken lines) on the holder side 574, as can be seen most clearly in FIG. 31.

Various embodiments may further include an array of electrical connector pins 570 located on holder side 574 of adaptor 568, and the instrument side 572 of the adaptor 568 may include slots 594 (FIG. 31) for receiving a pin array (not shown) from the instrument mounting portion 558. In addition to transmitting electrical signals between the surgical instrument 522, 523 and the instrument holder 588, at least some of these electrical connections may be coupled to an adaptor memory device 596 (FIG. 30) by a circuit board of the adaptor 568.

A detachable latch arrangement 598 may be employed to releasably affix the adaptor 568 to the instrument holder 588. As used herein, the term "instrument drive assembly" when used in the context of the robotic system, at least encompasses various embodiments of the adapter 568 and instrument holder 588 and which has been generally designated as 546 in FIG. 26. For example, as can be seen in FIG. 26, the instrument holder 588 may include a first latch pin arrangement 600 that is sized to be received in corresponding clevis slots 602 provided in the adaptor 568. In addition, the instrument holder 588 may further have second latch pins 604 that are sized to be retained in corresponding latch devises 606 in the adaptor 568. See FIG. 30. In at least one form, a latch assembly 608 is movably supported on the adapter 568 and is biasable between a first latched position wherein the latch pins 600 are retained within their respective latch clevis 606 and an unlatched position wherein the second latch pins 604 may be into or removed from the latch devises 606. A spring or springs (not shown) are employed to bias the latch assembly into the latched position. A lip on the instrument side 572 of adaptor 568 may slidably receive laterally extending tabs of instrument mounting housing 582.

As described the driven elements 564 may be aligned with the drive elements 592 of the instrument holder 588 such that rotational motion of the drive elements 592 causes corresponding rotational motion of the driven elements 564. The rotation of the drive elements 592 and driven elements 564 may be electronically controlled, for example, via the robotic arm 612, in response to instructions received from the clinician 502 via a controller 508. The instrument mounting portion 558 may translate rotation of the driven elements 564 into motion of the surgical instrument 522, 523.

Figure 32:
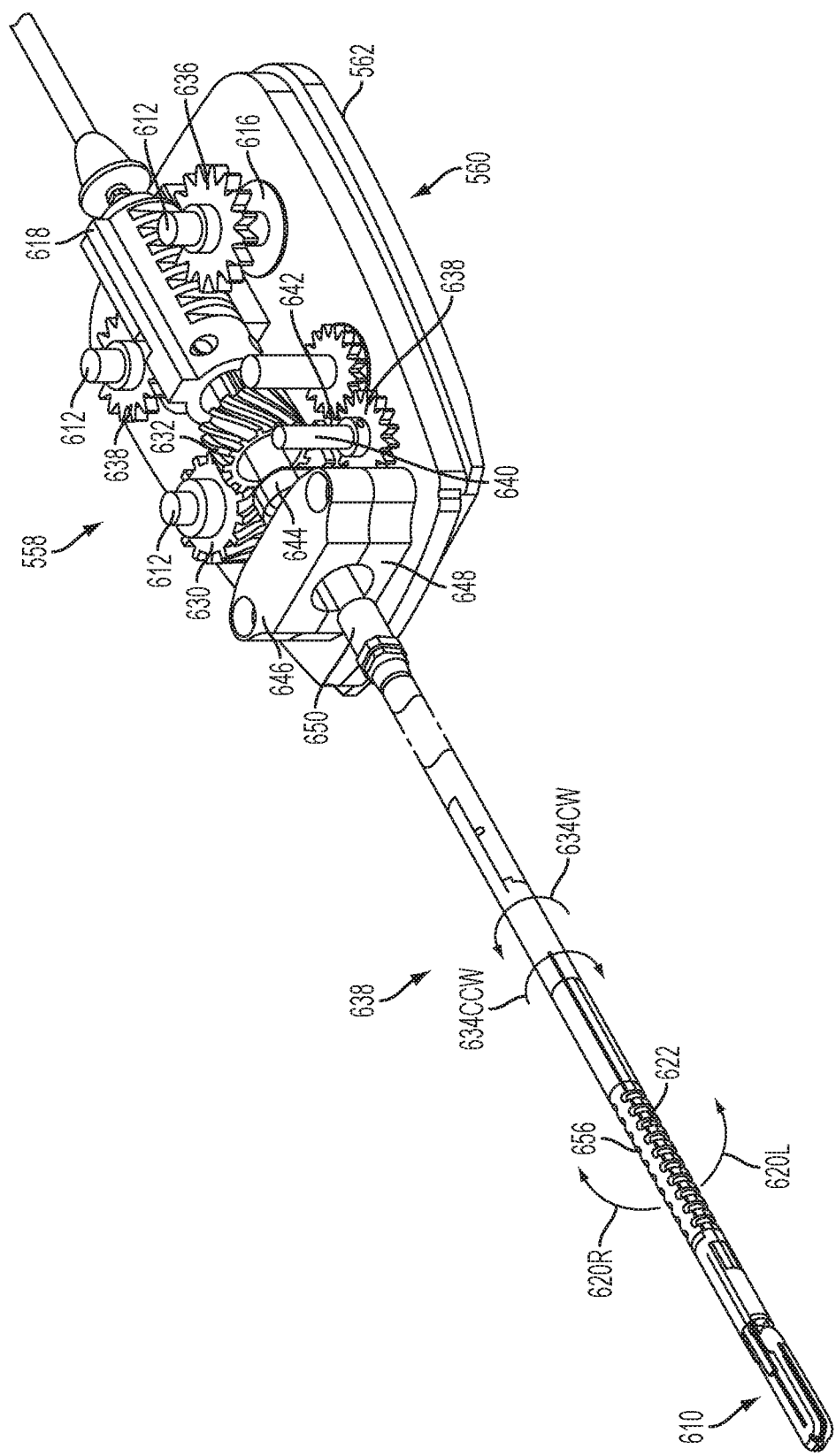
FIGS. 32-34 illustrate one embodiment of the instrument mounting portion of FIGS. 24-25 showing components for translating motion of the driven elements into motion of the surgical instrument.
Figure 33:
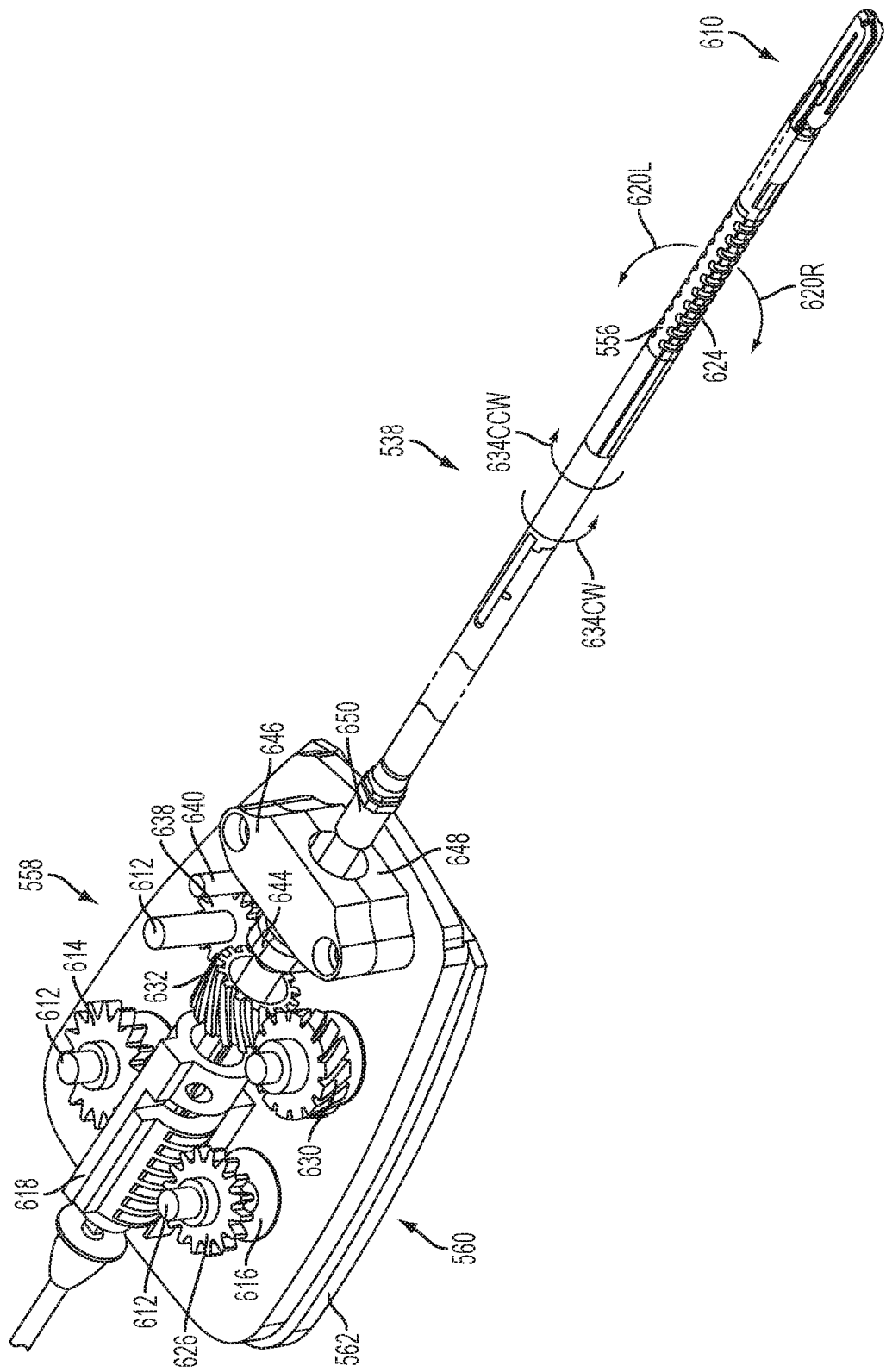
Figure 34:
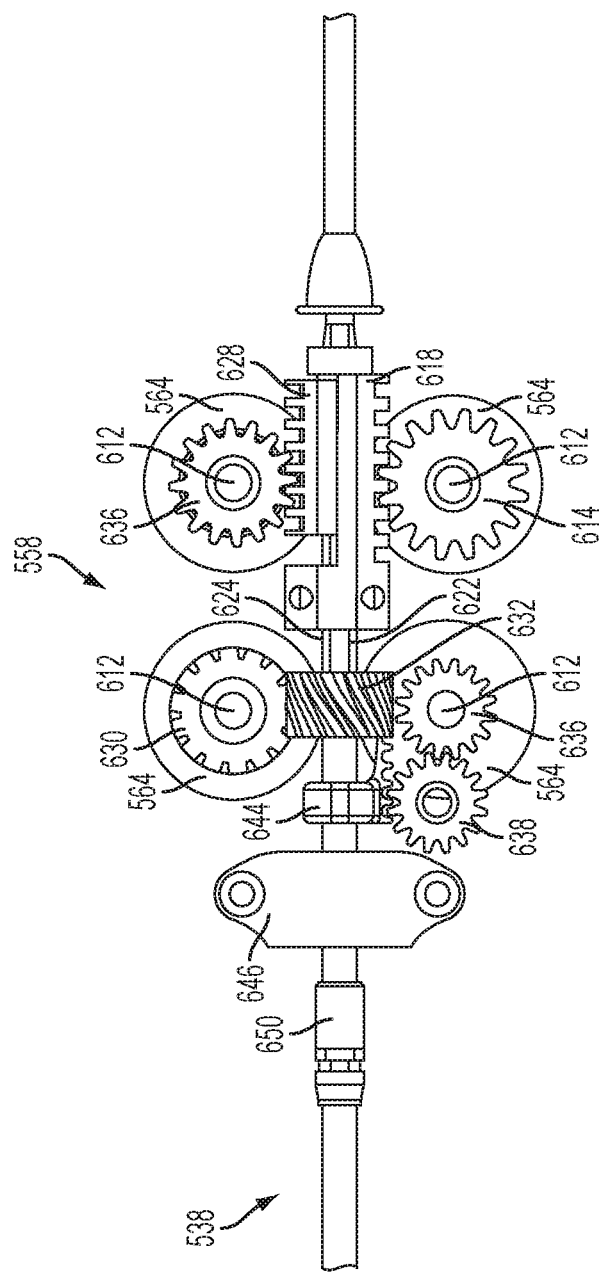

FIGS. 32-34 show one example embodiment of the instrument mounting portion 558 showing components for translating motion of the driven elements 564 into motion of the surgical instrument 522, 523. FIGS. 32-34 show the instrument mounting portion with a shaft 538 having a surgical end effector 610 at a distal end thereof. The end effector 610 may be any suitable type of end effector for performing a surgical task on a patient. For example, the end effector may be configured to provide RF and/or ultrasonic energy to tissue at a surgical site. The shaft 538 may be rotatably coupled to the instrument mounting portion 558 and secured by a top shaft holder 646 and a bottom shaft holder 648 at a coupler 650 of the shaft 538.

In one example embodiment, the instrument mounting portion 558 comprises a mechanism for translating rotation of the various driven elements 564 into rotation of the shaft 538, differential translation of members along the axis of the shaft (e.g., for articulation), and reciprocating translation of one or more members along the axis of the shaft 538 (e.g., for extending and retracting tissue cutting elements such as 555, overtubes and/or other components). In one example embodiment, the rotatable bodies 612 (e.g., rotatable spools) are coupled to the driven elements 564. The rotatable bodies 612 may be formed integrally with the driven elements 564. In some embodiments, the rotatable bodies 612 may be formed separately from the driven elements 564 provided that the rotatable bodies 612 and the driven elements 564 are fixedly coupled such that driving the driven elements 564 causes rotation of the rotatable bodies 612. Each of the rotatable bodies 612 is coupled to a gear train or gear mechanism to provide shaft articulation and rotation and clamp jaw open/close and knife actuation.

In one example embodiment, the instrument mounting portion 558 comprises a mechanism for causing differential translation of two or more members along the axis of the shaft 538. In the example provided in FIGS. 32-34, this motion is used to manipulate articulation joint 556. In the illustrated embodiment, for example, the instrument mounting portion 558 comprises a rack and pinion gearing mechanism to provide the differential translation and thus the shaft articulation functionality. In one example embodiment, the rack and pinion gearing mechanism comprises a first pinion gear 614 coupled to a rotatable body 612 such that rotation of the corresponding driven element 564 causes the first pinion gear 614 to rotate. A bearing 616 is coupled to the rotatable body 612 and is provided between the driven element 564 and the first pinion gear 614. The first pinion gear 614 is meshed to a first rack gear 618 to convert the rotational motion of the first pinion gear 614 into linear motion of the first rack gear 618 to control the articulation of the articulation section 556 of the shaft assembly 538 in a left direction 620L. The first rack gear 618 is attached to a first articulation band 622 (FIG. 32) such that linear motion of the first rack gear 618 in a distal direction causes the articulation section 556 of the shaft assembly 538 to articulate in the left direction 620L. A second pinion gear 626 is coupled to another rotatable body 612 such that rotation of the corresponding driven element 564 causes the second pinion gear 626 to rotate. A bearing 616 is coupled to the rotatable body 612 and is provided between the driven element 564 and the second pinion gear 626. The second pinion gear 626 is meshed to a second rack gear 628 to convert the rotational motion of the second pinion gear 626 into linear motion of the second rack gear 628 to control the articulation of the articulation section 556 in a right direction 620R. The second rack gear 628 is attached to a second articulation band 624 (FIG. 33) such that linear motion of the second rack gear 628 in a distal direction causes the articulation section 556 of the shaft assembly 538 to articulate in the right direction 620R. Additional bearings may be provided between the rotatable bodies and the corresponding gears. Any suitable bearings may be provided to support and stabilize the mounting and reduce rotary friction of shaft and gears, for example.

In one example embodiment, the instrument mounting portion 558 further comprises a mechanism for translating rotation of the driven elements 564 into rotational motion about the axis of the shaft 538. For example, the rotational motion may be rotation of the shaft 538 itself. In the illustrated embodiment, a first spiral worm gear 630 coupled to a rotatable body 612 and a second spiral worm gear 632 coupled to the shaft assembly 538. A bearing 616 (FIG. 17) is coupled to a rotatable body 612 and is provided between a driven element 564 and the first spiral worm gear 630. The first spiral worm gear 630 is meshed to the second spiral worm gear 632, which may be coupled to the shaft assembly 538 and/or to another component of the instrument 522, 523 for which longitudinal rotation is desired. Rotation may be caused in a clockwise (CW) and counter-clockwise (CCW) direction based on the rotational direction of the first and second spiral worm gears 630, 632. Accordingly, rotation of the first spiral worm gear 630 about a first axis is converted to rotation of the second spiral worm gear 632 about a second axis, which is orthogonal to the first axis. As shown in FIGS. 32-33, for example, a CW rotation of the second spiral worm gear 632 results in a CW rotation of the shaft assembly 538 in the direction indicated by 634CW. A CCW rotation of the second spiral worm gear 632 results in a CCW rotation of the shaft assembly 538 in the direction indicated by 634CCW. Additional bearings may be provided between the rotatable bodies and the corresponding gears. Any suitable bearings may be used to support and stabilize the mounting and reduce rotary friction of shaft and gears, for example.

In one example embodiment, the instrument mounting portion 558 comprises a mechanism for generating reciprocating translation of one or more members along the axis of the shaft 538. Such translation may be used, for example to drive a tissue cutting element, such as 555, drive an overtube for closure and/or articulation of the end effector 610, etc. In the illustrated embodiment, for example, a rack and pinion gearing mechanism may provide the reciprocating translation. A first gear 636 is coupled to a rotatable body 612 such that rotation of the corresponding driven element 564 causes the first gear 636 to rotate in a first direction. A second gear 638 is free to rotate about a post 640 formed in the instrument mounting plate 562. The first gear 636 is meshed to the second gear 638 such that the second gear 638 rotates in a direction that is opposite of the first gear 636. In one example embodiment, the second gear 638 is a pinion gear meshed to a rack gear 642, which moves in a liner direction. The rack gear 642 is coupled to a translating block 644, which may translate distally and proximally with the rack gear 642. The translation block 644 may be coupled to any suitable component of the shaft assembly 538 and/or the end effector 610 so as to provide reciprocating longitudinal motion. For example, the translation block 644 may be mechanically coupled to the tissue cutting element 555 of the RF surgical device 523. In some embodiments, the translation block 644 may be coupled to an overtube, or other component of the end effector 610 or shaft 538.

Figure 35:
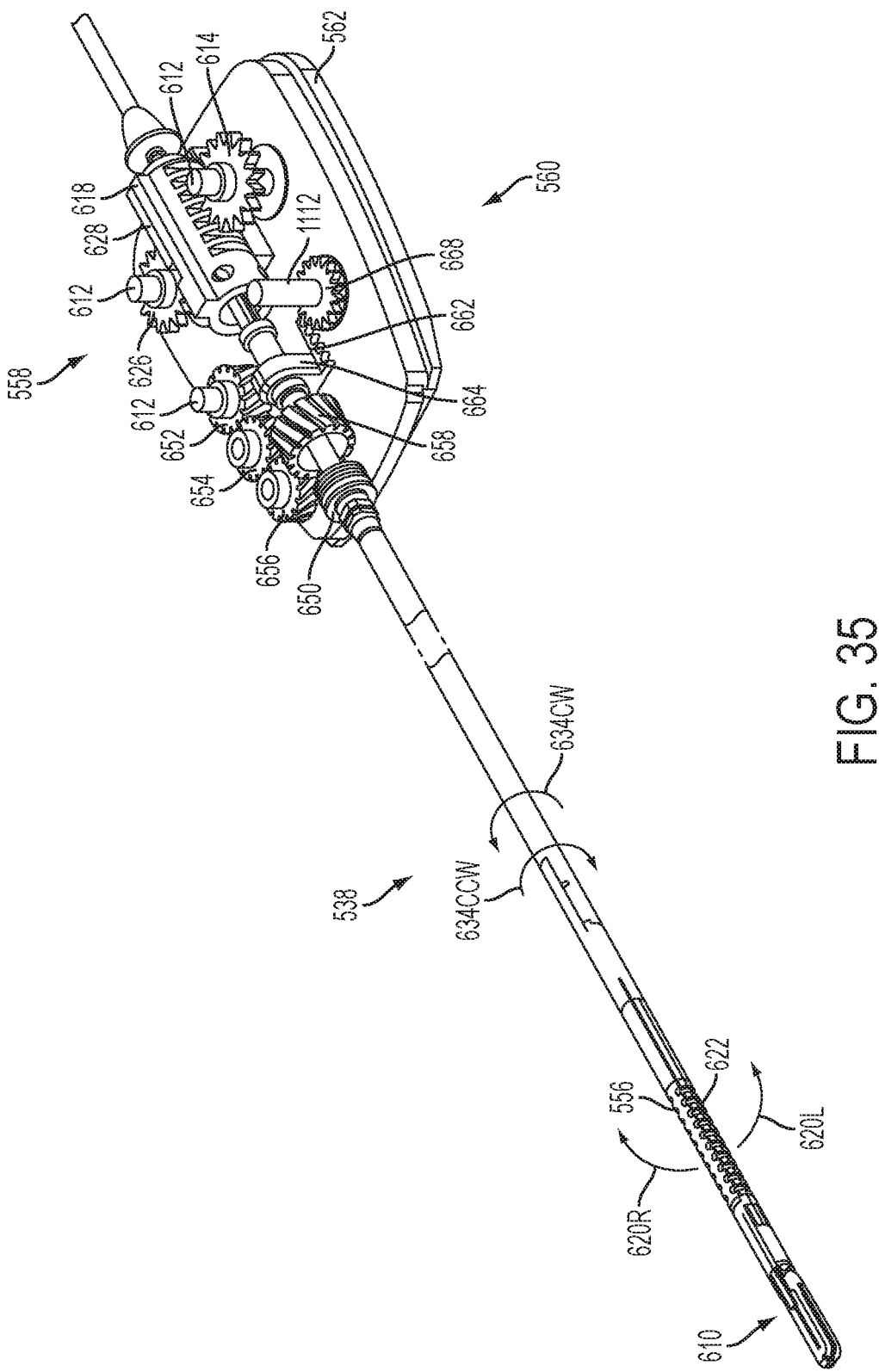
FIGS. 35-37 illustrate an alternate embodiment of the instrument mounting portion of FIGS. 24-25 showing an alternate example mechanism for translating rotation of the driven elements into rotational motion about the axis of the shaft and an alternate example mechanism for generating reciprocating translation of one or more members along the axis of the shaft 538.
Figure 36:
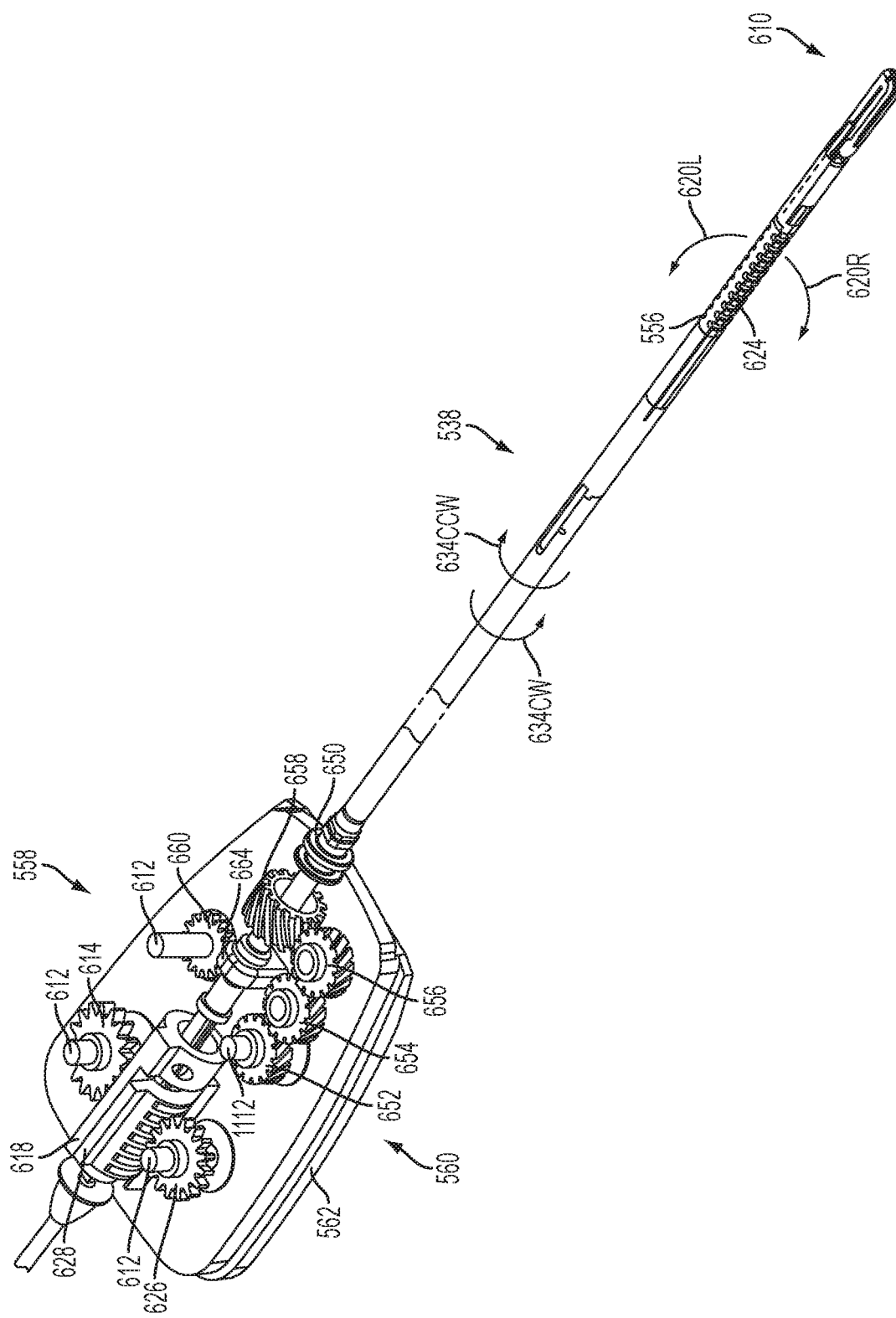
Figure 37:
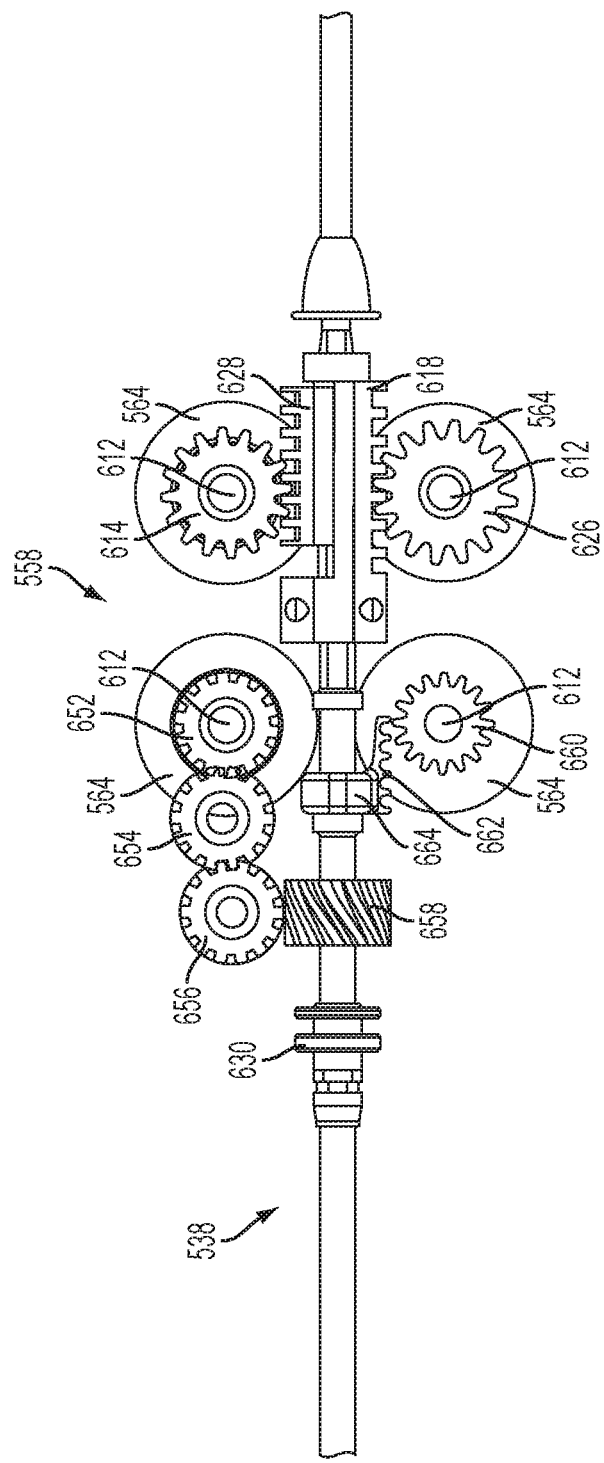

FIGS. 35-37 illustrate an alternate embodiment of the instrument mounting portion 558 showing an alternate example mechanism for translating rotation of the driven elements 564 into rotational motion about the axis of the shaft 538 and an alternate example mechanism for generating reciprocating translation of one or more members along the axis of the shaft 538. Referring now to the alternate rotational mechanism, a first spiral worm gear 652 is coupled to a second spiral worm gear 654, which is coupled to a third spiral worm gear 656. Such an arrangement may be provided for various reasons including maintaining compatibility with existing robotic systems 1000 and/or where space may be limited. The first spiral worm gear 652 is coupled to a rotatable body 612. The third spiral worm gear 656 is meshed with a fourth spiral worm gear 658 coupled to the shaft assembly 538. A bearing 760 is coupled to a rotatable body 612 and is provided between a driven element 564 and the first spiral worm gear 738. Another bearing 760 is coupled to a rotatable body 612 and is provided between a driven element 564 and the third spiral worm gear 652. The third spiral worm gear 652 is meshed to the fourth spiral worm gear 658, which may be coupled to the shaft assembly 538 and/or to another component of the instrument 522, 523 for which longitudinal rotation is desired. Rotation may be caused in a CW and a CCW direction based on the rotational direction of the spiral worm gears 656, 658. Accordingly, rotation of the third spiral worm gear 656 about a first axis is converted to rotation of the fourth spiral worm gear 658 about a second axis, which is orthogonal to the first axis. As shown in FIGS. 36 and 37, for example, the fourth spiral worm gear 658 is coupled to the shaft 538, and a CW rotation of the fourth spiral worm gear 658 results in a CW rotation of the shaft assembly 538 in the direction indicated by 634CW. A CCW rotation of the fourth spiral worm gear 658 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Referring now to the alternate example mechanism for generating reciprocating translation of one or more members along the axis of the shaft 538, the instrument mounting portion 558 comprises a rack and pinion gearing mechanism to provide reciprocating translation along the axis of the shaft 538 (e.g., translation of a tissue cutting element 555 of the RF surgical device 523). In one example embodiment, a third pinion gear 660 is coupled to a rotatable body 612 such that rotation of the corresponding driven element 564 causes the third pinion gear 660 to rotate in a first direction. The third pinion gear 660 is meshed to a rack gear 662, which moves in a linear direction. The rack gear 662 is coupled to a translating block 664. The translating block 664 may be coupled to a component of the device 522, 523, such as, for example, the tissue cutting element 555 of the RF surgical device and/or an overtube or other component which is desired to be translated longitudinally.

Figure 38:
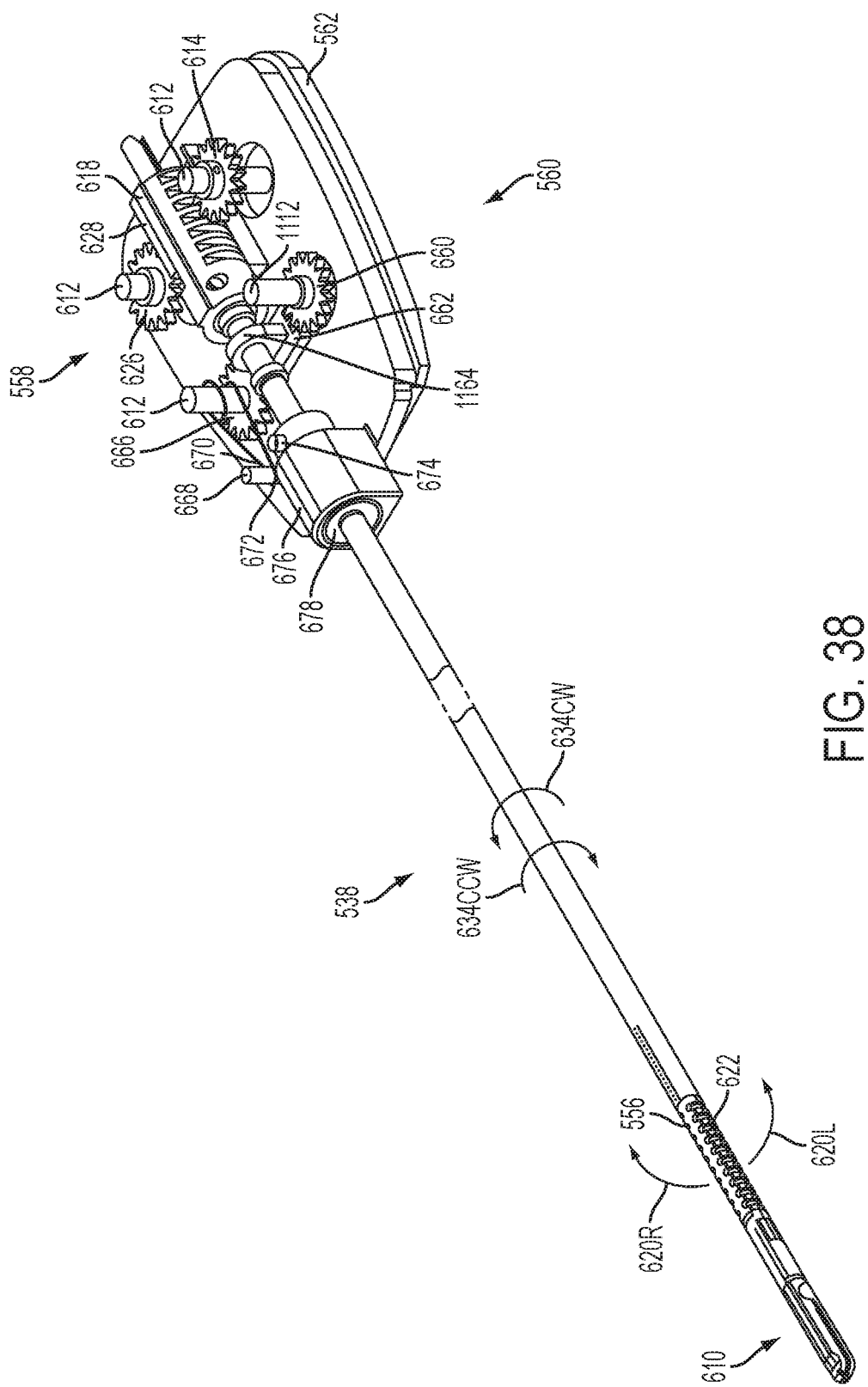
FIGS. 38-42 illustrate an alternate embodiment of the instrument mounting portion FIGS. 24-25 showing another alternate example mechanism for translating rotation of the driven elements into rotational motion about the axis of the shaft.
Figure 39:
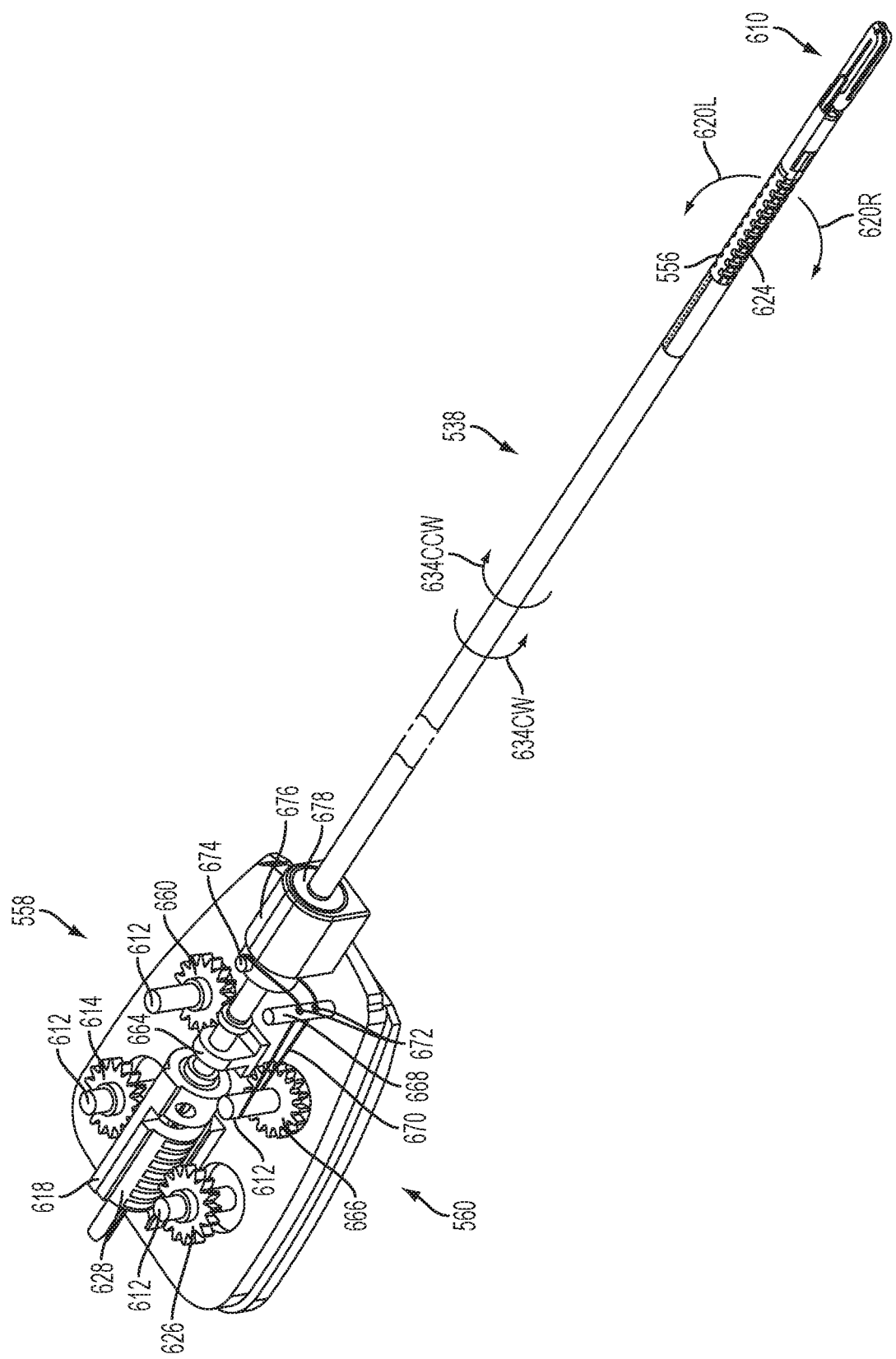
Figure 40:
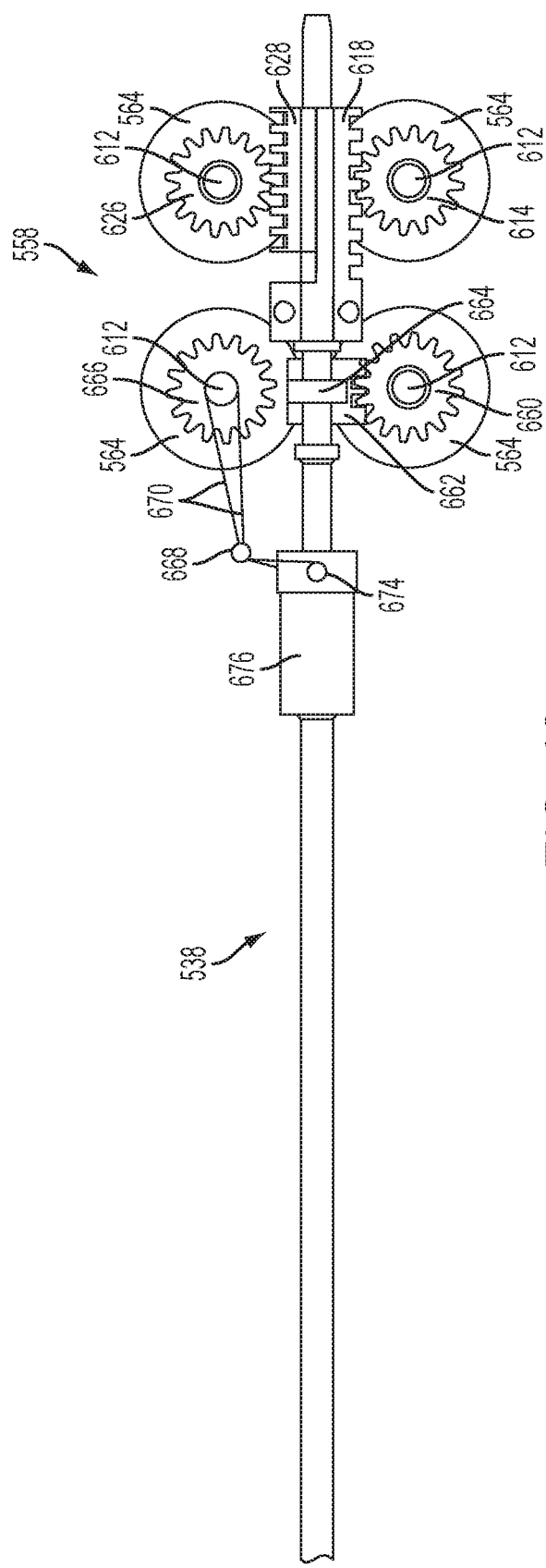
Figure 41:
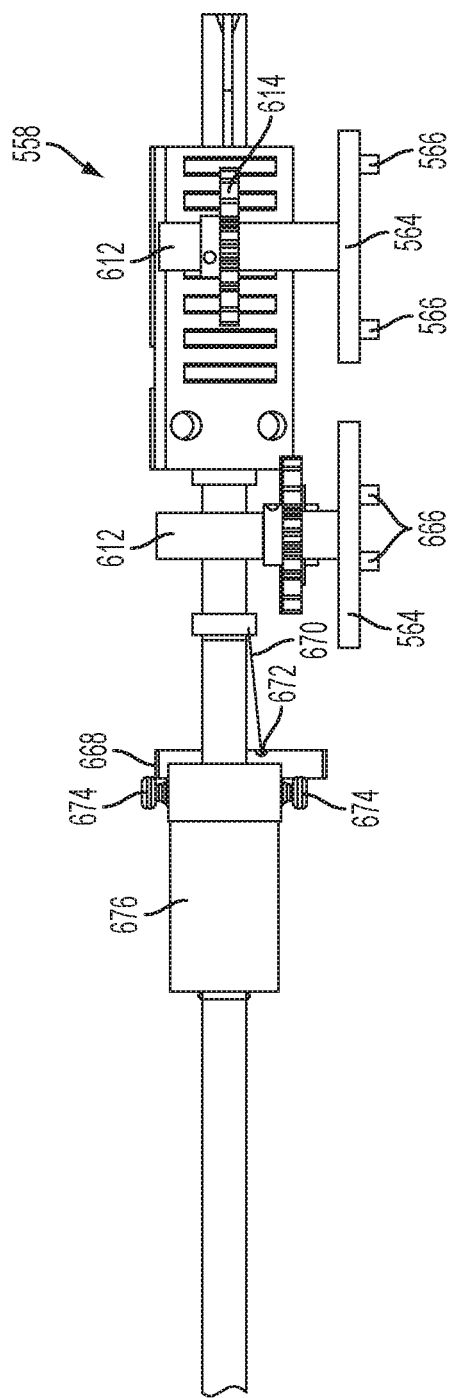
Figure 42:
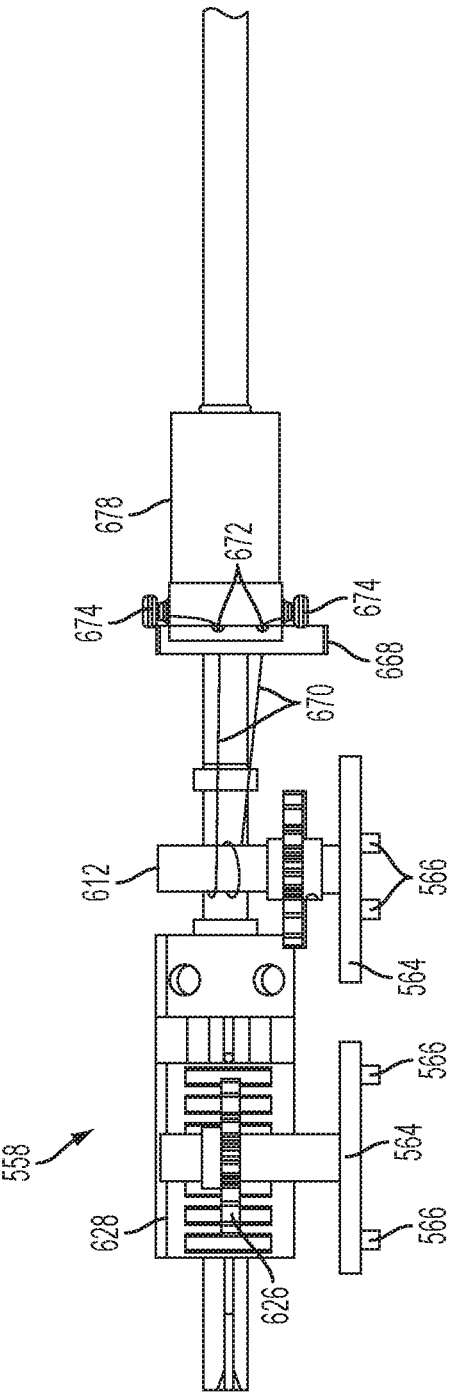
Figure 43:
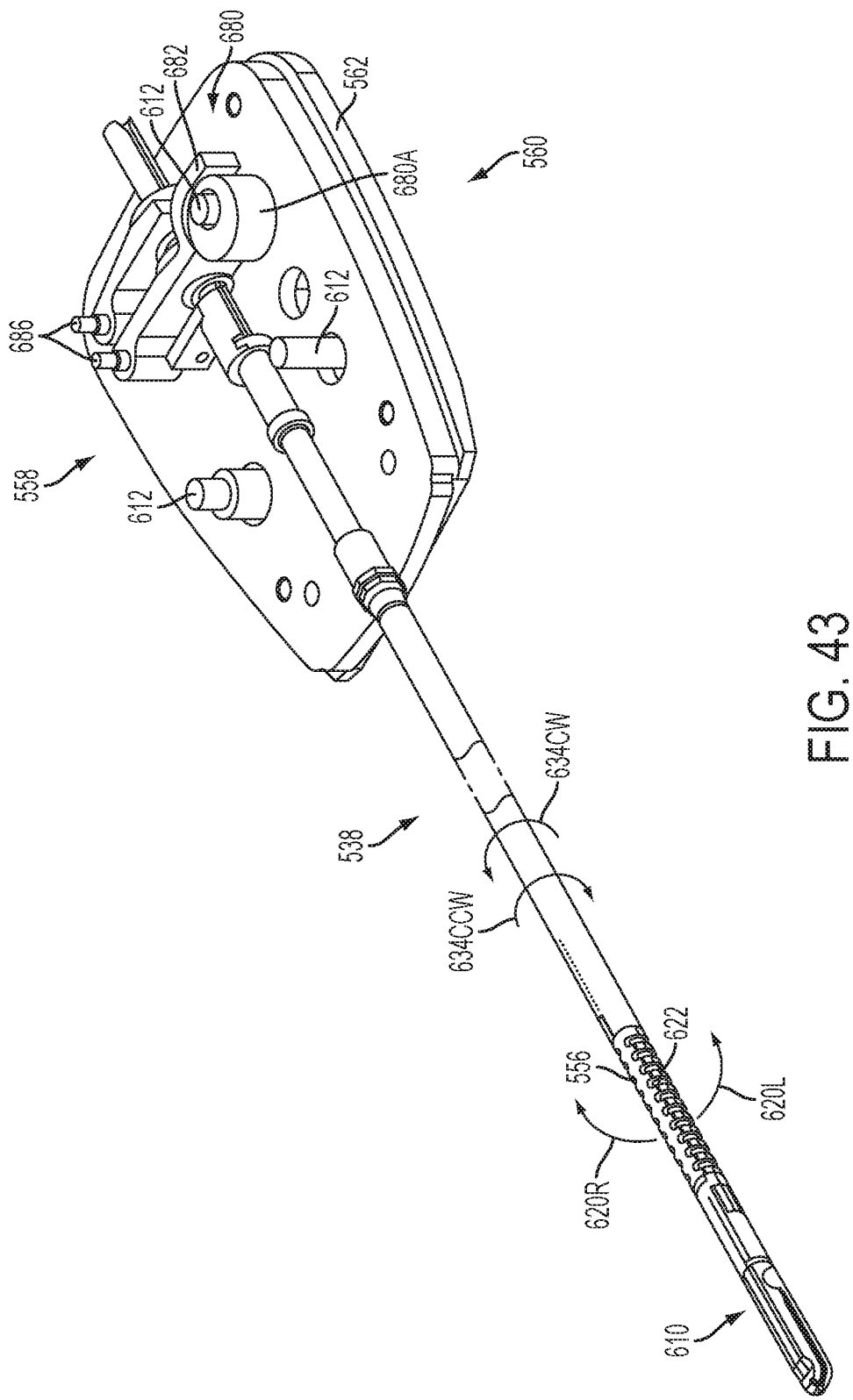
Figure 44:
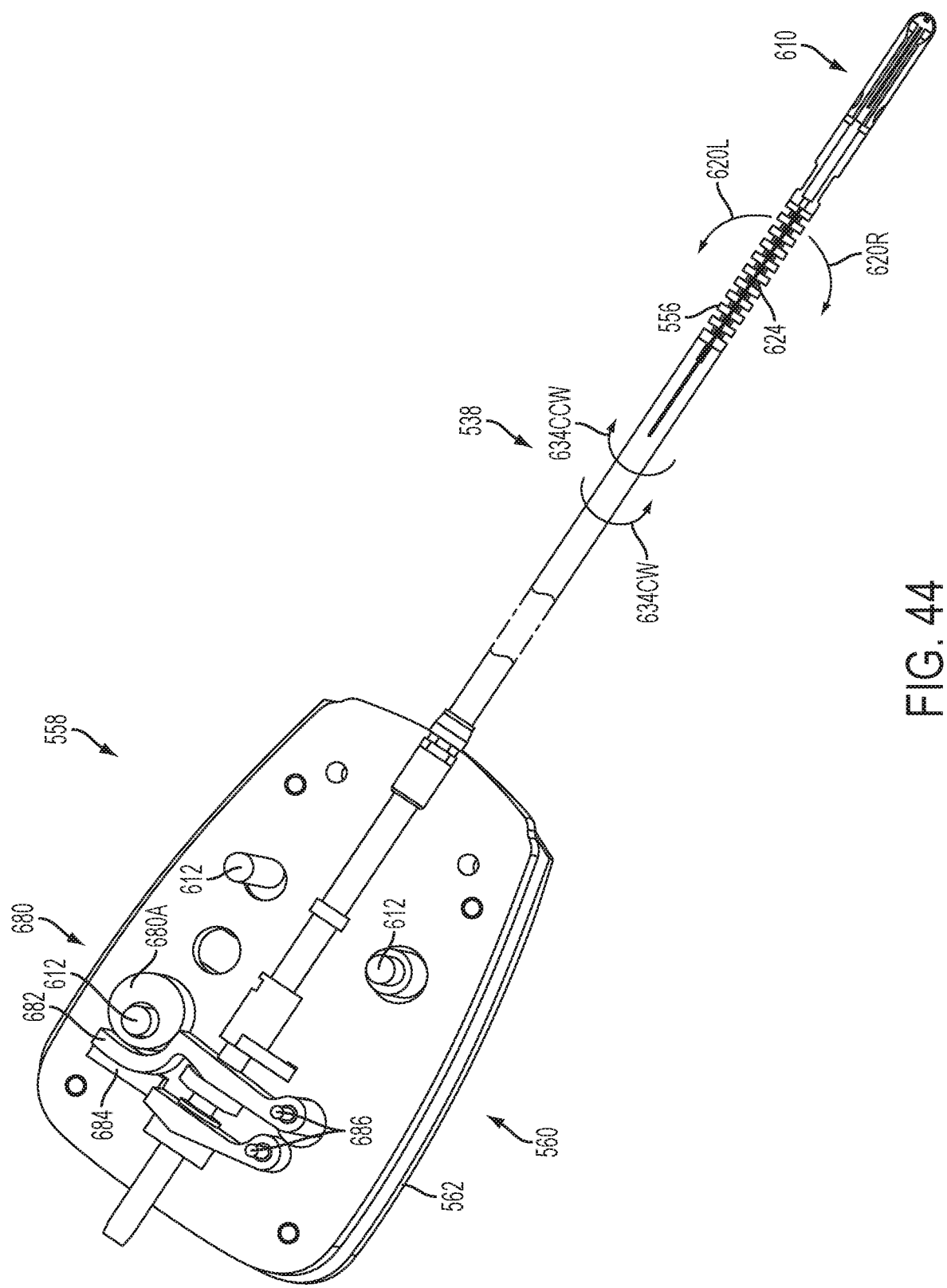
Figure 45:
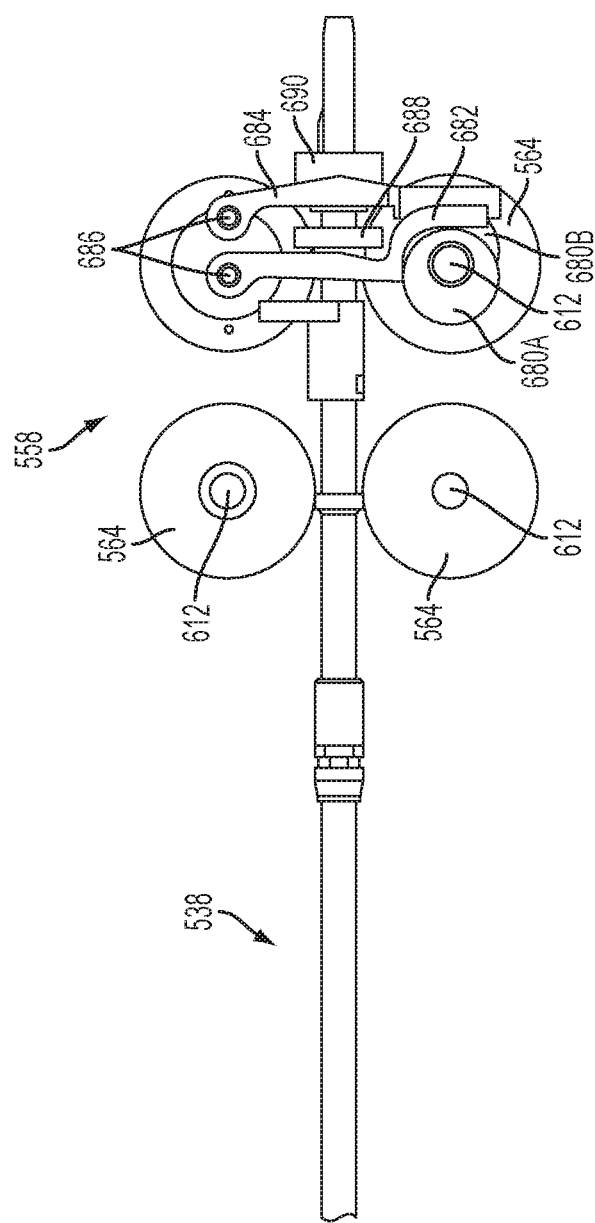

FIGS. 38-42 illustrate an alternate embodiment of the instrument mounting portion 558 showing another alternate example mechanism for translating rotation of the driven elements 564 into rotational motion about the axis of the shaft 538. In FIGS. 38-42, the shaft 538 is coupled to the remainder of the mounting portion 558 via a coupler 676 and a bushing 678. A first gear 666 coupled to a rotatable body 612, a fixed post 668 comprising first and second openings 672, first and second rotatable pins 674 coupled to the shaft assembly, and a cable 670 (or rope). The cable is wrapped around the rotatable body 612. One end of the cable 670 is located through a top opening 672 of the fixed post 668 and fixedly coupled to a top rotatable pin 674. Another end of the cable 670 is located through a bottom opening 672 of the fixed post 668 and fixedly coupled to a bottom rotating pin 674. Such an arrangement is provided for various reasons including maintaining compatibility with existing robotic systems 1000 and/or where space may be limited. Accordingly, rotation of the rotatable body 612 causes the rotation about the shaft assembly 538 in a CW and a CCW direction based on the rotational direction of the rotatable body 612 (e.g., rotation of the shaft 538 itself). Accordingly, rotation of the rotatable body 612 about a first axis is converted to rotation of the shaft assembly 538 about a second axis, which is orthogonal to the first axis. As shown in FIGS. 38-39, for example, a CW rotation of the rotatable body 612 results in a CW rotation of the shaft assembly 538 in the direction indicated by 634CW. A CCW rotation of the rotatable body 612 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Figure 46A:
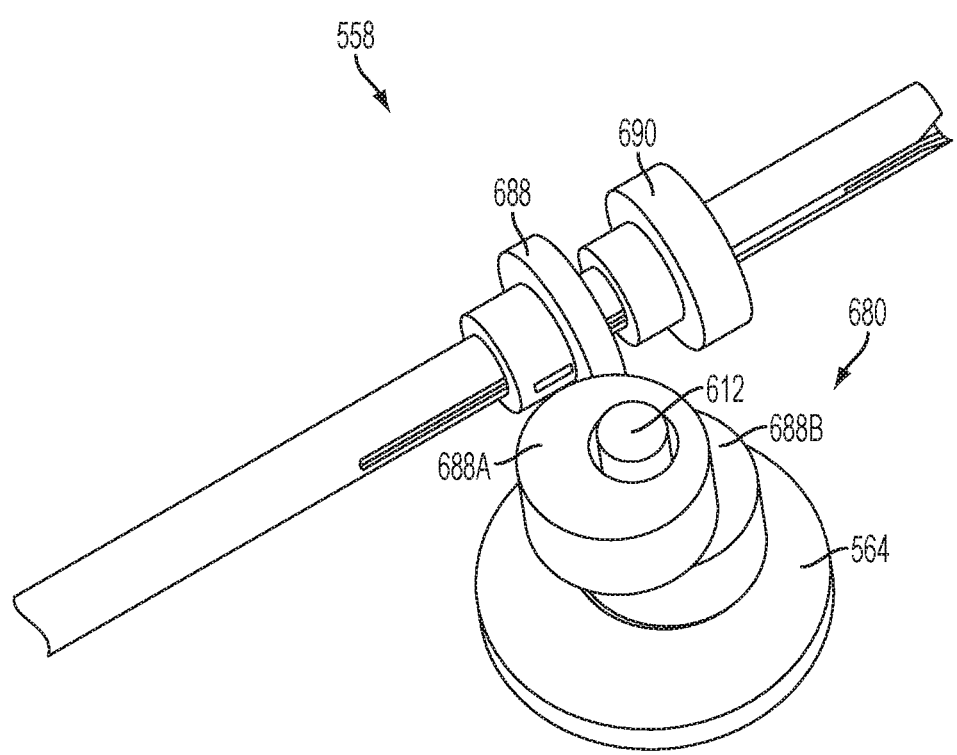

FIGS. 43-46A illustrate an alternate embodiment of the instrument mounting portion 558 showing an alternate example mechanism for differential translation of members along the axis of the shaft 538 (e.g., for articulation). For example, as illustrated in FIGS. 43-46A, the instrument mounting portion 558 comprises a double cam mechanism 680 to provide the shaft articulation functionality. In one example embodiment, the double cam mechanism 680 comprises first and second cam portions 680A, 680B. First and second follower arms 682, 684 are pivotally coupled to corresponding pivot spools 686. As the rotatable body 612 coupled to the double cam mechanism 680 rotates, the first cam portion 680A acts on the first follower arm 682 and the second cam portion 680B acts on the second follower arm 684. As the cam mechanism 680 rotates the follower arms 682, 684 pivot about the pivot spools 686. The first follower arm 682 may be attached to a first member that is to be differentially translated (e.g., the first articulation band 622). The second follower arm 684 is attached to a second member that is to be differentially translated (e.g., the second articulation band 624). As the top cam portion 680A acts on the first follower arm 682, the first and second members are differentially translated. In the example embodiment where the first and second members are the respective articulation bands 622 and 624, the shaft assembly 538 articulates in a left direction 620L. As the bottom cam portion 680B acts of the second follower arm 684, the shaft assembly 538 articulates in a right direction 620R. In some example embodiments, two separate bushings 688, 690 are mounted beneath the respective first and second follower arms 682, 684 to allow the rotation of the shaft without affecting the articulating positions of the first and second follower arms 682, 684. For articulation motion, these bushings reciprocate with the first and second follower arms 682, 684 without affecting the rotary position of the jaw 902. FIG. 46 shows the bushings 688, 690 and the dual cam assembly 680, including the first and second cam portions 680B, 680B, with the first and second follower arms 682, 684 removed to provide a more detailed and clearer view.

Figure 46B:
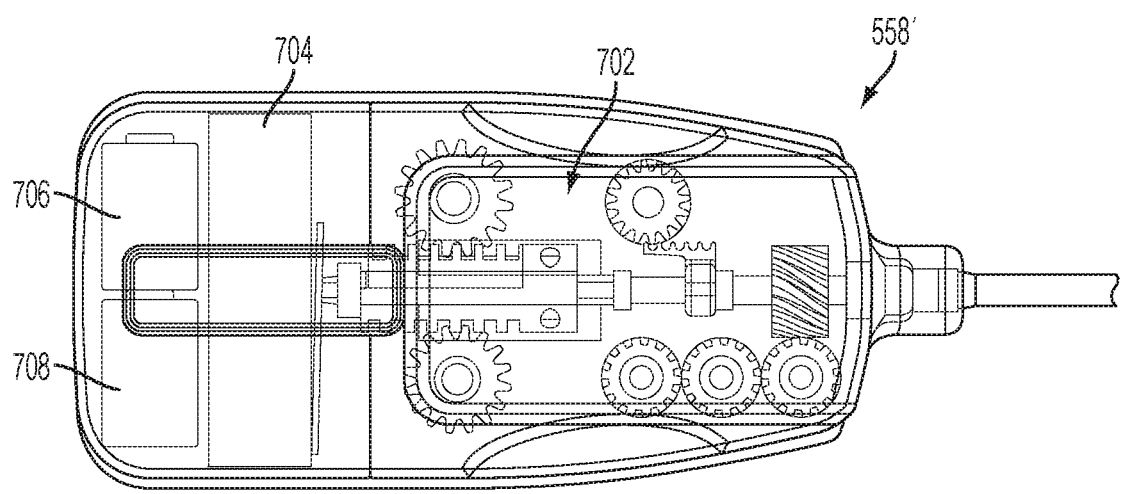
FIGS. 46B-46C illustrate one embodiment of a tool mounting portion comprising internal power and energy sources.
Figure 46C:
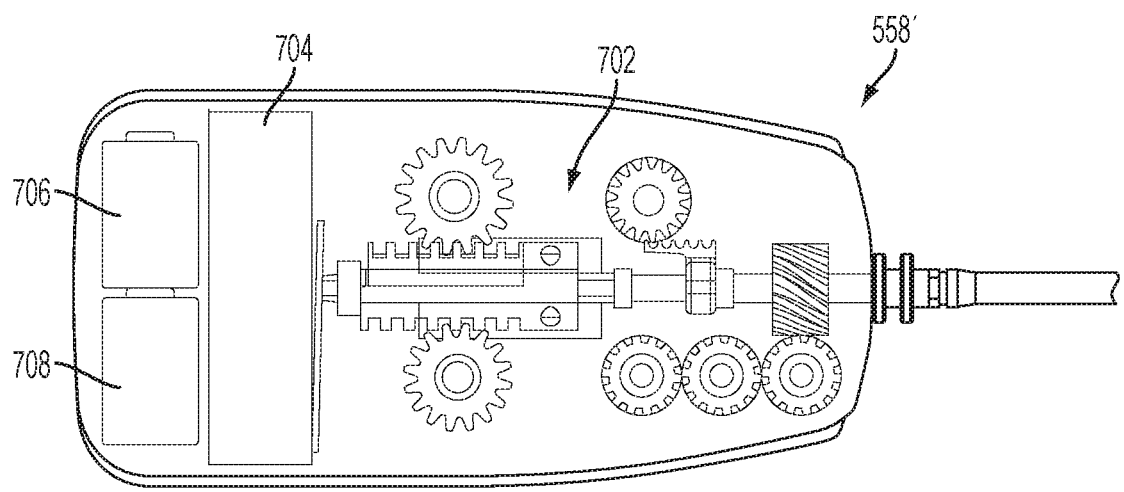

In various embodiments, the instrument mounting portion 558 may additionally comprise internal energy sources for driving electronics and provided desired ultrasonic and/or RF frequency signals to surgical tools. FIGS. 46B-46C illustrate one embodiment of a tool mounting portion 558' comprising internal power and energy sources. For example, surgical instruments (e.g., instruments 522, 523) mounted utilizing the tool mounting portion 558' need not be wired to an external generator or other power source. Instead, the functionality of the various generators 20, 320 described herein may be implemented on board the mounting portion 558.

As illustrated in FIGS. 46B-46C, the instrument mounting portion 558' may comprise a distal portion 702. The distal portion 702 may comprise various mechanisms for coupling rotation of drive elements 612 to end effectors of the various surgical instruments 522, 523, for example, as described herein above. Proximal of the distal portion 702, the instrument mounting portion 558' comprises an internal direct current (DC) energy source and an internal drive and control circuit 704. In the illustrated embodiment, the energy source comprises a first and second battery 706, 708. In other respects, the tool mounting portion 558' is similar to the various embodiments of the tool mounting portion 558 described herein above.

The control circuit 704 may operate in a manner similar to that described above with respect to generators 20, 320. For example, when an ultrasonic instrument 522 is utilized, the control circuit 704 may provide an ultrasonic drive signal in a manner similar to that described above with respect to generator 20. Also, for example, when an RF instrument 523 or ultrasonic instrument 522 capable of providing a therapeutic or non-therapeutic RF signal is used, the control circuit 704 may provide an RF drive signal, for example, as described herein above with respect to the module 23 of generator 20 and/or the generator 300. In some embodiments, the control circuit 704 may be configured in a manner similar to that of the control circuit 440 described herein above with respect to FIGS. 18B-18C.

Figure 47:
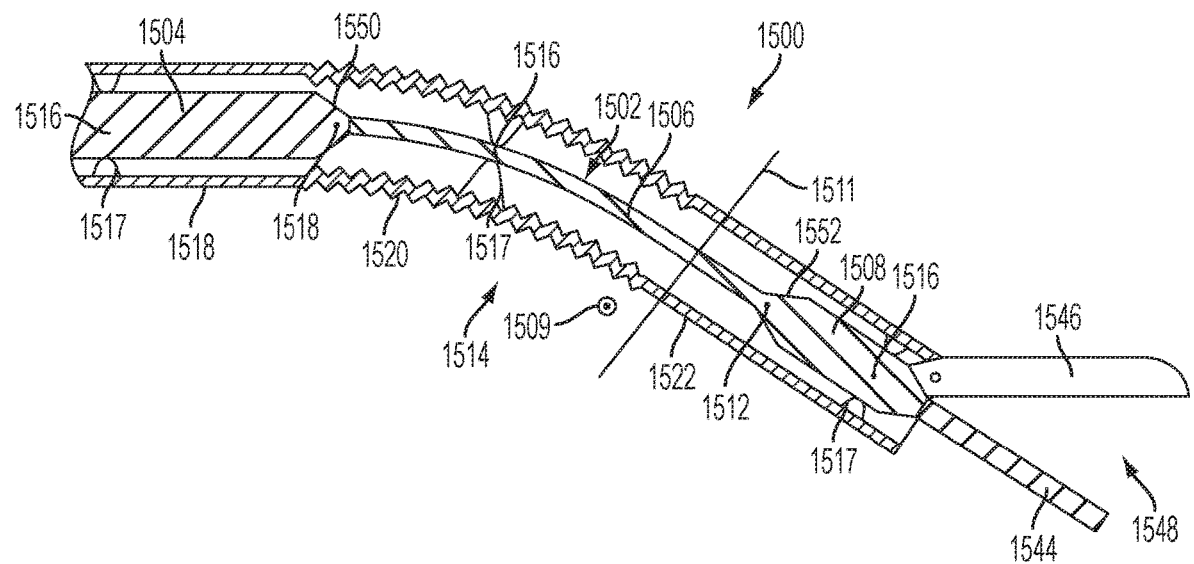
FIG. 47 illustrates a schematic cross-sectional view of a portion of one example embodiment of an ultrasonic medical instrument comprising first, second and third waveguide portions, where the second waveguide portion is substantially ½ of a resonant-longitudinal-wavelength long.

Various embodiments described herein comprise an articulatable shaft. When using an articulatable shaft, components running through the shaft from the end effector must be flexible, so as to flex when the shaft articulates. In various embodiments, this can be accomplished by utilizing waveguides that have flexible portions. For example, FIG. 47 illustrates a schematic cross-sectional view of a portion of one example embodiment of an ultrasonic medical instrument 1500 comprising first, second and third waveguide portions. In FIG. 47, the hand piece and the sheath-articulation control knobs, etc. of the ultrasonic medical instrument 1500 are omitted for clarity. In the example embodiment shown in FIG. 47, the ultrasonic medical instrument 1500 comprises a medical ultrasonic waveguide 1502 for transmitting ultrasonic energy from a transducer (not shown in FIG. 47) to an ultrasonic blade 1544. The medical ultrasonic waveguide 1502 has a length and includes first, second and third waveguide portions 1504, 1506 and 1508. The second waveguide portion 1506 is located lengthwise between the first and third waveguide portions 1504 and 1508; the first waveguide portion 1504 is located proximal the second waveguide portion 1506; and the third waveguide portion 1508 is located distal the second waveguide portion 1506. The first and third waveguide portions 1504 and 1508 each have a larger transverse area and the second waveguide portion 1506 has a smaller transverse area. The second waveguide portion 1506 is more bendable than either of the first and third waveguide portions 1504 and 1508. It is further noted that ultrasonic vibration can be any one, or any combination, of longitudinal, transverse, and torsional vibration. In some embodiments, the section 1506 may have a circular cross-section (e.g., a uniform cross-sectional radius).

Figure 47A:
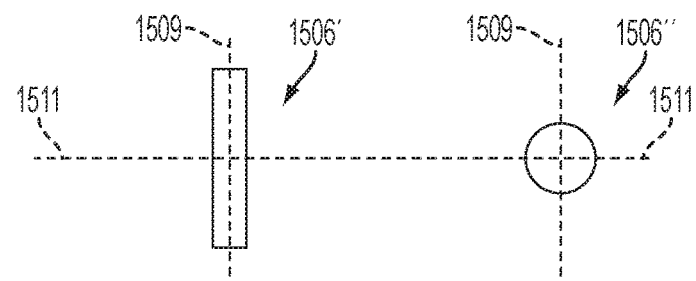
FIG. 47A illustrates cross sections for two example embodiments of the second waveguide portion of FIG. 47.

In some embodiments the second bendable waveguide portion 1506 may not have a uniform cross-sectional radius. For example, FIG. 47A illustrates cross sections for two example embodiments of the waveguide portion 1506. The waveguide portion 1506' is illustrated in relation to two axes 1509, 1511, also shown in FIG. 47. In various embodiments, the waveguide portion 1506' may have a cross sectional length along axis 1511 that is less than its cross sectional dimension along axis 1509. In some embodiments, the cross sectional length along the axis 1509 may be equal to the cross sectional length of the other waveguide portions 1504, 1506. The waveguide portion 1506' may be bendable along the axis 1509. Referring now to waveguide portion 1506", its cross sectional lengths along the axis 1509, 1511 may be the same, providing the waveguide portion 1506" with a greater range of directions for bending.

In some example embodiments, the medical ultrasonic waveguide 1502 is a monolithic (e.g., the blade portion 1544 is integral to the waveguide 1502). Also, in some example embodiments, the medical ultrasonic waveguide 1502 includes first and second longitudinal vibration antinodes 1510 and 1512. The first waveguide portion 1504 may transition to the second waveguide portion 1506 proximate the first longitudinal vibration antinode 1510; and the second waveguide portion 1506 may transition to the third waveguide portion 1508 proximate the second longitudinal vibration antinode 1512. In some example embodiments, as illustrated by FIG. 47, the second waveguide portion 1506 is substantially ½ of a resonant-longitudinal-wavelength long.

In one example application of the embodiment of FIG. 47, the ultrasonic medical instrument 1500 also includes a user-actuated articulated sheath 1514 which surrounds the medical ultrasonic waveguide 1502. In various example embodiments, the medical ultrasonic waveguide 1502 includes three (meaning at least three) longitudinal vibration nodes 1516 located, one each, on the first, second and third waveguide portions 1504, 1506 and 1508. It is noted that one or more additional longitudinal vibration nodes may, or may not, be present between any one or two of the three longitudinal vibration nodes 1516. In one modification, the sheath 1514 contacts (e.g., directly contacts or indirectly contacts through at least one intervening member 1517 such as a silicone intervening member) the first, second and third waveguide portions 1504, 1506 and 1508 at a corresponding one of the three longitudinal vibration nodes 1516. In one example, the sheath 1514 includes a rigid first sheath portion 1518 contacting the first waveguide portion 1504 at the first longitudinal vibration node (the leftmost node 1516 of FIG. 47), a flexible second sheath portion 1520 contacting the second waveguide portion 1506 at the second longitudinal vibration node (the middle node 1516 of FIG. 47), and a rigid third sheath portion 1522 contacting the third waveguide portion 1508 at the third longitudinal vibration node (the rightmost node 1516 of FIG. 47). In some example embodiments, the sheath 1514 has only two articulation positions (e.g., straight and fully articulated). In other example embodiments, the sheath 1514 has a number of intermediate bent positions between a straight position and a fully articulated position depending on the number of energy efficient curves the waveguide 1502 can be formed to. In some example embodiments, such energy efficient curves minimize vibrational energy going into non-longitudinal vibrational modes.

Figure 48:
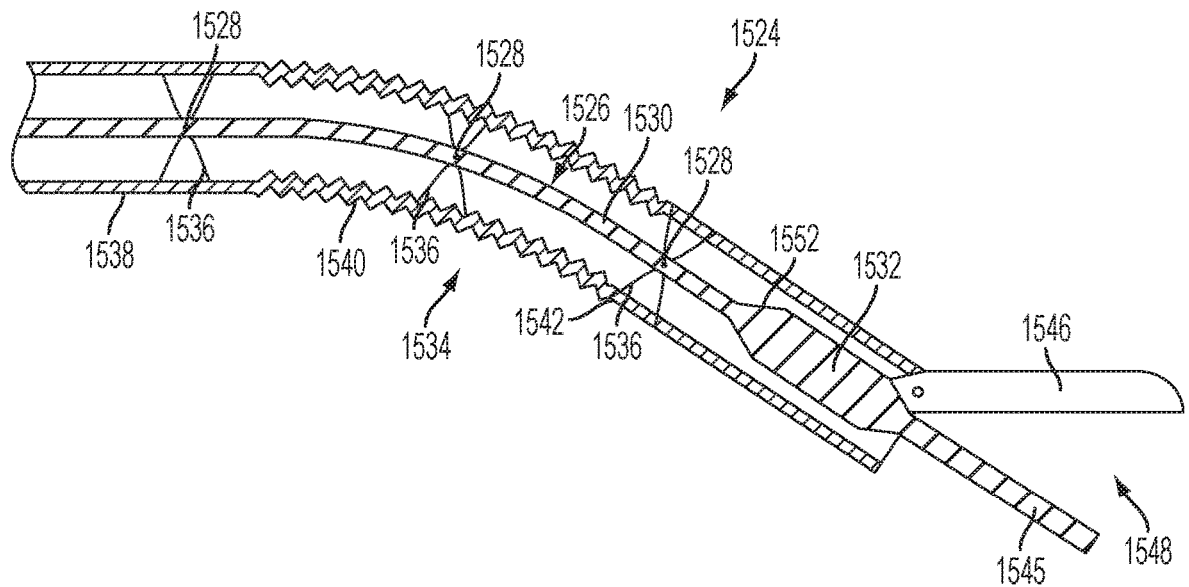
FIG. 48 illustrates a schematic cross-sectional view of a portion of one example embodiment of an ultrasonic medical instrument comprising first and second waveguide portions, where the first waveguide portion spans multiple ½ resonant longitudinal wavelengths.

FIG. 48 illustrates a schematic cross-sectional view of a portion of one example embodiment of an ultrasonic medical instrument 1524 comprising first and second waveguide portions 1530, 1532, where the first waveguide portion 1530 spans multiple ½ resonant longitudinal wavelengths. In the example embodiment show in FIG. 48, a medical ultrasonic waveguide 1526 includes at least two longitudinal vibration nodes 1528 located on the first waveguide portion 1530. In one variation, a sheath 1534 contacts (e.g., directly contacts or indirectly contacts through at least one intervening member 1536 such as a silicone intervening member) the first waveguide portion 1530 at the at-least-two longitudinal vibration nodes 1528. In some example embodiments, the sheath 1534 includes two rigid sheath portions 1538 and 1542 and one flexible sheath portion 1540, wherein the flexible sheath portion 1540 contacts the first waveguide portion 1530 at least one of the two longitudinal vibration nodes 1528, and wherein the flexible sheath portion 1540 is disposed between the two rigid sheath portions 1538 and 1542. In one example embodiment, the two rigid sheath portions 1538 and 1542 each contact the second waveguide portion 1532 at a corresponding one of the at-least-two longitudinal vibration nodes 1528.

Referring now to FIG. 47, the waveguide 1502 may comprise a blade portion 1544 adapted to contact and ultrasonically treat patient tissue. The blade portion 1544 may be disposed at a distal end of the waveguide 1502 (e.g., distal of the third blade portion 1508 of the blade 1502). In one example embodiment, the surgical instrument 1500 may also comprise a user-actuated clamp arm 1546 pivotally attached to the sheath 1514, 1534 proximate the blade portion 1544, wherein the clamp arm 1546 and the medical ultrasonic waveguide 1502 at least in part define an ultrasonic surgical shears 1548. The tissue pad and clamping arm control mechanism has been omitted from FIG. 47. Referring again to FIG. 48, the medical ultrasonic waveguide 1526 may also comprise a blade portion 1545, similar to the blade portion 1544, and disposed at a distal end of the first waveguide portion 1532. The blade portion 1545 may also be adapted to contact and ultrasonically treat patient tissue. The instrument 1524 of FIG. 48 may also comprise a clamp arm 1546, defining, with the blade portion 1545, an ultrasonic surgical shears 1548.

In various example embodiments, certain portions of the waveguides 1502, 1526 are substantially rigid. For example, first and third portions 1504 and 1508 of the waveguide 1502 may be substantially rigid. The first portion 1532 of the waveguide 1526 may be substantially rigid. Referring again to FIG. 47, the medical ultrasonic waveguide 1502 may include first and second neck portions 1550 and 1552 joining, respectively, the first and second waveguide portions 1504 and 1506 and the second and third waveguide portions 1506 and 1508. (A similar neck portion 1552 may join the first and second waveguide portions 1530, 1532 of the waveguide 1526.)

In one modification, the medical ultrasonic waveguide 1502 is substantially cylindrical from the first waveguide portion 1504 to the third waveguide portion 1508, wherein the first, second and third waveguide portions 1504, 1506 and 1508 each have a substantially constant diameter, and wherein the diameter of the second waveguide portion 1506 is smaller than the diameter of either of the first and third waveguide portions 1504 and 1508. In some example embodiments, the diameter of the second waveguide portion 1506 is between substantially one and two millimeters, and the diameter of the first and third waveguide portions is between substantially three and five millimeters. In one choice of materials, the medical ultrasonic waveguide 1502 consists essentially of a titanium alloy. In one modification, the medical ultrasonic waveguide 1502 includes first and second longitudinal vibration antinodes 1510 and 1512, and the first neck portion 1550 is disposed proximate the first longitudinal vibration antinode 1510 and the second neck portion 1552 is disposed proximate the second longitudinal vibration antinode 1512.

Figure 49:
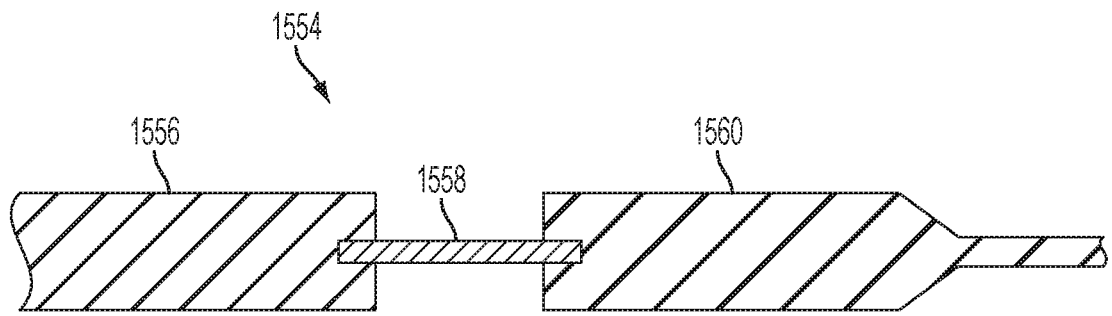
FIG. 49 illustrates a schematic cross-sectional view of one example embodiment of an ultrasonic waveguide for use with a medical instrument and comprising first and second waveguide portions, where a first waveguide portion is joined to a second waveguide portion by a dowel press fit.

FIG. 49 illustrates a schematic cross-sectional view of one example embodiment of an ultrasonic waveguide 1554 for use with a medical instrument and comprising first and second waveguide portions, where a first waveguide portion 1556 is joined to a second waveguide portion 1558 by a dowel press fit. In the example illustrated in FIG. 49, the second waveguide portion 1558 is also coupled to a third waveguide portion 1560 by a dowel press fit. In various example embodiments, the second waveguide portion 1558 consists essentially of titanium or nitinol. In the same or a different illustration, the length of the second waveguide portion 1558 is less than ½ wavelength (a wavelength being the length of a resonant-longitudinal-wavelength of the medical ultrasonic waveguide which depends essentially on the material of the waveguide and the frequency at which it is run) and in one example is less than ⅛ wave.

Figure 50:
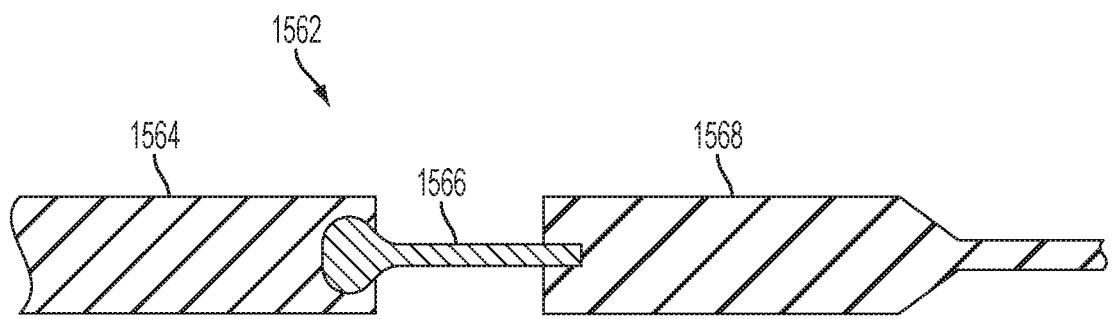
FIG. 50 illustrates a schematic cross-sectional view of one example embodiment of an ultrasonic waveguide for use with a medical instrument and comprising first and second waveguide portions, where the first waveguide portion is joined to the second waveguide portion by a ball-and-socket type attachment.

FIG. 50 illustrates a schematic cross-sectional view of one example embodiment of an ultrasonic waveguide 1564 for use with a medical instrument. Like the waveguide 1554, the waveguide 1564 is not a monolithic waveguide. The waveguide 1564 may comprise first and second waveguide portions 1564, 1566, where the first waveguide portion 1564 is joined to the second waveguide 1566 portion by a ball-and-socket type attachment. The second waveguide portion 1566 may also be joined to a third waveguide portion 1568 in any suitable manner. In the example of FIG. 50, the second waveguide portion 1566 is joined to the third waveguide portion 1568 via a dowel press fit. Other attachments between waveguide portions are left to those skilled in the art.

Figure 51:
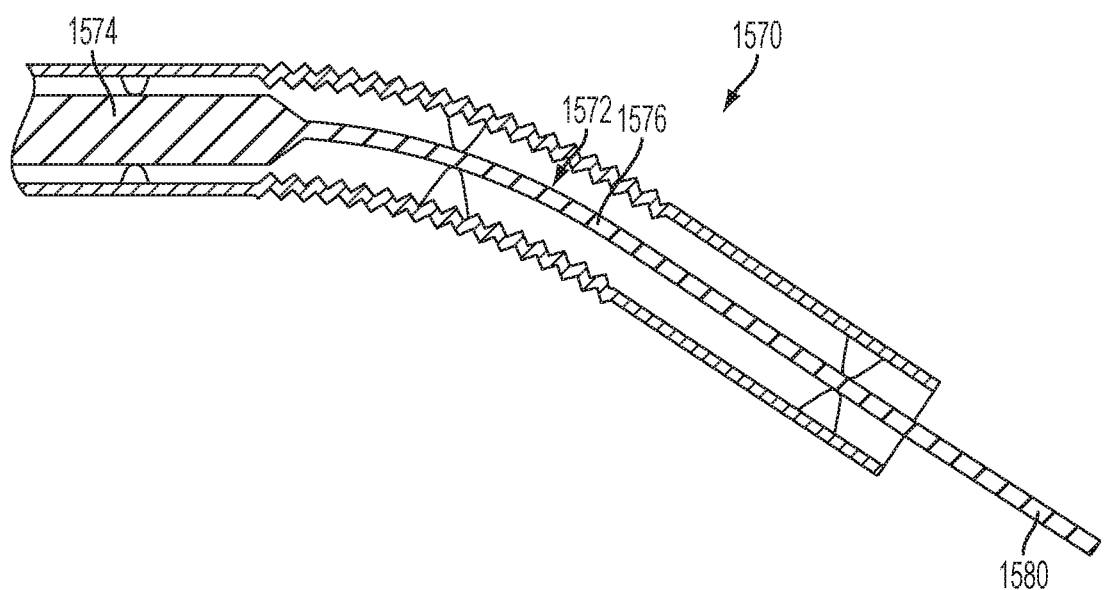
FIG. 51 illustrates a schematic cross-sectional view of a portion of another embodiment of an ultrasonic medical instrument comprising a medical ultrasonic waveguide having a length and including a proximal waveguide portion and a distal waveguide portion.

FIG. 51 illustrates a schematic cross-sectional view of a portion of another embodiment of an ultrasonic medical instrument 1570 comprising a medical ultrasonic waveguide 1572 having a length and including a proximal waveguide portion 1574 and a distal waveguide portion 1576. The proximal waveguide portion 1574 has a larger transverse area and the distal waveguide portion 1576 has a smaller transverse area. The distal waveguide portion 1576 bends more easily than does the proximal waveguide portion 1574. The distal waveguide portion 1576 includes a distal end portion 1580 adapted to contact and ultrasonically treat patient tissue. In various example embodiments, the additional ½ wave needed to neck up and create the larger diameter end effector of the embodiment of FIG. 47 is eliminated making it possible to place the articulation joint closer to the distal end of the ultrasonic medical instrument 1570. The embodiments, applications, etc. shown in FIGS. 47-50 are equally applicable (without the presence of the third waveguide portion) to the embodiment of FIG. 51.

Figure 52:
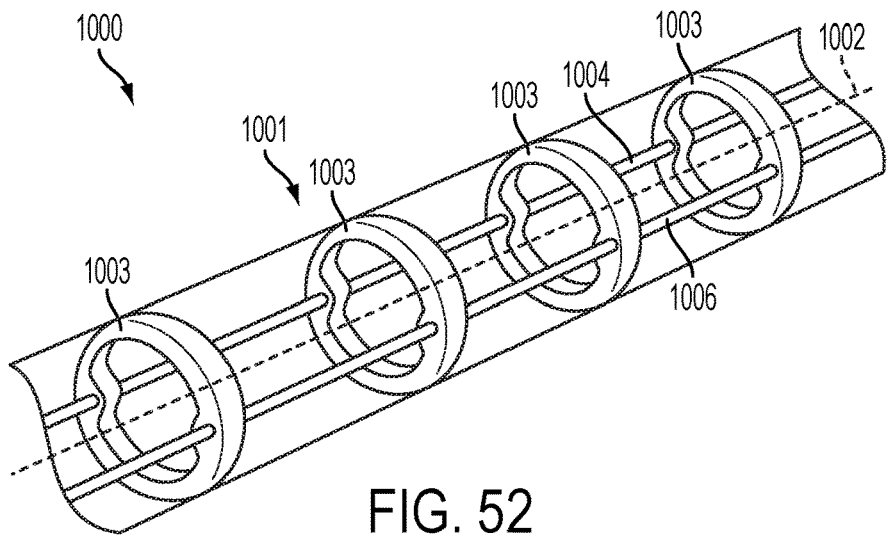
FIG. 52 illustrates a diagram showing a cut-away view of one example embodiment of a pivotable portion of a shaft of an example surgical instrument.

FIGS. 52-65 illustrate various embodiments of a surgical instrument having an articulating shaft comprising biased rotatable members. FIG. 52 illustrates a diagram showing a cut-away view of one example embodiment of a pivotable portion 1001 of a shaft 1000 of an example surgical instrument. The shaft portion 1001 may extend along a longitudinal axis 1002 and may be used by any type of surgical instrument including, for example, those described herein. The pivotable portion 1001 comprises a plurality of transverse spacer members 1003. First and second biased rotatable members 1004, 1006 may extend through the pivotable portion 1001 and through at least a portion of the respective spacer members 1003, as shown. For example, the transverse spacer members may be one or more disks centered on the longitudinal axis 1002. In various example embodiments, the spacer members 1003 define openings for receiving the rotatable members 1004, 1006 (or additional rotatable members, if utilized). Some or all of the spacer members 1003 may also define one or more additional openings for receiving a waveguide, wires, or other components passing from an end effector (not shown) through the shaft 1000.

Figure 53:
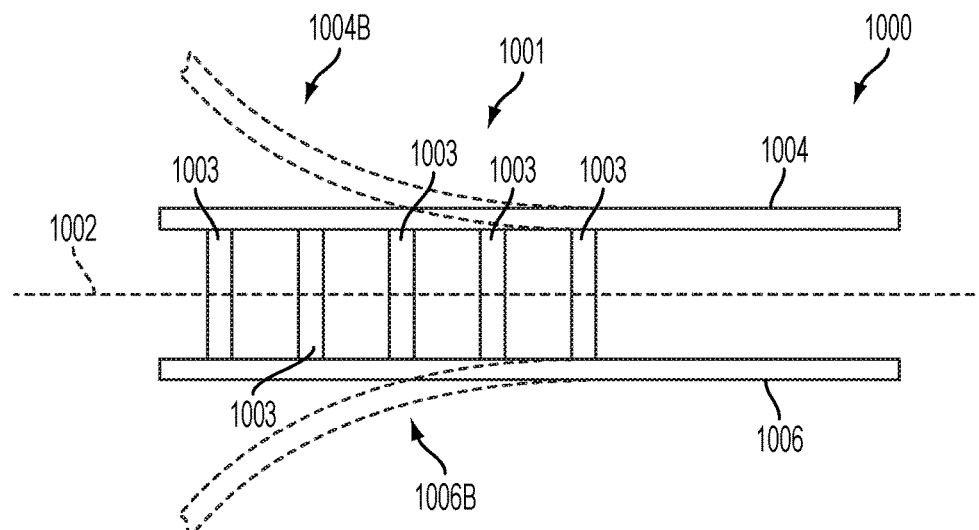
FIG. 53 illustrates a diagram showing a cut-away view of one example embodiment of the pivotable portion of the shaft including an indication of the bias of the rotatable members.

The rotatable members 1004, 1006 may each be biased away from the longitudinal axis 1002. For example, FIG. 53 illustrates a diagram showing a cut-away view of the pivotable portion 1001 of the shaft 1001 including an indication of the bias of the rotatable members 1004, 1006. Dotted portion 1004B illustrates the natural bias of the rotatable member 1004, while dotted portion 1006B illustrates the natural bias of the rotatable member 1006. In use, the rotatable members 1004, 1006 may be routed through at least a portion of the spacer members 1003 and, therefore, may not diverge from the longitudinal axis 1002 as shown by the dotted portions 1004B, 1006B. In some embodiments, the rotatable members 1004, 1006 are positioned so as to be centered in a common plane, as shown. The common plane may also include the longitudinal axis.

The biased rotatable members 1004, 1006 may be made from any suitable material and may be biased in any suitable manner. For example, in some embodiments, the rotatable members 1004, 1006 are made from a metal material such as surgical steel, etc. In some example embodiments, the members 1004, 1006 are biased by bending the metal or other material of the rods in the respective directions of bias. In other example embodiments, the members 1004, 1006 may be formed with a curvature in their respective directions of bias (e.g., as indicated by the dotted portions 1004B, 1006B of FIG. 53). Installing the members to the transverse spacer members 1003 may "bend" the respective members straight. In various example embodiments, the rotatable members 1004, 1006 may be constructed such that each member 1004, 1006 provides a substantially equal biasing force (e.g., a force tending to push the pivotable portion 1001 of the shaft 1000 away from the longitudinal axis 1002).

Figure 54:
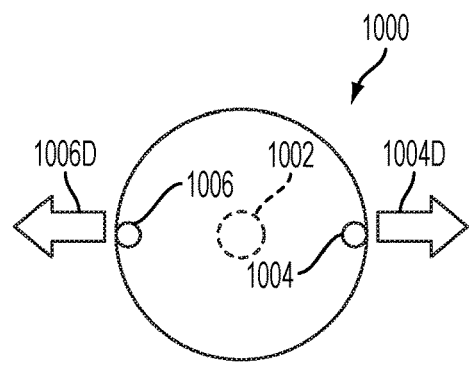
FIG. 54 illustrates a cross-sectional diagram of one example embodiment of the shaft of FIGS. 52 and 53 with the rotatable members 1004, 1006 rotated such that their directions of bias are opposed.

Rotating the members 1004, 1006 may change the direction of the members' respective biases, and bring about articulation of the shaft 1000. FIG. 54 illustrates a cross-sectional diagram of the shaft 1000 with the rotatable members 1004, 1006 rotated such that their directions of bias are opposed. With two rotatable members 1004, 1006, as illustrated in FIG. 54, the members 1004, 1006 may be opposed when they are directed in opposite directions. In example embodiments where the biasing forces provided by the members 1004, 1006 is substantially equal, then the respective biasing forces may be cancelled. Arrows 1004D and 1006D indicate the direction of bias of the rotatable members. As illustrated in FIG. 54, arrows 1004D and 1006D indicate that the directions of bias of the respective members 1004, 1006 is away from the longitudinal axis 1002. This may cause the shaft 1000 to assume a straight shape substantially parallel to the longitudinal axis, as illustrated in FIGS. 52 and 53.

Figure 55:
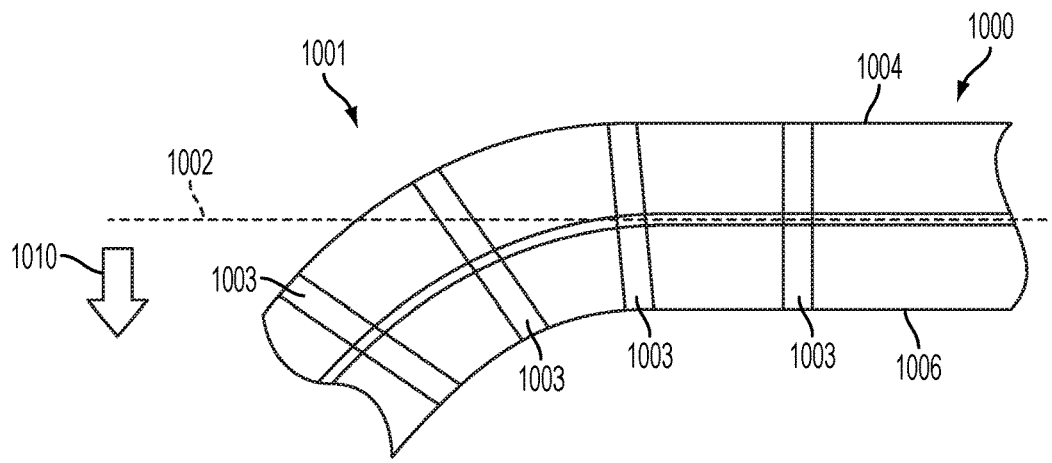
FIG. 55 illustrates a diagram showing a cut-away view of one example embodiment of the pivotable portion of the shaft with the rotatable members rotated such that their respective bias directions are aligned.
Figure 56:
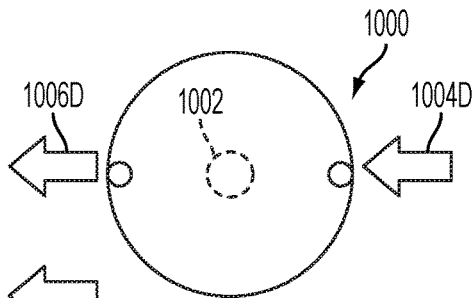
FIG. 56 illustrates a cross-sectional diagram of one example embodiment of the shaft of FIG. 52, configured as shown in FIG. 55.
Figure 58:
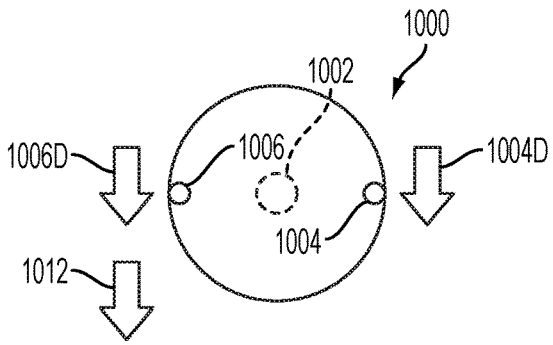
FIG. 58 illustrates a cross-section diagram of the example embodiment of the shaft of FIG. 52, configured as shown in FIG. 57.
Figure 57:
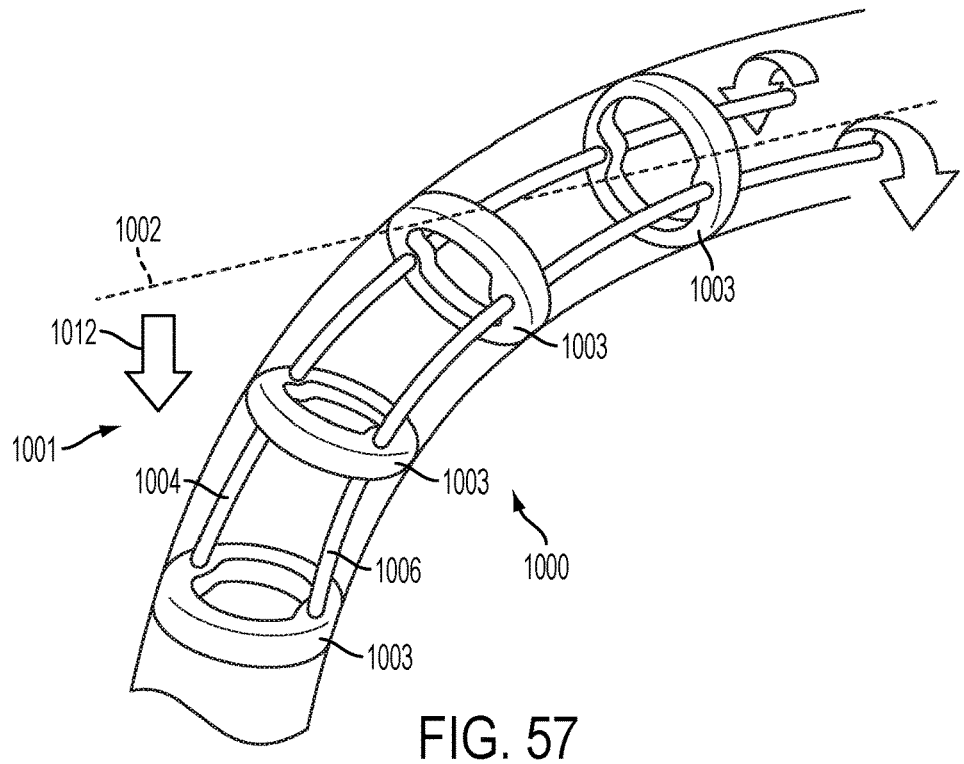
FIG. 57 illustrates a diagram showing a cut-away view of another example embodiment of the pivotable portion of the shaft with the rotatable members rotated such that their respective bias directions are aligned in another direction.

Rotating the members 1004, 1006 such that their respective bias directions align may cause the shaft 1000 to pivot at the pivotable portion 1001. For example, FIG. 55 illustrates a diagram showing a cut-away view of one example embodiment of the pivotable portion 1001 of the shaft 1000 with the rotatable members 1004, 1006 rotated such that their respective bias directions are aligned. FIG. 56 illustrates a cross-sectional diagram of one example embodiment of the shaft of FIG. 52, configured as shown in FIG. 55. In FIGS. 55-56, the bias directions 1006D, 1004D of the respective members 1004, 1006 are aligned in a common direction, indicated by arrow 1010. This may cause the pivotable portion 1001 of the shaft 1000 to pivot away from the longitudinal axis 1002 in the common direction 1010, as shown in FIG. 55. FIG. 57 illustrates a diagram showing a cut-away view of another example embodiment of the pivotable portion 1001 of the shaft 1000 with the rotatable members rotated such that their respective bias directions 1004D, 1006D are aligned in another direction. FIG. 58 illustrates a cross-section diagram of the example embodiment of the shaft of FIG. 52, configured as shown in FIG. 57. In FIGS. 57-58, the bias directions 1004D, 1006D of the respective rotatable members 1004, 1006 are aligned in a common direction indicated by arrow 1012. This may cause the pivotable portion 1001 of the shaft 1000 to pivot away from the longitudinal axis 1002 in the common direction 1012.

FIGS. 52-58 illustrate embodiments of the shaft 1000 comprising two biased rotatable members 1004, 1006. FIGS. 59-62 show another example embodiment comprising three biased rotatable members 1020, 1022, 1024. FIG. 59 illustrates a diagram showing a cut-away view of one example embodiment of a pivotable portion 1016 of a shaft 1018 comprising three biased rotatable members 1020, 1022, 1024. FIG. 60 illustrates a cross-sectional diagram of the example embodiment of FIG. 59. The natural bias directions of members 1022 and 1024 are indicated in FIG. 60 by dotted sections 1022B, 1024B. In various example embodiments, the biasing force provided by the respective members 1020, 1022, 1024 may be substantially equal.

In FIGS. 59-60, the bias directions 1020D, 1022D, 1024D of the respective members 1020, 1022, 1024 are opposed to one another, thereby canceling the respective biasing force that the members 1020, 1022, 1024 might tend to place on the pivotable portion 1016 of the shaft 1018. The may cause the pivotable portion 1016 of the shaft 1018 to remain roughly aligned with the longitudinal axis 1002. For example, the respective bias directions 1020D, 1022D, 1024D of the members 1020, 1022, 1024 may be arranged such that the vector sum of the biasing forces provided by the members 1020, 1022, 1024 is zero.

FIG. 61 illustrates a diagram showing a cut-away view of one example embodiment of a pivotable portion of the shaft of FIGS. 59-60 with the rotatable members rotated such that their respective bias directions are aligned. FIG. 62 illustrates a cross-sectional diagram of the shaft of FIG. 59 arranged as illustrated in FIG. 61. In FIGS. 61-62, the bias directions of the respective members 1020D, 1022D, 1024D are aligned in the direction of arrow 1030. This may cause the pivotable portion 1016 of the shaft 1018 to pivot away from the longitudinal axis 1002 in the direction 1030, as shown.

Figure 63:
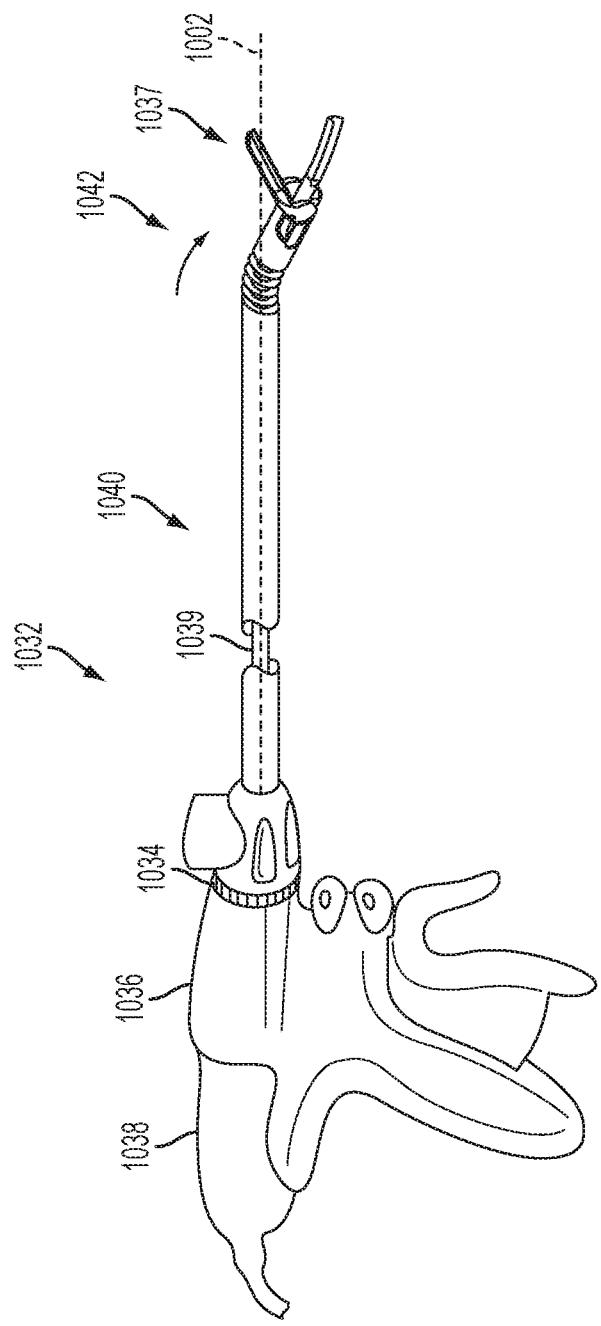
FIG. 63 illustrates a view of one example embodiment of a hand-held surgical instrument comprising a shaft similar to the shafts of FIG. 52-62.

As described herein, the bias directions of the respective members 1004, 1006, 1020, 1022, 1024 may be modified by rotating the respective members. Rotation of the members may be implemented in any suitable manner. For example, when the shafts such as 1000 and 1018 are utilized in a hand operating surgical instrument, the rotatable members may be rotated individually and/or collectively. For example, in some embodiments, the rotatable members may be geared together such that all of the members may be rotated in a single motion. FIG. 63 illustrates a view of example embodiment of a hand-held surgical instrument 1032 comprising a shaft 1040 having a pivotable portion 1042 similar to those of the shafts 1000 and 1018 described herein. The instrument 1032 comprises a handle 1036 and an end effector 1037. A rotation knob 1034 may be rotatable about the longitudinal axis 1002 to bring about pivoting of the pivotable portion 1042 away from the longitudinal axis 1002, as shown.

FIG. 64 illustrates a cross-sectional view of the shaft 1040 including a gear cluster 1045 for coupling rotating members 1042, 1044 to the knob 1034. The rotating members 1042, 1044 may operate to pivot the pivotable portion 1042 of the shaft 1040 in a manner similar to that described above with respect to rotating members 1004, 1006, 1020, 1022, 1024. The gear cluster 1045 is coupled to a shaft 1048 that may, in turn, be coupled to the knob 1034 such that rotation of the knob 1034 causes rotation of the shaft 1048. Rotation of the shaft 1048 may cause rotation of the gear cluster 1045 such that the rotating members 1042, 1044 are rotated in a coordinated manner (e.g., such that their respective bias directions are either opposed or aligned, as described herein). It will be appreciated that the shaft 1040 may be rotated in any suitable manner using any suitable mechanism. For example, in some embodiments, the shaft 1040 may be mechanically coupled to the knob 1034. In other embodiments, the shaft 1040 may be mechanically coupled to an instrument mounting portion 558 to receive rotational motion generated at the instrument mounting portion 558, as described herein.

Referring back to FIG. 63, the end effector 1037 comprises an ultrasonic blade that may be in communication with a transducer 1038. An ultrasonic waveguide 1039 may extend proximally from the end effector to the transducer 1038. In various embodiments, the ultrasonic waveguide 1039 may define a bendable portion, such as the bendable portions 1506, 1530, 1576, etc., described herein above. The bendable portion may be positioned along the longitudinal axis 1002 at about the location of the pivotable portion 1042 of the shaft 1040 such that pivoting of the pivotable portion 1042 causes bending of the bendable portion. It will be appreciated that the instrument 1032 may comprise electrosurgical components in addition to or instead of the ultrasonic components shown and described.

FIGS. 65A-65C illustrate cross-sectional views of the shaft 1040 showing different embodiments of the gear cluster 1045. In FIG. 65A, the rotating members 1042, 1044 and shaft 1048 are coupled to respective gears 1052, 1054, 1050. Rotation of the shaft 1048 may cause rotation of the gear 1050. The gear 1054 rotates with the gear 1050, and the gear 1052 rotates with the gear 1052. In this way, rotation of the shaft 1048 may bring about coordinated rotation of both of the rotatable members 1042, 1044. For example, the shafts may be rotatable from a first angular position where the bias directions of the respective shafts 1042, 1044 are opposed to a second angular position where the bias directions of the respective shafts 1042, 1044 are aligned. Interior portion 1056 represents an area that may be filled with various components extending from the end effector 1037 to the handle 1036 (or instrument mounting portion 558 in some robotic embodiments). For example, an ultrasonic waveguide may extend through interior portion 1056.

Referring now to FIG. 65B, the rotatable members 1042, 1044 and shaft 1048 may be coupled, respectively, to gears 1052', 1054', and 1063. Gear 1063 may be coupled directly to gear 1054' (and therefore to rotatable member 1044). Intermediate gears 1058, 1060 and 1062 may couple gear 1063 to gear 1052'. Accordingly, rotation of the shaft 1048 and gear 1063 may cause coordinated rotation of both rotatable members 1042, 1044. In FIG. 65C, the rotatable shafts 1042, 1044 may be individually rotatable. For example, shafts 1042, 1044 may be respectively coupled to gears 1052" and 1054". Shaft 1048 may be coupled to a gear 1066 that is, in turn, coupled to the gear 1052". Similarly, shaft 1048' may be coupled to a gear 1064 that is, in turn, coupled to the gear 1054". Accordingly, the rotatable members 1042, 1044 may be individually rotated by rotating respective shafts 1048, 1048'.

Figure 66B:
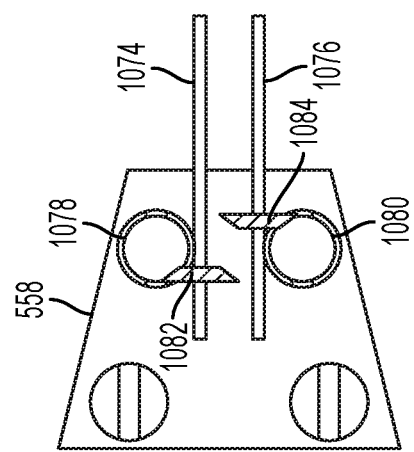
FIGS. 66A-66B illustrate embodiments of robotic instrument mounting portions that may be usable with the shaft and pivotable portion described herein above.
Figure 66A:
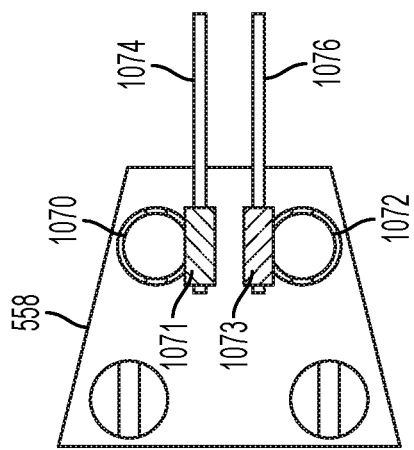

FIGS. 66A-66B illustrate embodiments of robotic instrument mounting portions 558 that may be usable with the shaft 1040 and pivotable portion 1042 described herein above. In FIG. 66A, two shafts 1074, 1076 extend proximally towards the instrument mounting portion 558 as shown. The shafts 1074, 1076 may be directly coupled to the rotating members 1044, 1042 and/or indirectly coupled to the rotating members 1044, 1042 (e.g., via shafts 1048, 1048'). The shafts 1074, 1076 may be coupled to respective worm gears 1071, 1073. The worm gears may be in mechanical communication with respective gears 1070, 1072. Gears 1070, 1072 may be rotated under control of a surgical robot, for example, as described herein above, such that individual rotation of the gears 1070, 1072 may cause individual rotation of the shafts 1074, 1076, respectively. In the example embodiment shown in FIG. 66B, the shafts 1074, 1076 are coupled to bevel gears 1080 and 1082 that are, in turn, mechanically coupled to gears 1078, 1080 that may be operated by a surgical robot to rotate the shafts 1074, 1076. Although the example embodiments illustrated in FIGS. 63-66 have only two rotatable members 1042, 1044, it will be appreciated that the control mechanisms described herein may be equally applicable to embodiments having additional rotatable members, such as those shown in FIGS. 59-62. For example, the gear cluster 1045 may be expanded to include additional gears for driving additional rotating members. Also, in some example robotic embodiments, additional gears may be driven by additional robot-controlled gears of the instrument mounting portion 558.

Figure 67:
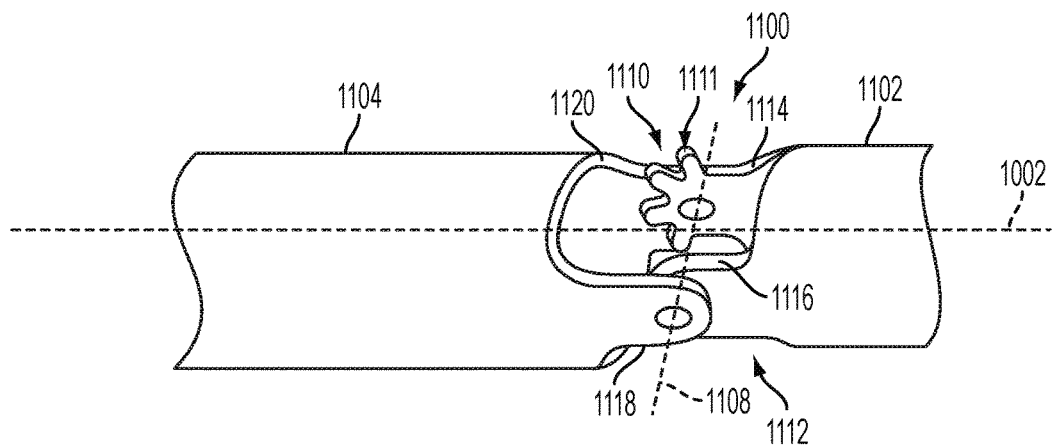
Figure 68:
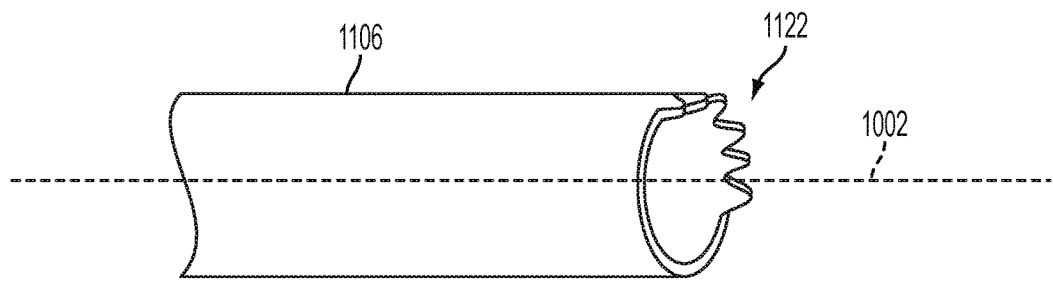
Figure 69:
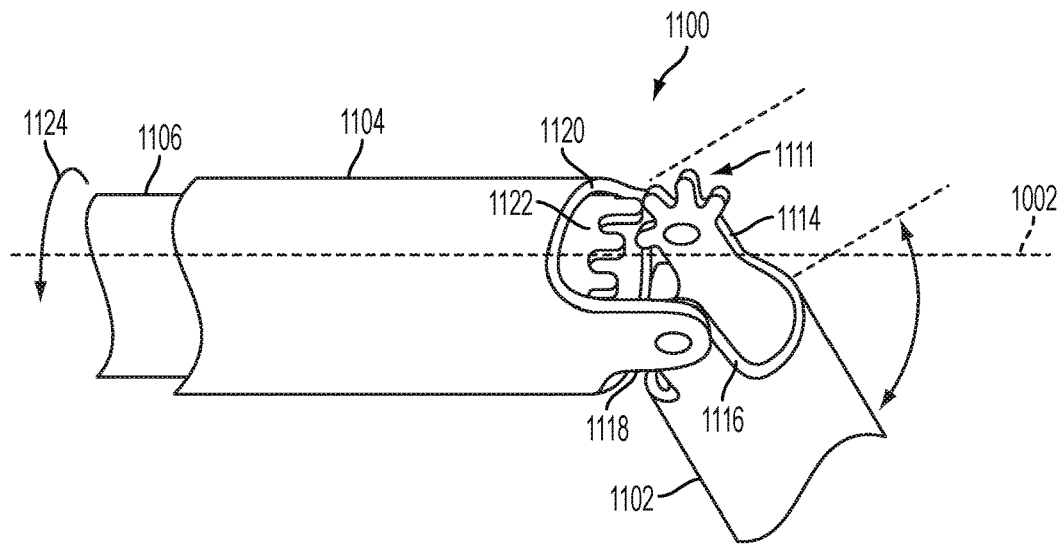

FIGS. 67-70 illustrate various example embodiments of a geared articulating shaft 1100 for use with a surgical instrument. FIG. 67 shows one example embodiment the shaft 1100 showing a proximal tube 1104 and a distal tube 1102. The proximal tube comprises a proximal clevis 1110 at a distal portion of the proximal tube 1104. The proximal clevis comprises clevis members 1118, 1120. The distal tube comprises a distal clevis 1112 at a proximal portion of the distal tube 1102, wherein the distal clevis 1112 comprises clevis members 1114, 1116. In the example embodiment shown, the respective devises 1110, 1112 are pivotably coupled to one another at an interface 1108 such that the distal tube 1102 is pivotable away from the longitudinal axis (FIG. 69). Clevis member 1114 of the distal clevis 1112 defines a geared portion 1111 comprising a plurality proximally directed of teeth, as shown. FIG. 68 shows one example embodiment of a rotatable inner tube 1106 that may be positioned within the proximal tube 1104. The tube 1106 may define a rack gear 1122 at a distal portion thereof. The rack gear 1122 may comprise a plurality of distally directed teeth positioned to interlock with the geared portion 1111 of the clevis member 114. In FIG. 69, the rotatable inner tube 1106 is illustrated positioned within the proximal tube 1104 such that the teeth of the geared portion 1111 and rack gear 1122 interlock. As the rotatable tube 1106 is rotated about the longitudinal axis, the rack gear 1122 may interact with the geared portion 1111 of the clevis member 1114 as shown so as to pivot the distal tube 1102 away from the longitudinal axis 1002, as shown in FIG. 69. Rotation of the tube 1106 in a first direction (indicated by arrow 1124) may pivot the distal tube 1102 in a first direction, while rotation of the tube 1106 in the opposite direction may pivot the distal tube 1102 in a second direction opposite the first direction.

FIG. 70 illustrates an additional embodiment of the shaft 1100 where the clevis 1112 of the distal tube 1102 is positioned outside the clevis 1110 of the proximal tube 1004. An additional gear 1126 may be coupled to clevis member 1116 via a pin 1128. The gear 1126 may comprise proximally directed teeth that interface with the proximally-facing teeth of the rack gear 1122. In the example embodiment shown in FIG. 70, rotation of the inner tube 1106 may cause pivoting of the distal tube 1102 in a manner similar to that shown in FIGS. 67-69. The rotatable inner tube 1106 may be rotated in any suitable manner. For example, when the shaft 1100 of FIGS. 67-70 is used in conjunction with a hand operated instrument, the tube 1106 may be rotated by a knob on a handle of the instrument in a manner similar to the way that the distal rotation assembly 13 causes rotation of the shaft assembly 14 of the instrument 10, as illustrated and described with respect to FIG. 1. Also, for example, when the shaft 1100 of FIGS. 67-70 is used in conjunction with a surgical robot, rotation of the inner tube 1106 may be actuated by the robot in a manner similar to the rotation of the shaft 638, as illustrated and described with respect to FIGS. 32-46C.

It will be appreciated that the shafts and articulation mechanisms illustrated and described with respect to FIGS. 67-70 may be used with any suitable type of surgical instrument, including various types of ultrasonic and electrosurgical instruments described herein. For example, when the example embodiments of FIGS. 67-70 are used in conjunction with an ultrasonic instrument, a waveguide may be positioned within the respective tubes 1102, 1104, 1106. The waveguide may have a bendable portion, such as bendable portions 1506, 1530, 1576, etc., described herein above. The bendable portion may be positioned along the longitudinal axis 1002 at about the location of the interface 1108 such that pivoting of the distal tube 1102 about the interface 1108 is facilitated by bending of the waveguide.

FIGS. 71-77 illustrate various embodiments of an articulating shaft 1130 that may be articulated by reciprocating motion along the longitudinal axis 1002 of a translating member. FIG. 71 illustrates one example embodiment of the articulating shaft 1130 where the translating member is a hollow inner tube 1136. The shaft 1130 may comprise a distal tube 1132, a proximal tube 1134 and the translating member 1136. An ultrasonic blade 1142 is shown in FIGS. 71-73, although it will be appreciated that the shaft 1130 may be used for any type of surgical instrument. The proximal tube 1134 may be coupled to the distal tube 1132 at a first hinge interface 1140. At the first hinge interface 1140, the distal tube 1132 may be free to pivot away from the longitudinal axis 1002. The first hinge interface 1140 may be offset from the longitudinal axis 1002, as shown.

The distal tube 1132 may additionally comprise an opening 1138 positioned opposite the longitudinal axis 1002 from the first hinge interface 1140 (e.g., when the distal tube 1132 is aligned with the proximal tube along the longitudinal axis 1002, as shown in FIG. 71). The translating member 1136 may comprise a pin 1141 that is received within the opening 1138 so as to form a second hinge interface between the translating member 1136 and the distal tube 1132. Alternately, the reciprocating member 1136 may define the opening 1138, with the pin 1141 coupled to the distal tube 1132.

FIG. 72 illustrates a cross section of one example embodiment of the shaft 1130 taking along the line AB illustrated in FIG. 71. FIG. 72 shows a pin 1143 that may form the first hinge interface 1140 and also illustrates that pin 1141 may have an analog 1141' opposite the longitudinal axis 1002.

FIG. 73 illustrates one example embodiment of the shaft 1130 as articulated by the translating member 1136. As illustrated, the translating member 1136 is translated distally. The pin 1114 contacts the opening 1138, pushing the distal tube 1132 away from the proximal tube 1134 and causing the distal tube 1132 to pivot away from the longitudinal axis 1002 as shown. The translating member 1036 may be translated distally along the longitudinal axis 1002 to pull the distal tube 1132 back towards the proximal tube 1134 and into the position shown in FIG. 71.

Figure 75:
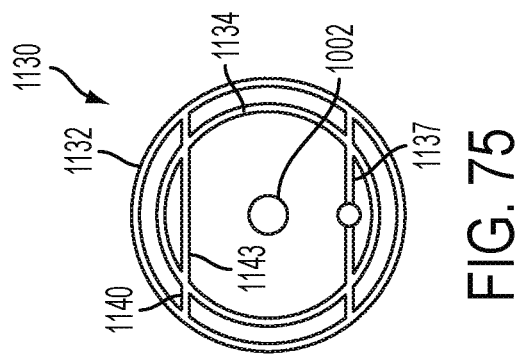
FIGS. 74-76 illustrate another example embodiment of the shaft of FIGS. 71-73 for use with an alternative translating member.
Figure 74:
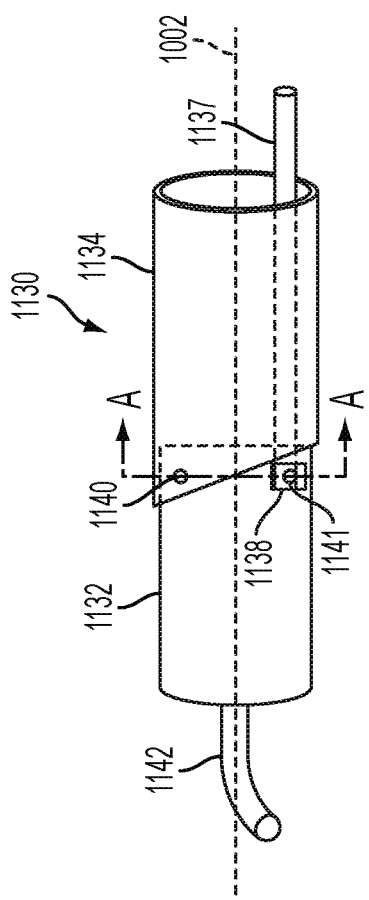
Figure 76:
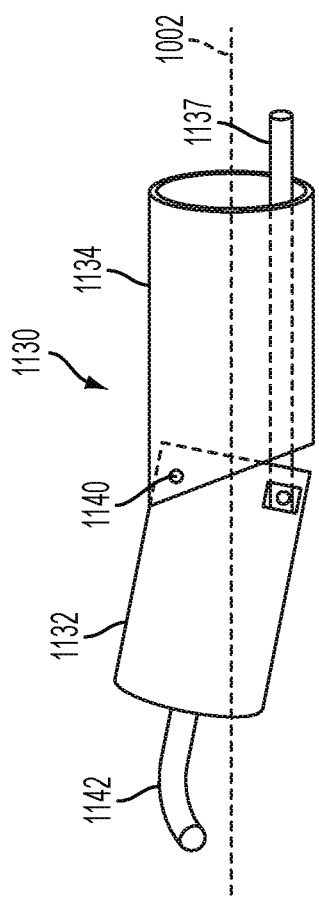

FIGS. 74-76 illustrate another example embodiment of the shaft 1130 for use with an alternative translating member 1137. Instead of forming a hollow tube, like the translating member 1136, the translating member 1137 comprises a rod, with the pin 1141 positioned transverse to the rod 1137 and coupled thereto. Distally directed translation of the rod 1137 may push the distal tube 1132 away from the proximal tube 1134 and away from the longitudinal axis 1002, as shown in FIG. 76. Similarly, proximal translation of the rod 1137 may pull the distal tube 1132 back towards the proximal tube 1134 and the longitudinal axis 1002 to the position illustrated in FIG. 74.

It will be appreciated that the translating members 1136, 1137 described above may be translated distally and proximally according to any suitable method. For example, when the shaft 1130 is used in conjunction with a manual or hand held surgical instrument, the translating members 1136, 1137 may be translated distally and proximally in a manner similar to that described herein above with respect to the reciprocating tubular actuating member 58 of the instrument 10 and/or the axially moving member 378 of the instrument 300. Also, for example, when the shaft 1130 is used in conjunction with a surgical robot, the translating members 1136, 1137 may be translated distally and proximally in a manner similar to that described above with respect to the tissue cutting element 555 of the instrument 310.

FIG. 77 illustrates another embodiment of a mechanism for translating the translating member 1136 distally and proximally, for example, in the context of a surgical robot. The translating member 1136 is illustrated with a rack gear 1144. A rotating gear 1142 interfaces with the rack gear such that rotation of the gear 1142 in a first direction causes the member 1136 to translate distally and rotation of the gear 1142 in a second direction causes the member 1136 to translate proximally. The gear 1142, for example, may be coupled to one of the rotatable bodies 612 of the robotic instrument mounting portion 558, described herein above. FIG. 78 illustrates an alternate embodiment of the mechanism shown in FIG. 77, wherein the gear 1142 interfaces with a rack gear 1146 of the rod 1137. The gear 1142 and rack gear 1146 may operate to translate the rod 1137 distally and proximally in a manner similar to that described with respect to FIG. 77.

FIG. 79 illustrates yet another embodiment of a mechanism for translating the translating member 1136. As shown in FIG. 79, a first spool 1150 comprises a first cable 1164 wound around the spool 1150. One end of the cable 1164 is coupled to the translating member 1136 at connection point 1160. Rotation of the spool 1150 in the direction indicated by arrow 1154 may cause the spool to wind the cable 1164, placing a proximally-directed force on the translating member 1136 at connection point 1160 and causing the translating member 1136 to move proximally. A second spool 1148 is coupled to and winds a second cable 1156 coupled to the translating member 1136 at a connection point 1158. Rotation of the spool 1148 in the direction of arrow 1152 may cause the spool 1148 to wind the cable 1156, placing a distally-directed force on the translating member 1136 at connection point 1160 and causing the translating member 1136 to move distally. The spools 1148 may, in some embodiments, be coupled to rotatable bodies 612 of the robotic instrument mounting portion 558, described herein above.

It will be appreciated that the shafts and articulation mechanisms illustrated and described with respect to FIGS. 71-78 may be used with any suitable type of surgical instrument, including various types of ultrasonic and electrosurgical instruments described herein. For example, when the example embodiments of FIGS. 71-78 are used in conjunction with an ultrasonic instrument, a waveguide may be positioned within the respective tubes 1134, 1132, 1136. The waveguide may have a bendable portion, such as bendable portions 1506, 1530, 1576, etc., described herein above. The bendable portion may be positioned along the longitudinal axis 1002 at about the location of the first hinge interface 1140 such that pivoting of the distal tube 1132 about the interface 1140 is facilitated by bending of the waveguide.

FIG. 80 illustrates one embodiment of an articulating shaft 1152 that may be used in conjunction with an end effector 1157 comprising an ultrasonic blade 1158. The shaft 1152 comprises a proximal tube 1154 and a distal tube 1156. The proximal tube may define a clevis 1166. The proximal and distal tubes 1154, 1156 may be pivotably joined at the clevis 1166, for example, by a rivet or pin 1165. Accordingly, the distal tube 1156 may pivot about a hinge interface 1168 away from the longitudinal axis 1002, as shown. In the example embodiment of FIG. 80, the end effector 1157 comprises an ultrasonic blade 1158. Extending proximally from the ultrasonic blade 1158 is a waveguide 1160. The waveguide 1160 may have a bendable or flexible portion 1162 positioned along the longitudinal axis at about the hinge interface 1168.

Articulation of the distal tube 1156 and end effector 1157 may be brought about by a pair of differential translating members 1170, 1172. The translating members may be coupled to the distal tube 1156 and may extend proximally through the proximal tube 1154 as shown. Proximal translation of the translating member 1170 may pull the distal tube 1156 and end effector 1157 towards the translating member 1170, as shown in FIG. 80. Similarly, proximal translation of the translating member 1172 may pull the distal tube 1156 and end effector 1157 in the opposite direction (e.g., towards the translating member 1172). In various embodiments, when one translating member 1172 is pulled proximally, the other may be pulled distally by the distal tube 1156. This may require the provision of slack in the opposite translating member 1170, 1172.

Figure 81:
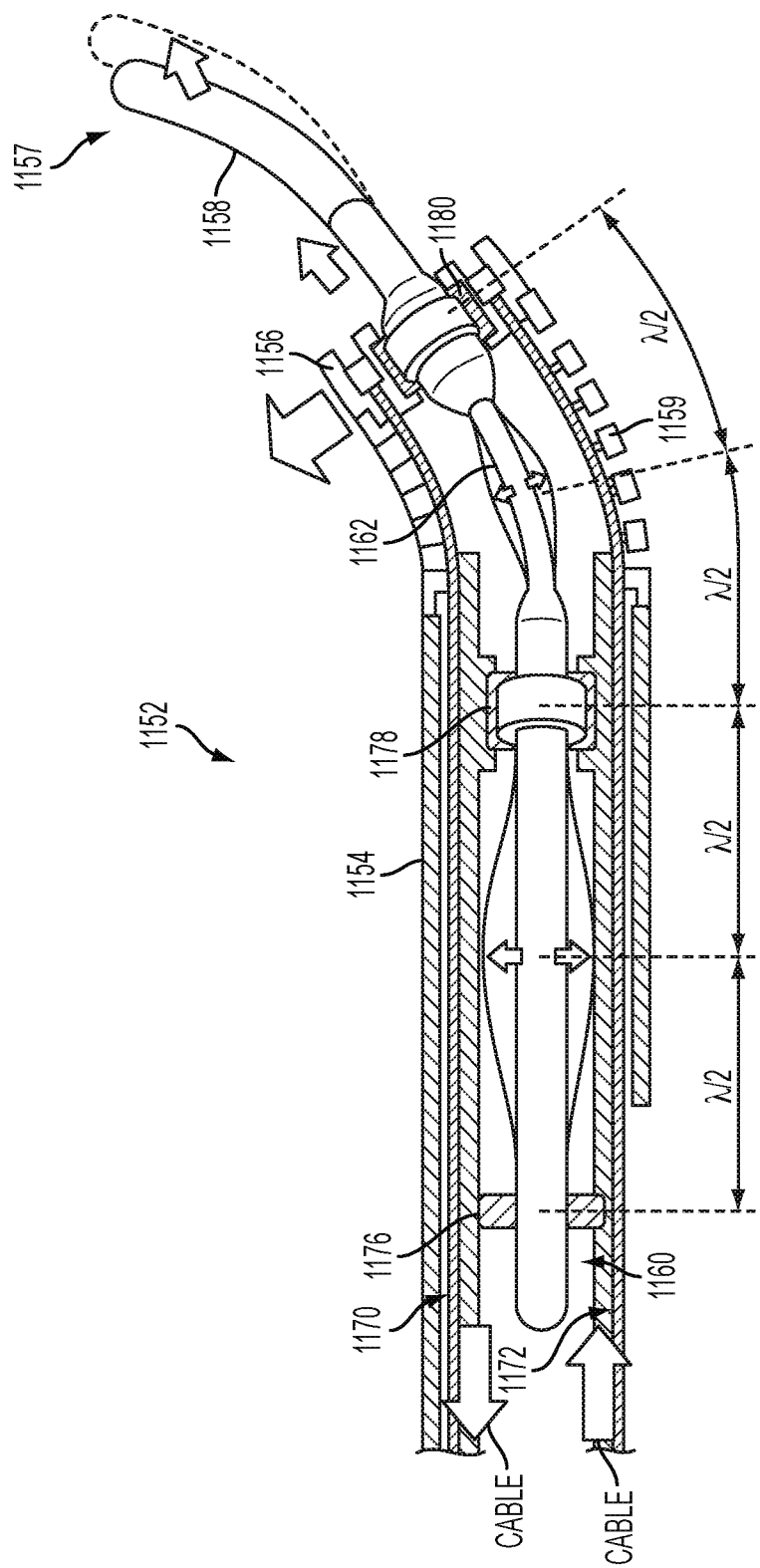
FIG. 81 illustrates an alternate embodiment of the articulating shaft of FIG. 80.

FIG. 81 illustrates an alternate embodiment of the articulating shaft 1152. In FIG. 81, the clevis 1166 and hinge interface 1168 of the example embodiment of FIG. 80 is replaced with a flexible neck portion 1159. The waveguide 1160 is coupled to interior portions of the proximal tube 1154 at mounting points 1176 and 1178. Distal of the bendable or flexible portion 1162 of the waveguide 1160, the waveguide 1160 is shown coupled to the distal tube 1156 at a connection point 1180. The various connection points 1176, 1178, 1180 may be positioned along the waveguide 1160 at nodes of the waveguide 1160 (positions where there is no longitudinal and/or transverse vibration of the waveguide 1160). In various embodiments, as described herein, the nodes may be separated by integer multiples of one wavelength at a resonant frequency of the system including the waveguide 1160, blade 1158. The example embodiment of the shaft 1152 illustrated in FIG. 81 may be articulated in a manner similar to that of the example embodiment of the shaft 1152 illustrated in FIG. 80. For example, translating member 1170 may be pulled proximally to pull the distal tube 1156 toward the cable 1170 into the position shown in FIG. 81. Translating member 1172 may be pulled proximally to pull the distal tube 1156 toward the cable 1172.

Differential translation of the translating members 1170, 1172 may be accomplished in any suitable manner. For example, when the shaft 1152 is utilized in the context of a surgical robot, the members 1170, 1172 may be differentially translated utilizing any of the methods and/or mechanisms described herein above with respect to FIGS. 32-46C. FIG. 82 illustrates a diagram of one embodiment of the shaft 1152 utilized in conjunction with a manual device for actuating articulation. Translating members 1170, 1172, at their proximal portions, may be coupled to respective rack gears 1182, 1184. A spindle gear 1188 may be positioned between the rack gears 1182, 1184 so as to engage both of the rack gears 1182, 1184. A lever 1186 maybe coupled to the spindle gear 1188 and handled by the clinician. The clinician may pivot the distal tube 1156 and end effector 1157 towards the translating member 1170 by turning the lever 1186 and spindle gear 1188 counter clockwise, as shown by arrows 1190. This causes the spindle gear 1188 to pull rack gear 1182 and translating member 1170 proximally while pushing rack gear 1184 and translating member 1172 distally. The distal movement of the translating member 1172 may create slack in the member 1172 allowing the distal tube 1156 and end effector 1157 to pivot as shown. Similarly, clockwise rotation of the lever 1186 and spindle gear 1188 may pull the rack gear 1184 and member 1172 proximally while pushing the rack gear 1182 and member 1170 distally. As described above, this may bring about articulation of the distal tube 1156 and end effector 1157 towards the member 1172. Although FIG. 82 shows proximal and distal tubes 1154, 1156 pivotally joined at a hinge interface 1168, it will be appreciated that the mechanisms shown in FIG. 82 may be similarly utilized in embodiments comprising a flexible neck portion 1159.

Figure 83:
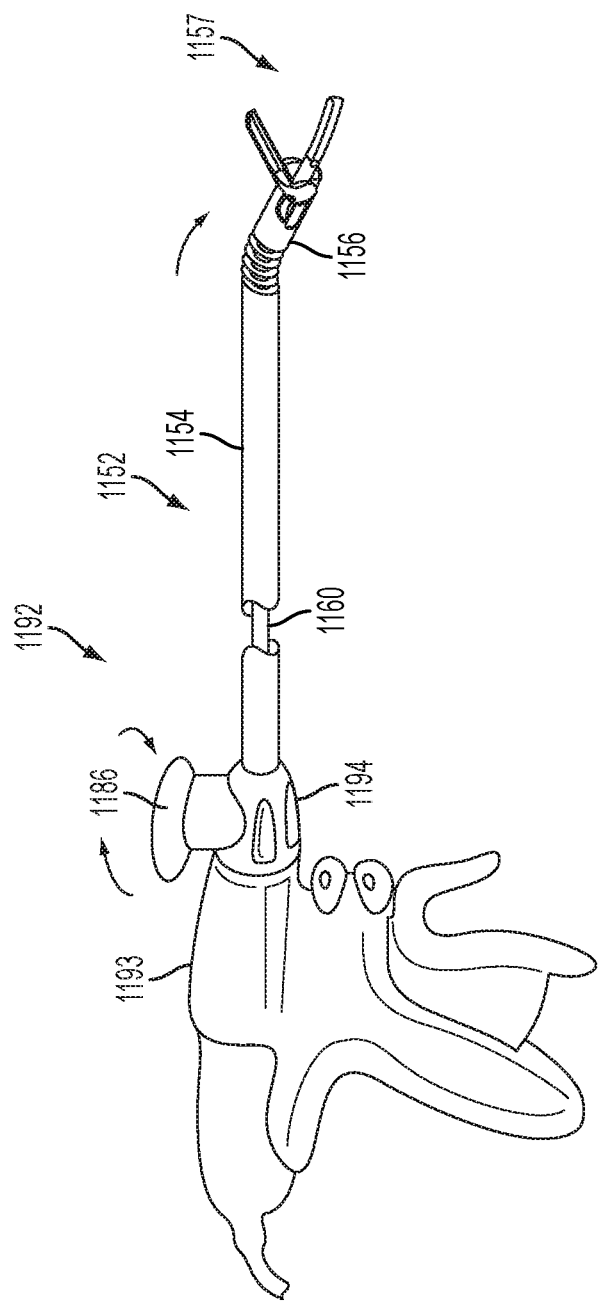
FIG. 83 illustrates one example embodiment of a surgical instrument for use with the manual articulation device illustrated in FIG. 82.

FIG. 83 illustrates one example embodiment of a surgical instrument 1192 for use with the manual articulation device illustrated in FIG. 82. The instrument 1192 comprises a handle 1193. An articulation housing 1194 is positioned between the handle 1193 and the shaft 1152. The lever 1186 is illustrated as rotatably coupled to the articulation housing 1194. The spindle gear 1188 and rack gears 1182, 1184 are not shown in FIG. 83, but may be positioned within the articulation housing 1194.

Figure 84:
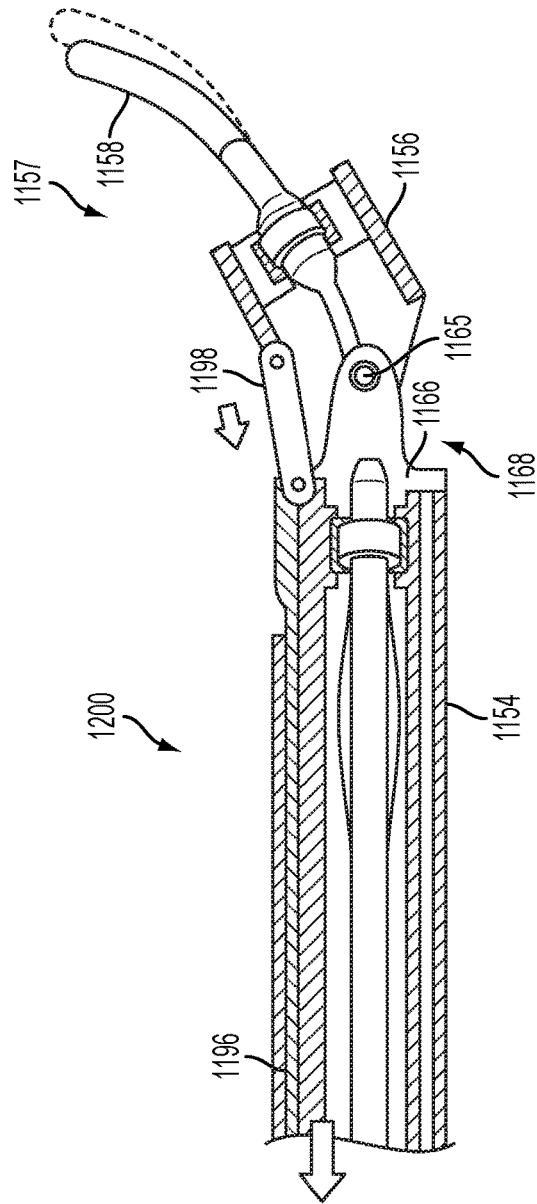
FIG. 84 illustrates one embodiment of an articulating shaft comprising a rigid translating member and linkage member.

FIG. 84 illustrates one embodiment of an articulating shaft 1200 comprising a rigid translating member 1196 and linkage member 1198. The shaft 1200 may be similar to the shaft 1152 in that it may comprise a proximal tube 1154 and a distal tube 1156 pivotably coupled to the proximal tube 1154. The proximal and distal tubes 1154, 1156 may be coupled at a hinge interface 1168, as shown in FIG. 84 or by a flexible neck portion 1159 as shown in FIG. 81. The distal tube 1156 may be coupled to an end effector 1157 comprising an ultrasonic blade 1158, as described above. To bring about translation of the distal tube 1156 and end effector 1157, the shaft 1200 may comprise a rigid translating member 1196 and linkage member 1198. The rigid translating member 1196 may translate distally and proximally. Proximal translation of the translating member 1196 may pull the linkage member 1198, distal tube 1156 and end effector 1157 towards the translating member 1196, causing the distal tube 1156 and end effector 1157 to pivot about the hinge interface 1168 towards the translating member 1196 as shown in FIG. 84. Distal translation of the translating member 1196 may push the linkage member 1198, distal tube 1156 and end effector 1157 away from the translating member 1196, causing the distal tube 1156 and end effector 1157 to articulate in a direction opposite that shown in FIG. 84.

Figure 85:
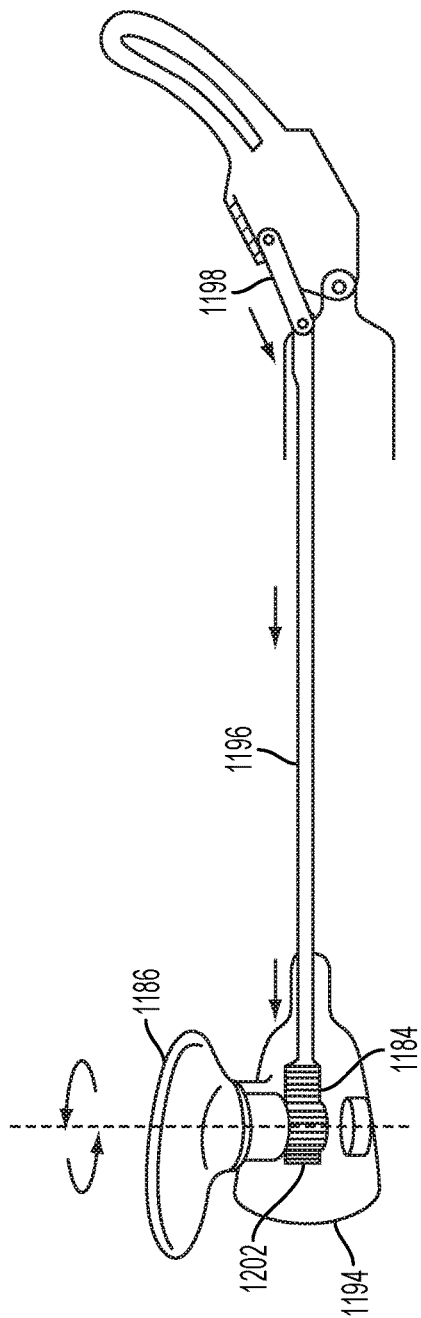
FIG. 85 illustrates one embodiment of the shaft of FIG. 84 in conjunction with the lever and spindle gear of FIG. 82.

Distal and proximate translation of the translating member 1196 may be accomplished in any suitable manner. For example, when the shaft 1200 is used in conjunction with a manual or hand held surgical instrument, the translating member 1196 may be translated distally and proximally in a manner similar to that described herein above with respect to the reciprocating tubular actuating member 58 of the instrument 10 and/or the axially moving member 378 of the instrument 300. Also, for example, when the shaft 1200 is used in conjunction with a surgical robot, the translating member 1196 may be translated distally and proximally in a manner similar to that described above with respect to the tissue cutting element 555 of the instrument 310. Additionally, FIG. 85 illustrates one embodiment of the shaft 1200 in conjunction with the lever 1186 and spindle gear 1184 described above. The rigid translating member 1196 may be coupled, at a proximal portion, to a rack gear 1202, similar to the rack gears 1182, 1184 described above. Clockwise and counter clockwise rotation of the lever 1186 and spindle gear 1184 may cause distal and proximal translation of the rack gear 1202 and translating member 1196.

Figure 86:
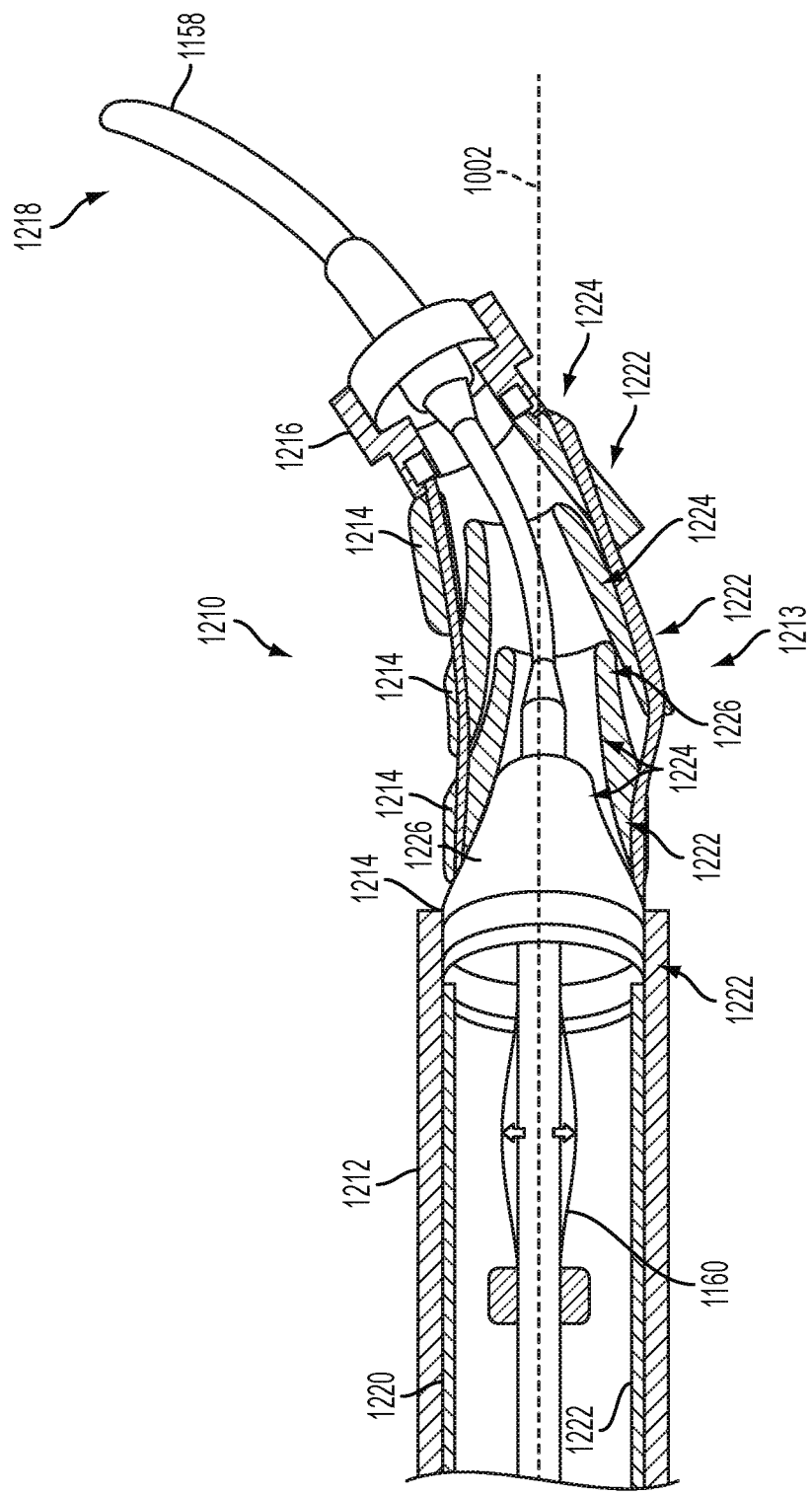
FIG. 86 illustrates one example embodiment of an articulating shaft that may be used in conjunction with an end effector comprising an ultrasonic blade.

FIG. 86 illustrates one example embodiment of an articulating shaft 1210 that may be used in conjunction with an end effector 1218 comprising an ultrasonic blade 1158. The shaft 1210 may comprise a proximal tube 1212 and a distal tube 1216 joined by a flexible articulation neck 1213. A waveguide 1160 may extend proximally from the ultrasonic blade 1158 through the articulation neck 1213 and proximal tube 1212 to an ultrasonic transducer (not shown). The articulation neck 1213 comprises a plurality of hollow neck members 1214. Each of the hollow neck members 1214 may comprise a proximal end 1222 and a distal end 1224. The distal end of each hollow neck member 1214 may fit within the proximal end of the next distal-most member 1214. In various example embodiments, each hollow neck member 1214 may comprise a coupling member 1226 around an exterior portion of its distal end 1224. The coupling member 1226 may be configured to contact an interior portion of the next distal-most hollow neck member 1214, as shown. In various embodiments, the coupling member 1226 may be made of surgical rubber or another resilient material so as to create a partial or complete seal between adjacent hollow neck members. In other embodiments, the coupling member 1226 may be made from a metal or other material to promote movement of the hollow neck members 1214 relative to one another so as to pivot the articulation neck 1213.

The shaft 1210 may be used with any type of surgical instrument, including an ultrasonic and/or electrosurgical instrument. In the example embodiment shown in FIG. 86, the shaft 1210 is utilized with the ultrasonic blade 1158. The blade 1158 is acoustically coupled to a waveguide 1160 extending proximally through the distal tube 1216, articulation neck 1213 and proximal tube 1212. The waveguide 1160 may define a bendable portion 1228, such as the bendable portions 1506, 1530, 1576, etc., described herein above. In various embodiments, the bendable portion 1228 may be positioned at about the articulation neck 1213, as shown. A pair of translating members 1220, 1222 may be coupled to the distal tube 1216 and may extend proximally through at least a portion of the hollow neck members 1214. In the example embodiment illustrated in FIG. 86, the translating members 1220, 1222 extend through openings in each of the hollow neck members 1214. The translating members 1220, 1222 may be slidably and/or fixedly coupled to the respective hollow neck members 1214. Beyond the articulation neck 1213, the translating members 1220, 1222 may extend proximally through the proximal tube 1212.

The translating members 1220, 1222 may be used in various different ways to control articulation of the distal tube 1216 and the end effector 1218. In some example embodiments, articulation of the distal tube 1216 and end effector 1218 may be passive. For example, the translating members 1220, 1222 may both be translated distally, so as to allow slack between the distal end of the proximal tube 1212 and the distal tube 1216. When such slack is present, the respective hollow neck members 1214 may slide over one another, allowing the distal tube 1216 and end effector 1218 to pivot away from the longitudinal axis 1002. To lock the end effector 1218 and articulation neck 1213 in place, the translating members 1220, 1222 may be retracted proximally, thus removing the slack and pulling the hollow neck members 1214 into a tight fit with one another. For example, the coupling members 1216 of the respective hollow neck members 1213 may grip adjacent hollow neck members 1213 tending to prevent movement. Distal and proximate translation of the translating members 1220, 1222 may be accomplished in any suitable manner. For example, when the shaft 1210 is used in conjunction with a manual or hand held surgical instrument, the translating members 1220, 1222 may be translated distally and proximally in a manner similar to that described herein above with respect to the reciprocating tubular actuating member 58 of the instrument 10 and/or the axially moving member 378 of the instrument 300. Also, for example, when the shaft 1210 is used in conjunction with a surgical robot, the translating members 1220, 1222 may be translated distally and proximally in a manner similar to that described above with respect to the tissue cutting element 555 of the instrument 310. The translating members 1220, 1222 may be translated distally and proximally in a manual embodiment similar to that shown in FIG. 85. For example, both translating members 1220, 1222 may be coupled to the rack gear 1202.

In other example embodiments, the translating members 1220, 1222 may be utilized to implement controlled articulation. For example, proximal translation of the translating member 1220 may pull the end effector 1218 and distal tube 1216 toward the translating member 1220, as shown. Proximal translation of the translating member 1222 may pull the end effector 1218 and distal tube back towards the longitudinal axis 1002 from the position shown in FIG. 86 and away from the longitudinal axis 1002 (e.g., in the opposite direction). Differential translation of the translating members 1220, 1222 may be accomplished in any suitable manner. For example, when the shaft 1152 is utilized in the context of a surgical robot, the members 1220, 1222 may be differentially translated utilizing any of the methods and/or mechanisms described herein above with respect to FIGS. 32-46C. The translating members 1220, 1222 may be differentially translated in a manual embodiment similar to that shown in FIG. 82. For example, the translating members 1220, 1222 may be coupled to respective rack gears similar to 1182, 1184.

Non-Limiting Examples

Various example embodiments described herein are directed to articulating surgical instruments for treating tissue comprising an end effector and a shaft extending proximally from the end effector along a longitudinal axis. In certain embodiments, the shaft comprises a plurality of transverse spacer members as well as first and second rotatable members extending through at least a portion of the plurality of transverse spacer members. The first and second rotatable members may both be biased away from the longitudinal axis such that their respective directions of bias vary with rotation of the first rotatable member. When the respective directions of bias of the first and second rotatable members oppose one another, the shaft may be substantially straight. When the respective directions of bias of the first and second rotatable members are aligned with one another, the shaft may articulate away from the longitudinal axis in the direction of the alignment.

In certain embodiments, the shaft may comprise a proximal tube, a distal tube and a rotatable inner tube. The proximal tube may define a proximal clevis comprising first and second clevis members while the distal tube may define a distal clevis comprising first and second clevis members. The distal clevis may be coupled to the proximal clevis such that the distal tube is pivotable relative to the proximal tube about an interface between the distal tube and the proximal tube. The first clevis member of the distal clevis may comprise a first plurality of teeth. The rotatable inner tube may be positioned within the proximal tube and may be rotatable about the longitudinal axis. A distal end of the inner tube may define a second plurality of teeth positioned to interlock with the first plurality of teeth such that rotation of the inner tube about the longitudinal axis causes the distal tube to pivot about the interface between the distal tube and the proximal tube.

In certain embodiments, the shaft comprises a proximal tube, a distal tube and a translating member. The proximal tube and the distal tube may be pivotably coupled at a first hinge interface. The translating member may extend through the proximal tube and may be coupled to the distal tube at a second hinge interface such that translation of the translating member along the longitudinal axes causes the proximal tube to pivot relative to the distal tube.

In certain embodiments, the end effector comprises an ultrasonic blade while the shaft comprises proximal and distal tubes coupled at a first hinge interface. A waveguide may be acoustically coupled to the ultrasonic blade and may extend proximally through the shaft. The waveguide may define a flexible portion positioned at about the first hinge interface. In some embodiments, first and second translating members may be coupled to the distal tube and extend proximally through the proximal tube. Proximal translation of the first translating member may cause the distal tube to pivot about the first hinge interface in a direction of the first translating member. Proximal translation of the second translating member may cause the distal tube to pivot about the first hinge interface in a direction of the second translating member. In additional embodiments, a rigid translating member may extend through at least a portion of the proximal tube. A linkage member may define a proximal end pivotably coupled to the proximal tube and a distal end pivotably coupled to the distal tube such that distal translation of the translating member causes the distal tube to pivot about the first hinge interface away from the translating member.

In certain embodiments, an articulation neck is positioned between the shaft and the end effector. The articulation neck may define a proximal end coupled to the shaft and a distal end coupled to the end effector. The articulation neck may comprise a plurality of hollow neck members including a first hollow neck member and a second hollow neck member. The first hollow neck member may defines a proximal end configured to receive a distal end of the second hollow neck member such that the first and second hollow neck members are pivotably coupled to each other.

It will be appreciated that any of the shafts and articulation mechanisms illustrated and described herein may be used with any suitable type of surgical instrument, including various types of ultrasonic and electrosurgical instruments described herein.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, each of the disclosed embodiments may be employed in endoscopic procedures, laparoscopic procedures, as well as open procedures, without limitations to its intended use.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An articulatable surgical instrument comprising:
an end effector comprising an ultrasonic blade;
a shaft extending proximally from the end effector along a longitudinal axis, wherein the shaft comprises:
  a pivotable portion at a first position on the longitudinal axis proximal to the end effector, wherein the pivotable portion comprises a plurality of transverse spacer members;
  a first rotatable member extending through the plurality of transverse spacer members parallel to the longitudinal axis, wherein the first rotatable member comprises a first natural bias extending in a first natural bias direction away from the longitudinal axis, and wherein the first natural bias direction of the first rotatable member varies with rotation of the first rotatable member;
  a second rotatable member extending through the plurality of transverse spacer members parallel to the longitudinal axis and offset from the first rotatable member along a direction perpendicular to the longitudinal axis, wherein the second rotatable member comprises a second natural bias extending in a second natural bias direction away from the longitudinal axis, wherein the second natural bias direction of the second rotatable member varies with rotation of the second rotatable member, wherein the pivotable portion of the shaft is substantially straight when the first and second rotatable members are rotated such that the first natural bias direction and the second natural bias direction oppose one another and both the first rotatable member and the second rotatable member exert bias forces oriented radially outward from the longitudinal axis, and wherein the pivotable portion of the shaft articulates in a first direction away from the longitudinal axis when the first and second rotatable members are rotated such that the first natural bias direction and the second natural bias direction are aligned with one another both in the first direction; and an ultrasonic waveguide extending through at least a portion of the shaft, wherein the ultrasonic waveguide comprises a bendable portion at the pivotable portion of the shaft.

2. The articulatable surgical instrument of claim 1, wherein the first rotatable member, the second rotatable member and the longitudinal axis are centered on a common plane.

3. The articulatable surgical instrument of claim 2, wherein the first direction is in the common plane.

4. The articulatable surgical instrument of claim 2, wherein the first direction is outside of the common plane.

5. The articulatable surgical instrument of claim 1, wherein each of the plurality of transverse spacer members defines a disk centered on the longitudinal axis, wherein each disk defines first and second openings for receiving the first and second rotatable members, respectively.

6. The articulatable surgical instrument of claim 1, wherein when the pivotable portion is substantially straight with the shaft, portions of the first rotatable member between each of the plurality of transverse spacer members extend parallel to the longitudinal axis, and portions of the second rotatable member between each of the plurality of transverse spacer members extend parallel to the longitudinal axis.

7. The articulatable surgical instrument of claim 1, wherein the first rotatable member is formed with a curvature in the first natural bias direction, and wherein the second rotatable member is formed with a curvature in the second natural bias direction.

8. The articulatable surgical instrument of claim 1, wherein the bias forces of the first rotatable member and the second rotatable member are substantially equal.

9. The articulatable surgical instrument of claim 1, wherein as the pivotable portion of the shaft articulates, the bendable portion of the ultrasonic waveguide bends.

10. A surgical instrument comprising:
an end effector comprising an ultrasonic blade;
a shaft extending proximally from the end effector, wherein the shaft comprises:
a pivotable portion positioned proximal to the end effector;
a first spacer positioned within the pivotable portion, wherein the first spacer comprises a first opening and a second opening;
a first rod extending through the first opening, wherein the first rod has been formed to exert a first force on the first spacer in a first rod bias direction, and wherein the first force and the first rod bias direction varies as the first rod rotates; and
a second rod extending through the second opening, wherein the second rod has been formed to exert a second force on the first spacer in a second rod bias direction, wherein the second force and the second rod bias direction varies as the second rod rotates, wherein the pivotable portion of the shaft is substantially parallel to a longitudinal axis when the first rod bias direction and the second rod bias direction are opposed and both the first rod and the second rod exert bias forces oriented radially outward from the longitudinal axis, and wherein the pivotable portion of the shaft is pivoted away from the longitudinal axis in a first direction when the first rod bias direction and the second rod bias direction are aligned both in the first direction; and an ultrasonic waveguide extending through at least a portion of the shaft, wherein the ultrasonic waveguide comprises a flexible portion at the pivotable portion of the shaft.

11. The surgical instrument of claim 10, further comprising a second spacer comprising a first opening and a second opening, wherein the first rod also extends through the first opening of the second spacer to force the second spacer in the first rod bias direction, and wherein the second rod also extends through the second opening of the second spacer to force the second spacer in the second rod bias direction.

12. The surgical instrument of claim 11, wherein when the pivotable portion is substantially straight with the shaft, a portion of the first rod between the first and second spacer members extends parallel to the longitudinal axis, and a portion of the second rod between the first and second spacer members extends parallel to the longitudinal axis.

13. The surgical instrument of claim 10, wherein the first rod is formed with a curvature in the first rod bias direction, and wherein the second rod is formed with a curvature in the second rod bias direction.

14. The surgical instrument of claim 10, wherein the first rod, the second rod, and the longitudinal axis are contained in a common plane when the first rod bias direction and the second rod bias direction are opposed.

15. The surgical instrument of claim 14, wherein the first direction is contained in the common plane.

16. The surgical instrument of claim 10, wherein the first rod bias direction is opposed to the second rod bias direction when the first rod bias direction is opposite the second rod bias direction.

17. The surgical instrument of claim 10, wherein the first spacer comprises a disk centered on the longitudinal axis.

18. The surgical instrument of claim 10, wherein as the pivotable portion of the shaft pivots, the flexible portion of the ultrasonic waveguide flexes.

19. An articulatable surgical instrument comprising:
an end effector comprising an ultrasonic blade;
a shaft extending proximally from the end effector along a longitudinal axis, wherein the shaft comprises:
a pivotable portion located at a proximal end of the shaft relative to the end effector, wherein the pivotable portion comprises a plurality of transverse spacer members;
a first rotatable member extending through the plurality of transverse spacer members parallel to the longitudinal axis, wherein the first rotatable member comprises a first natural bias away from the longitudinal axis, and wherein a direction of the first natural bias of the first rotatable member varies with rotation of the first rotatable member;
a second rotatable member extending through the plurality of transverse spacer members parallel to the longitudinal axis and offset from the first rotatable member along a direction perpendicular to the longitudinal axis, wherein the second rotatable member comprises a second natural bias away from the longitudinal axis, wherein a direction of the second natural bias of the second rotatable member varies with rotation of the second rotatable member, wherein the pivotable portion of the shaft is substantially straight when the first and second rotatable members are rotated such that the direction of the first natural bias of the first rotatable member and the direction of the second natural bias of the second rotatable member oppose one another and both the first rotatable member and the second rotatable member exert bias forces oriented radially outward from the longitudinal axis, and wherein the pivotable portion of the shaft articulates in a first direction away from the longitudinal axis when the first and second rotatable members are rotated such that the direction of the first natural bias of the first rotatable member and the direction of the second natural bias of the second rotatable member are aligned with one another both in the first direction; and an ultrasonic waveguide extending through the shaft, wherein the ultrasonic waveguide comprises a bendable portion at the pivotable portion of the shaft.

\* \* \* \* \*